(12) United States Patent
Lin et al.

(10) Patent No.: US 9,950,077 B2
(45) Date of Patent: Apr. 24, 2018

(54) ANTI-FOLATE RECEPTOR ALPHA (FRA) ANTIBODY-DRUG CONJUGATES AND METHODS OF USING THEREOF

(71) Applicants: BioAlliance C.V., Alkmaar (NL); AbGenomics International Inc., Dover, DE (US)

(72) Inventors: Rong-Hwa Lin, Palo Alto, CA (US); Shih-Yao Lin, Taipei (TW); Yu-Chi Hsieh, New Taipei (TW); Chiu-Chen Huang, Taipei (TW); Shu-Hua Lee, Taipei (TW); Yu-Ying Tsai, Taipei (TW); Feng-Lin Chiang, Taipei (TW); Li-An Hu, Taipei (TW)

(73) Assignees: BIOALLIANCE C.V., Alkmaar (NL); ABGENOMICS INTERNATIONAL INC., Dover, DE (US)

( * ) Notice: Subject to any disclaimer, the term of this patent is extended or adjusted under 35 U.S.C. 154(b) by 0 days.

(21) Appl. No.: 14/745,336

(22) Filed: Jun. 19, 2015

(65) Prior Publication Data
US 2016/0015827 A1 Jan. 21, 2016

Related U.S. Application Data

(60) Provisional application No. 62/015,321, filed on Jun. 20, 2014.

(51) Int. Cl.
| A61K 47/48 | (2006.01) |
| C07K 16/28 | (2006.01) |
| A61K 31/427 | (2006.01) |
| A61K 47/68 | (2017.01) |
| A61K 39/00 | (2006.01) |

(52) U.S. Cl.
CPC ...... *A61K 47/48561* (2013.01); *A61K 31/427* (2013.01); *A61K 47/6803* (2017.08); *A61K 47/6849* (2017.08); *A61K 47/6889* (2017.08); *C07K 16/28* (2013.01); *A61K 2039/505* (2013.01); *C07K 2317/24* (2013.01); *C07K 2317/52* (2013.01); *C07K 2317/73* (2013.01)

(58) Field of Classification Search
CPC ............................... A61K 47/48; C07K 16/28
USPC .................................... 424/179.1; 530/391.9
See application file for complete search history.

(56) References Cited

U.S. PATENT DOCUMENTS

| 4,816,567 A | 3/1989 | Cabilly et al. |
| 5,198,560 A | 3/1993 | Kadow |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,750,373 A | 5/1998 | Garrard et al. |
| 5,789,554 A | 8/1998 | Leung et al. |
| 5,985,908 A | 11/1999 | Boger |
| 6,060,608 A | 5/2000 | Boger |
| 6,214,345 B1 | 4/2001 | Firestone et al. |
| 6,262,271 B1 | 7/2001 | Boger |
| 6,281,354 B1 | 8/2001 | Boger |
| 6,486,326 B2 | 11/2002 | Boger |
| 6,548,530 B1 | 4/2003 | Boger |
| 6,762,020 B1 | 7/2004 | Mack et al. |
| 7,090,843 B1 | 8/2006 | Francisco et al. |
| 7,091,186 B2 | 8/2006 | Senter et al. |
| 7,223,837 B2 | 5/2007 | De Groot et al. |
| 7,256,257 B2 | 8/2007 | Doronina et al. |
| 7,332,164 B2 | 2/2008 | Greenwald et al. |
| 7,423,116 B2 | 9/2008 | Doronina et al. |
| 7,521,541 B2 | 4/2009 | Eigenbrot et al. |
| 7,553,816 B2 | 6/2009 | Senter et al. |
| 7,659,241 B2 | 2/2010 | Senter et al. |
| 7,674,605 B2 | 3/2010 | Lin et al. |
| 7,705,045 B2 | 4/2010 | De Groot et al. |
| 7,754,681 B2 | 7/2010 | Feng |
| 7,829,531 B2 | 11/2010 | Senter et al. |
| 7,855,275 B2 | 12/2010 | Eigenbrot et al. |
| 7,982,017 B2 | 7/2011 | Lin et al. |
| 8,153,581 B2 | 4/2012 | Kratz |
| 8,153,768 B2 | 4/2012 | Kunz et al. |
| 8,273,787 B2 | 9/2012 | Bell et al. |
| 8,309,093 B2 | 11/2012 | Gudas et al. |
| 8,394,607 B2 | 3/2013 | Ebens, Jr. et al. |
| 8,455,622 B2 | 6/2013 | McDonagh et al. |
| 8,568,718 B2 | 10/2013 | Lin et al. |
| 8,618,124 B2 | 12/2013 | Greenwald et al. |
| 9,089,614 B2 | 7/2015 | Lin et al. |

(Continued)

FOREIGN PATENT DOCUMENTS

| EP | 2357006 A2 | 8/2011 |
| JP | 2012-519711 A | 8/2012 |

(Continued)

OTHER PUBLICATIONS

Al-Lazikani, B. et al. (Nov. 7, 1997). "Standard Conformations for the Canonical Structures of Immunoglobulins," *Journal of Molecular Biology* 273(4):927-948.
Bandgar, B.P. et al. (2003). "Highly Rapid and Direct Synthesis of Monoacylated Piperazine Derivatives from Carboxylic Acids Under Mild Conditions," *Tetrahedron Letters* 44: 3855-3858.
Blencowe, C.A. et al. (2011). "Self-Immolative Linkers in Polymeric Delivery Systems," *Polym. Chem.* 2:773-790.
Boerner, P. et al. (Jul. 1, 1991). "Production of Antigen-Specific Human Monoclonal Antibodies from In Vitro-primed Human Splenocytes," *Journal of Immunology* 147(1):86-95.

(Continued)

*Primary Examiner* — Yan Xiao
(74) *Attorney, Agent, or Firm* — Morrison & Foerster LLP

(57) ABSTRACT

The present disclosure provides anti-folate receptor alpha (FRA) antibody-drug conjugates comprising a hydrophilic self-immolative linker. The present disclosures further provide compositions and methods for treating cancers.

49 Claims, 6 Drawing Sheets

(56) References Cited

U.S. PATENT DOCUMENTS

| | | | |
|---|---|---|---|
| 9,216,228 | B2 | 12/2015 | Kratz |
| 9,408,923 | B2 * | 8/2016 | Lin .................. A61K 47/48384 |
| 2003/0083263 | A1 | 5/2003 | Doronina et al. |
| 2005/0232929 | A1 | 10/2005 | Kadkhodayan et al. |
| 2005/0238649 | A1 | 10/2005 | Doronina et al. |
| 2006/0024317 | A1 | 2/2006 | Boyd et al. |
| 2006/0193865 | A1 | 8/2006 | Govindan et al. |
| 2007/0258987 | A1 | 11/2007 | Francisco et al. |
| 2008/0050310 | A1 | 2/2008 | Ebens, Jr. |
| 2008/0166363 | A1 | 7/2008 | Govindan et al. |
| 2009/0068178 | A1 | 3/2009 | Crowley et al. |
| 2009/0258420 | A1 | 10/2009 | Van Vlijmen et al. |
| 2009/0274697 | A1 * | 11/2009 | Grasso .................. C07K 16/28 424/138.1 |
| 2010/0124551 | A1 | 5/2010 | Lin et al. |
| 2011/0033378 | A1 | 2/2011 | Dimasi et al. |
| 2011/0137017 | A1 | 6/2011 | Eigenbrot et al. |
| 2011/0256157 | A1 | 10/2011 | Howard et al. |
| 2011/0301334 | A1 | 12/2011 | Bhakta et al. |
| 2011/0305631 | A1 | 12/2011 | Govindan et al. |
| 2012/0148580 | A1 | 6/2012 | Chennasmsetty et al. |
| 2012/0213705 | A1 | 8/2012 | Dimasi et al. |
| 2012/0282175 | A1 | 11/2012 | Carrigan et al. |
| 2013/0066054 | A1 | 3/2013 | Humphreys et al. |
| 2013/0177526 | A1 | 7/2013 | Govindan et al. |
| 2013/0177579 | A1 | 7/2013 | Lin et al. |
| 2014/0105899 | A1 | 4/2014 | Lin et al. |
| 2014/0170063 | A1 | 6/2014 | Govindan et al. |
| 2014/0193437 | A1 | 7/2014 | Lin et al. |
| 2014/0363454 | A1 | 12/2014 | Jackson et al. |
| 2015/0352222 | A1 | 12/2015 | Lin et al. |
| 2015/0366990 | A1 | 12/2015 | Park et al. |
| 2016/0015830 | A1 | 1/2016 | Lin et al. |
| 2016/0015831 | A1 | 1/2016 | Lin et al. |
| 2016/0067351 | A1 * | 3/2016 | Geierstanger .... A61K 47/48438 435/69.6 |
| 2016/0051695 | A1 | 5/2016 | Lin et al. |

FOREIGN PATENT DOCUMENTS

| | | |
|---|---|---|
| RU | 94016384 A | 11/1996 |
| WO | WO-99/58572 A1 | 11/1999 |
| WO | WO-2002/043661 A2 | 6/2002 |
| WO | WO-2002/088172 A2 | 11/2002 |
| WO | WO-2002/101069 A2 | 12/2002 |
| WO | WO-2003/000113 A2 | 1/2003 |
| WO | WO-2003/088808 A2 | 10/2003 |
| WO | WO-2004/043493 A1 | 5/2004 |
| WO | WO-2004/085386 A2 | 10/2004 |
| WO | WO-2004/085386 A3 | 10/2004 |
| WO | WO-2005/081711 A2 | 9/2005 |
| WO | WO-2005/099768 A2 | 10/2005 |
| WO | WO-2005/099768 A3 | 10/2005 |
| WO | WO-2006/034488 A2 | 3/2006 |
| WO | WO-2006/034488 A3 | 3/2006 |
| WO | WO-2007/103288 A2 | 9/2007 |
| WO | WO-2007/140371 A2 | 12/2007 |
| WO | WO-2007/146172 A2 | 12/2007 |
| WO | WO-2007/146172 A3 | 12/2007 |
| WO | WO-2008/038024 A1 | 4/2008 |
| WO | WO-2008/070593 A2 | 6/2008 |
| WO | WO-2008/070593 A3 | 6/2008 |
| WO | WO-2008/083312 A2 | 7/2008 |
| WO | WO-2008/083312 A3 | 7/2008 |
| WO | WO-2008/098788 A2 | 8/2008 |
| WO | WO-2009/079649 A1 | 6/2009 |
| WO | WO-2009/092011 A1 | 7/2009 |
| WO | WO-2009/099741 A1 | 8/2009 |
| WO | WO-2010/111018 A1 | 9/2010 |
| WO | WO-2010/111018 A8 | 9/2010 |
| WO | WO-2010/141902 A2 | 12/2010 |
| WO | WO-2010/141902 A3 | 12/2010 |
| WO | WO-2011/005481 A1 | 1/2011 |
| WO | WO-2011/106528 A1 | 9/2011 |
| WO | WO-2011/133039 A2 | 10/2011 |
| WO | WO-2011/156328 A1 | 12/2011 |
| WO | WO-2012/112687 A1 | 8/2012 |
| WO | WO-2012/135675 A3 | 10/2012 |
| WO | WO-2012/162482 A1 | 11/2012 |
| WO | WO-2012/177837 A2 | 12/2012 |
| WO | WO-2013/093809 A1 | 6/2013 |
| WO | WO-2013/103800 A1 | 7/2013 |
| WO | WO-2013/173391 A1 | 11/2013 |
| WO | WO-2013/173392 A1 | 11/2013 |
| WO | WO-2013/173393 A1 | 11/2013 |
| WO | WO-2013/181597 A2 | 12/2013 |
| WO | WO-2013/181597 A3 | 12/2013 |
| WO | WO-2014/009774 A1 | 1/2014 |
| WO | WO-2014/011520 A1 | 1/2014 |
| WO | WO-2014/012479 A1 | 1/2014 |
| WO | WO-2014/057118 A1 | 4/2014 |
| WO | WO-2014/100762 A1 | 6/2014 |
| WO | WO-2014/107024 A1 | 7/2014 |
| WO | WO-2014/124316 A2 | 8/2014 |
| WO | WO-2014/145090 A1 | 9/2014 |
| WO | WO-2014/197871 A2 | 12/2014 |
| WO | WO-2015/012904 A2 | 1/2015 |
| WO | WO-2015/012904 A3 | 1/2015 |
| WO | WO-2015/104385 A2 | 7/2015 |
| WO | WO-2015/195904 A1 | 12/2015 |
| WO | WO-2015/196089 A1 | 12/2015 |
| WO | WO-2015/196167 A1 | 12/2015 |
| WO | WO-2017/120534 A1 | 7/2017 |

OTHER PUBLICATIONS

Cabilly, S. et al. (Jun. 1984). "Generation of Antibody Activity from Immunoglobulin Polypeptide Chains Produced in *Escherichia coli*," *Proceedings of the National Academy of Sciences of the United States of America* 81(11) :3273-3277.

Carpino, L.A. (1993). "1-Hydroxy-7Azabenzotriazole. An Efficient Peptide Coupling Additive," *J. Am. Chem. Soc.* 115(10):4397-4398.

Carpino, L.A. et al. (1995). "Tetramethylfluoroformamidinium Hexafluorophosphate: A Rapid-Acting Peptide Coupling Reagent for Solution and Solid Phase Peptide Synthesis," *J. Am. Chem. Soc.* 117(19): 5401-5402.

Carter, P. J. et. al. (May/Jun. 2008). "Antibody-Drug Conjugates for Cancer Therapy," *The Cancer Journal* 14(3):154-169.

Chothia, C. et al. (Aug. 1987). "Canonical Structures for the Hypervariable Regions of Immunoglobulins," *J. Mol. Biol.* 196(4):901-917.

Cole, S.P.C. et al. (1985). "The EBV-Hybridoma Technique and its Application to Human Lung Cancer," *Monoclonal Antibodies and Cancer Therapy*, Reisfeld, R.A. et al. ed., Alan R. Liss Inc., New York, NY, 77-96.

Doronina, S.O. et al. (Jul. 2003, e-pub. Jun. 1, 2003). "Development of Potent Monoclonal Antibody Auristatin Conjugates for Cancer Therapy," *Nature Biotechnology*, 21(7):778-784.

Ducry L. et al. (2010, e-pub. Sep. 21, 2009). "Antibody-Drug Conjugates: Linking Cytotoxic Payloads to Monoclonal Antibodies," *Bioconjugate Chem*, 21:5-13.

Extended European Search Report dated Jul. 27, 2016, for European Patent Application No. 13865282.1, filed on Dec. 20, 2013, 7 pages.

Farber, S. et al. (Jun. 3, 1948). "Temporary Remissions in Acute Leukemia in Children Produced by Folic Acid Antagonist, 4-Aminopteroyl-Glutamic Acid (Aminopterin", *New England Journal of Medicine* 238(23):787-793.

Francisco, J.A. et al. (Aug. 15, 2003). "cAC10-vcMMAE, an Anti-CD30-Monomethyl Auristatin E Conjugate with Potent and Selective Antitumor Activity," *Blood*, 102(4):1458-1465.

Genbank "Immunoglobulin Light Chain Variable Region, Partial [*Homo sapiens*]," Accession No. AB174084, located at http://www.ncbi.nlm.nih., gov/protein/ABI74084>last visited on Oct. 21, 2014, 2 pages.

Genbank "Ig H-Chain V-domain, Partial [*Homo sapiens*]," Accession No. CAA79298, located at <http:ncbi.nlm.nih.gov/protein/CAA79298>, last visited on Oct. 21, 2014, 2 pages.

(56) References Cited

OTHER PUBLICATIONS

Holt, L.J. et al. (Nov. 2003). "Domain Antibodies: Proteins for Therapy," *Trends Biotechnology* 21(11):484-490.
Hoogenboom, H.R. et al. (Sep. 1991). "By-Passing Immunisation: Human Antibodies from Synthetic Repertoires of Germline $V_H$ Gene Segments Rearranged in Vitro," *Journal of Molecular Biology* 227 (2) :381 -388.
International Search Report, dated Apr. 4, 2014, for PCT Application No. PCT/US2013/077306, filed Dec. 20, 2013, 7 pages.
International Search Report, dated Oct. 13, 2015, for PCT Application No. PCT/US2015/036721, filed Jun. 19, 2015, 11 pages.
International Search Report, dated Oct. 14, 2015, for PCT Application No. PCT/US2015/036824, filed Jun. 19, 2015, 5 pages.
Jeffrey S. C. et. al. (Feb. 5, 2005). "Design, Synthesis, and in Vitro Evaluation of Dipeptide-Based Antibody Minor Groove Binder Conjugates," *J. Med. Chem.* 48(5):1344-1358.
Jeffrey, S.C. et al. (Jul. 17, 2013, e-published Jun. 28, 2013). "A Potent Anti-CD70 Antibody-Drug Conjugate Combining a Dimeric Pyrrolobenzodiazepine Drug with Site-Specific Conjugation Technology," *Bioconjug. Chem.* 24(7):1256-1263.
Junutula, J.R. et al. (Aug. 2008, e-published Jul. 20, 2008). "Site-Specific Conjugation of a Cytotoxic Drug to an Antibody Improves the Therapeutic Index," *Nat. Biotech.* 26(8):925-932, Supplemental Materials pp. 1-34.
Kitson, S. et al.. "Antibody-drug conjugates (ADCs)—Biotherapeutic bullets", Monographic Supplement Series CROs/CMOs—Chemistry Today, 2013, 31(4), 30-36.
Koblinski, J.E. et al. (Feb. 15, 2000). "Unraveling the Role of Proteases in Cancer," *Clin. Chem. Acta* 291(2):113-135.
Kohler, G. et al. (Aug. 7, 1975). "Continuous Cultures of Fused Cells Secreting Antibody of Predefined Specificity," *Nature* 256(5517):495-497.
Li, P. et al. (Aug. 2001). "The Development of Highly Efficient Onium-Type Peptide Coupling Reagents Based Upon Rational Molecular Design," *J. Pept. Res.* 58(2):129-139.
Li, D. et al. "DCDT2980S, an anti-CD22-monomethyl Auristatin E antibody-drug conjugate, is a potential treatment for non-Hodgkin lymphoma", Molecular Cancer Therapeutics, 2013, 12(7): 1255-1265.
Loudon, G.M. (2002). *Organic Chemistry*, Fourth Edition, Oxford University Press, New York, pp. 360-361, 1084-1085.
Lyons, A. et al. (Aug. 1990). "Site-Specific Attachment to Recombinant Antibodies via Introduced Surface Cysteine Residues," *Protein Engineering* 3(8):703-708.
McCafferty, J. et al. (Dec. 6, 1990). "Phage Antibodies: Filamentous Phage Displaying Antibody Variable Domains," *Nature* 348(6301):552-554.
Marks, J. D. et al. (Dec. 5, 1991). "By-Passing Immunization: Human Antibodies From V-Gene Libraries Displayed on Phage," *Journal of Molecular Biology* 222(3):581-597.
Muyldermans, S. et al. (Jun. 2001). "Single Domain Camel Antibodies: Current Status," *Journal of Biotechnology* 74(4):277-302.
Polson, A. G. et al. (Mar. 15, 2009, e-pub. Mar. 3, 2009). "Antibody-drug conjugates for the treatment of non-Hodgkin's lymphoma: Target and linker-drug selection", Cancer Research, 269(6), 2358-2364.
Sheets, M.D. et al. (May 26, 1998). "Efficient Construction of a Large Nonimmune Phage Antibody Library: The Production of High-Affinity Human Single-Chain Antibodies to Protein Antigens," *Proceedings of the National Academy of Sciences of the United States of America* 95(11): 6157-6162.
Spearman, M.E. et al. (Oct. 23, 1986-pub. Feb. 3, 1987). "Disposition of the Monoclonal Antibody-Vinca Alkaloid Conjugate KS1/4-DAVLB (LY256787) and Free 4-Desacetylvinblastine in Tumor-Bearing Nude Mice," *The Journal of Phamacology and Experimental Therapeutics*, 241(2)696-703.
Stimmel, J.B. et al. (Sep. 29, 2000, e-published Jul. 3, 2000). "Site-Specific Conjugation on Serine → Cysteine Variant Monoclonal Antibodies," *J. Biol. Chem.* 275(39):30445-30450.
Sun, M.M.C. et al. (Sep./Oct. 2005). "Reduction-Alkylation Strategies for the Modification of Specific Monoclonal Antibody Disulfides," *Bioconjug. Chem.* 16(5):1282-1290.
Teicher, B.A. et al. (Dec. 2009). "Antibody-Drug Conjugate Targets," *Current Cancer Drug Targets* 9(8):982-1004.
Trail, P. A. et al. (Jul. 9, 1993). "Cure of Xenografted Human Carcinomas by BR96-Doxorubicin Immunoconjugates," *Science* 261(5118):212-215.
Trail, P. A. et al. (Jan. 1, 1997). "Effect of Linker Variation on the Stability, Potency, and Efficacy of Carcinoma-Reactive BR64-Doxorubicin lmmunoconjugates," *Cancer Research* 57(1):100-105.
Vaughan, T.J. et al. (Mar. 1996). "Human Antibodies with Sub-Nanomolar Affinities Isolated from a Large Non-Immunized Phage Display Library," *Nature Biotechnology* 14(3):309-314.
Vlahov, I.R. et al., "Engineering folate-drug conjugates to target cancer: From chemistry to clinic". *Bioconjugate Chemistry*, 2012, 23, 1357-1369.
Written Opinion dated Apr. 4, 2014, for PCT Application No. PCT/US2013/077306, filed Dec. 20, 2013, 10 pages.
Written Opinion dated Oct. 13, 2015, for PCT Application No. PCT/US2015/036721, filed Jun. 19, 2015, 9 pages.
Written Opinion dated Oct. 14, 2015, for PCT Application No. PCT/US2015/036824, filed on Jun. 20, 2014, 8 pages.
Yu Shang-Fan et al.. "A novel anti-CD22 anthracycline-based antibody-drug conjugate (ADC) that overcomes resistance to Auristatin-based ADC's", Clinical Cancer Research, 2015, 21(14): 3298-3306.
Coney, L.R. et al. (Nov. 15, 1991). "Cloning of a Tumor-Associated Antigen: MOv18 and MOv19 Antibodies Recognize a Folate-Binding Protein," *Cancer Res.* 51:6125-6132.
De Groot, F.M.H. et al. (2001). "Elongated Multiple Electronic Cascade and Cyclization Spacer Systems in Activatible Anticancer Prodrugs for Enhanced Drug Release," *J. Org. Chem.* 66:8815-8830.
DiJoseph, J.F. et al. (2007). "Therapeutic Potential of CD22-Specific Antibody-Targeted Chemotherapy Using Inotuzumab Ozogamicin (CMC-544) for the Treatment of Acute Lymphoblastic Leukemia," *Leukemia* 21:2240-2245.
Ebel, W. et al. (Mar. 9, 2007). "Preclinical Evaluation of MORAb-003, A Humanized Monoclonal Antibody Antagonizing Folate Receptor-Alpha," *Cancer Immun.* 7:1-8.
Gianolio, D.A. et al. (2012). "Targeting HER2-Positive Cancer With Dolastatin 15 Derivatives Conjugated to Trastuzumab, Novel Antibody-Drug Conjugates," *Cancer Chemother. Pharmol*, 70(3):439-49.
Haso, W. et al. (Feb. 14, 2013). "Anti-CD22-Chimeric Antigen Receptors Targeting B-Cell Precusor Acute Lymphoblastic Leukemia," *Blood* 121(7):1165-1174.
International Search Report dated Sep. 15, 2015, for PCT Application No. PCT/US2015/036414, filed Jun. 18, 2015, 8 pages.
Kalli, K.R. (2007). "Drug Evaluation: MORAb-003, A Fully Humanized Monoclonal Antibody Against the Folate Receptor α, For the Potential Treatment of Epithelial Ovarian Cancer," *Curr. Opin. Investig. Drugs* 8(12):1067-1073.
Kantarjian, H. et al. (Apr. 2012; e-published Feb. 21, 2012). "Inotuzumab Ozogamicin, An Anti-CD22-Calecheamicin Conjugate, For Refractory and Relapsed Acute Lymphocytic Leukaemia: A Phase 2 Study," *Lancet Oncol.* 13:403-411.
Kato, J. et al. (Dec. 2012). "Efficacy and Toxicity of a CD22-Targeted Antibody-Saporin Conjugate in a Xenograft Model of Non-Hodgkin's Lymphoma," *Oncolmmunology* 1(9):1469-1475.
Krauss, J. et al. (2003). "Specificity Grafting of Human Antibody Frameworks Selected From a Phage Display Library: Generation of a Highly Stable Humanized Anti-CD22 Single-Chain Fv Fragment," *Protein Engineering* 16(10):753-759.
Kreitman, R.J. et al. (Oct. 15, 2011). "Antibody-Fusion Proteins Anti-CD22 Recombinant Immunotoxin Moxetumomab Pasudotox," *Clin. Cancer Res.* 17(20):6398-6405.
Leamon, C.P. et al. (Jul. 1991). "Delivery of Macromolecules Into Living Cells: A Method That Exploits Folate Receptor Endocytosis," *Proc. Natl. Acad. Sci. USA* 88:5572-5576.

(56) References Cited

OTHER PUBLICATIONS

Leonard, J.P. et al. (Aug. 1, 2005). "Combination Antibody Therapy With Epratuzumab and Rituximab in Relapsed or Refractory Non-Hodgkin's Lymphoma," *J. Clin. Oncol.* 23(22):5044-5051.

Lindén, O. et al. (Jul. 15, 2005). "Dose-Fractionated Radioimmunotherapy in Non-Hodgkin's Lymphoma Using DOTA-Conjugated, $^{90}$Y-Radiolabeled, Humanized Anti-CD22 Monoclonal Antibody, Epratuzumab," *Clin. Cancer Res.* 11(14):5215-5222.

Stubenrauch, K. et al. (2010). "Impact of Molecular Processing in the Hinge Region of Therapeutic IgG4 Antibodies on Disposition Profiles in Cynomolgus Monkeys," *Drug Metab. Dispos.* 38(1):84-91.

Sullivan-Chang, L. et al. (2013). "Targeting CD22 in B-Cell Malignancies: Current Status and Clinical Outlook," *BioDrugs* 27(4):293-304.

Written Opinion dated Sep. 15, 2015, for PCT Application No. PCT/US2015/036414, filed Jun. 18, 2015, 9 pages.

Xia, W. et al. (2010). "Folate-Targeted Therapies for Cancer," *J. Med. Chem.* 53(19):6811-6824.

Zacchetti, A. et al. (2009). "Lu-Labeled MOv18 As Compared to $^{131}$I- or $^{90}$Y-Labeled MOv18 Has the Better Therapeutic Effect in Eradication of Alpha Folate Receptor-Expressing Tumor Xenografts," *Nucl. Med. Biol.* 36:759-770.

Ab, O. et al. (Apr. 22, 2015). "IMGN853, a Folate Receptor-α (FRα)-Targeting AntibodyDrug Conjugate, Exhibits Potent Targeted Antitumor Activity against FR-Expressing Tumors," *Molecular Cancer Therapeutics* 14(7):1605-1613.

Li, H. et al. (May 19, 2010). "Folate-Immunoglobulin G as an Anticancer Therapeutic Antibody," *Bioconjugate Chemistry* 21(5):961-968.

Lu, J.Y. et al. (Jan. 1, 1999). "Folate-Targeted Enzyme Prodrug Cancer Therapy Utilizing Penicillin-V Amidase and a Doxorubicin Prodrug," *Journal of Drug Targeting*, 7(1):43-53.

Nagayoshi, R. et al. (Sep. 1, 2005): "Effectiveness of Anti-Folate Receptor β Antibody Conjugated With Truncated *Pseudomonas* Exotoxin In the Targeting of Rheumatoid Arthritis Synovial Macrophages," *Arthritis & Rheumatism*, 52(9):2666-2675.

Wang, Z. et al. (Aug. 1, 2015). "A Current Review of Folate Receptor Alpha As a Potential Tumor Target in Non-Small-Cell Lung Cancer," *Drug Design, Development and Therapy* p. 4989-4996.

Daintith, J. (2008). "A Dictionary of Chemistry," Oxford University Press, 6$^{th}$ ed., retrieved from <http://www.oxfordreference.com/view/10.1093/acref/9780199204632.001.0001/acref-9780199204632>, lasted visited Aug. 17, 2017, 2 pages.

Iupac Gold Book, retrieved from <https://goldbook.iupac.org/html/A/A00123.html>,last visited Aug. 17, 2017, 1 page.

Jain, N. et al. (2015, e-pub. Mar. 11, 2015). "Current ADC Linker Chemistry," *Pharm Res.* 32:3526-3540.

\* cited by examiner

Arrow indicates the time of ADC treatment.

SEQUENCE LISTING

<160> NUMBER OF SEQ ID NOS: 53

<210> SEQ ID NO 1
<211> LENGTH: 449
<212> TYPE: PRT
<213> ORGANISM: Artificial Sequence
<220> FEATURE:
<223> OTHER INFORMATION: Synthetic Construct

<400> SEQUENCE: 1

Glu Val Gln Leu Val Glu Ser Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr

```
                355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 2
<211> LENGTH: 446
<212> TYPE: PRT
<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Val Val Gln Pro Gly Arg
1               5                   10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270
```

```
Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 3
<211> LENGTH: 217
<212> TYPE: PRT
<213> ORGANISM: Artificial Sequence
<220> FEATURE:
<223> OTHER INFORMATION: Synthetic Construct

<400> SEQUENCE: 3

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190
```

-continued

```
Lys Val Tyr Ala Cys Glu Val Thr His Gln Gly Leu Ser Ser Pro Val
            195                 200                 205
Thr Lys Ser Phe Asn Arg Gly Glu Cys
        210                 215

<210> SEQ ID NO 4
<211> LENGTH: 433
<212> TYPE: PRT
<213> ORGANISM: Mus musculus

<400> SEQUENCE: 4

Gly Pro Glu Leu Val Lys Pro Gly Ala Ser Val Lys Ile Ser Cys Lys
  1               5                  10                  15
Ala Ser Asp Tyr Ser Phe Thr Gly Tyr Phe Met Asn Trp Val Met Gln
             20                  25                  30
Ser His Gly Lys Ser Leu Glu Trp Ile Gly Arg Ile Phe Pro Tyr Asn
         35                  40                  45
Gly Asp Thr Phe Tyr Asn Gln Lys Phe Lys Gly Arg Ala Thr Leu Thr
     50                  55                  60
Val Asp Lys Ser Ser Ser Thr Ala His Met Glu Leu Arg Ser Leu Ala
 65                  70                  75                  80
Ser Glu Asp Ser Ala Val Tyr Phe Cys Ala Arg Gly Thr His Tyr Phe
                 85                  90                  95
Asp Tyr Trp Gly Gln Gly Thr Thr Leu Thr Val Ser Ser Ala Lys Thr
            100                 105                 110
Thr Pro Pro Ser Val Tyr Pro Leu Ala Pro Gly Ser Ala Ala Gln Thr
        115                 120                 125
Asn Ser Met Val Thr Leu Gly Cys Leu Val Lys Gly Tyr Phe Pro Glu
    130                 135                 140
Pro Val Thr Val Thr Trp Asn Ser Gly Ser Leu Ser Ser Gly Val His
145                 150                 155                 160
Thr Phe Pro Ala Val Leu Gln Ser Asp Leu Tyr Thr Leu Ser Ser Ser
                165                 170                 175
Val Thr Val Pro Ser Ser Pro Arg Pro Ser Glu Thr Val Thr Cys Asn
            180                 185                 190
Val Ala His Pro Ala Ser Ser Thr Lys Val Asp Lys Lys Ile Val Pro
        195                 200                 205
Arg Asp Cys Gly Cys Lys Pro Cys Ile Cys Thr Val Pro Glu Val Ser
    210                 215                 220
Ser Val Phe Ile Phe Pro Pro Lys Pro Lys Asp Val Leu Thr Ile Thr
225                 230                 235                 240
Leu Thr Pro Lys Val Thr Cys Val Val Asp Ile Ser Lys Asp Asp
                245                 250                 255
Pro Glu Val Gln Phe Ser Trp Phe Val Asp Asp Val Glu Val His Thr
            260                 265                 270
Ala Gln Thr Gln Pro Arg Glu Glu Gln Phe Asn Ser Thr Phe Arg Ser
        275                 280                 285
Val Ser Glu Leu Pro Ile Met His Gln Asp Trp Leu Asn Gly Lys Glu
    290                 295                 300
Phe Lys Cys Arg Val Asn Ser Ala Ala Phe Pro Ala Pro Ile Glu Lys
305                 310                 315                 320
Thr Ile Ser Lys Thr Lys Gly Arg Pro Lys Ala Pro Gln Val Tyr Thr
                325                 330                 335
Ile Pro Pro Pro Lys Glu Gln Met Ala Lys Asp Lys Val Ser Leu Thr
```

```
            340                 345                 350
Cys Met Ile Thr Asp Phe Phe Pro Glu Asp Ile Thr Val Glu Trp Gln
                355                 360                 365
Trp Asn Gly Gln Pro Ala Glu Asn Tyr Lys Asn Thr Gln Pro Ile Met
            370                 375                 380
Asn Thr Asn Gly Ser Tyr Phe Val Tyr Ser Lys Leu Asn Val Gln Lys
385                 390                 395                 400
Ser Asn Trp Glu Ala Gly Asn Thr Phe Thr Cys Ser Val Leu His Glu
                405                 410                 415
Gly Leu His Asn His Thr Glu Lys Ser Leu Ser His Ser Pro Gly
            420                 425                 430
Lys

<210> SEQ ID NO 5
<211> LENGTH: 207
<212> TYPE: PRT
<213> ORGANISM: Mus musculus

<400> SEQUENCE: 5

Pro Ala Ser Leu Ser Ala Ser Val Gly Glu Thr Val Thr Ile Thr Cys
1               5                   10                  15
Arg Thr Ser Glu Asn Ile Phe Ser Tyr Leu Ala Trp Tyr Gln Gln Lys
                20                  25                  30
Gln Gly Ile Ser Pro Gln Leu Leu Val Tyr Asn Ala Lys Thr Leu Ala
            35                  40                  45
Glu Gly Val Pro Ser Arg Phe Ser Gly Ser Gly Thr Gln Phe
        50                  55                  60
Ser Leu Lys Ile Asn Ser Leu Gln Pro Glu Asp Phe Gly Ser Tyr Tyr
65                  70                  75                  80
Cys Gln His His Tyr Ala Phe Pro Trp Thr Phe Gly Gly Gly Ser Lys
                85                  90                  95
Leu Glu Ile Lys Arg Ala Asp Ala Ala Pro Thr Val Ser Ile Phe Pro
            100                 105                 110
Pro Ser Ser Glu Gln Leu Thr Ser Gly Gly Ala Ser Val Val Cys Phe
        115                 120                 125
Leu Asn Asn Phe Tyr Pro Lys Asp Ile Asn Val Lys Trp Lys Ile Asp
130                 135                 140
Gly Ser Glu Arg Gln Asn Gly Val Leu Asn Ser Trp Thr Asp Gln Asp
145                 150                 155                 160
Ser Lys Asp Ser Thr Tyr Ser Met Ser Ser Thr Leu Thr Leu Thr Lys
                165                 170                 175
Asp Glu Tyr Glu Arg His Asn Ser Tyr Thr Cys Glu Ala Thr His Lys
            180                 185                 190
Thr Ser Thr Ser Pro Ile Val Lys Ser Phe Asn Arg Asn Glu Cys
        195                 200                 205

<210> SEQ ID NO 6
<211> LENGTH: 448
<212> TYPE: PRT
<213> ORGANISM: Artificial Sequence
<220> FEATURE:
<223> OTHER INFORMATION: Synthetic Construct

<400> SEQUENCE: 6

Gln Val Gln Leu Val Gln Ser Gly Ala Glu Val Val Lys Pro Gly Ala
1               5                   10                  15
```

```
Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
            35                  40                  45

Gly Arg Ile His Pro Tyr Asp Gly Asp Thr Phe Tyr Asn Gln Lys Phe
 50                  55                  60

Gln Gly Lys Ala Thr Leu Thr Val Asp Lys Ser Ser Asn Thr Ala His
 65                  70                  75                  80

Met Glu Leu Leu Ser Leu Thr Ser Glu Asp Phe Ala Val Tyr Tyr Cys
            85                  90                  95

Thr Arg Tyr Asp Gly Ser Arg Ala Met Asp Tyr Trp Gly Gln Gly Thr
            100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
    355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
```

435         440         445

<210> SEQ ID NO 7
<211> LENGTH: 218
<212> TYPE: PRT
<213> ORGANISM: Artificial Sequence
<220> FEATURE:
<223> OTHER INFORMATION: Synthetic Construct

<400> SEQUENCE: 7

Asp Ile Val Leu Thr Gln Ser Pro Leu Ser Leu Ala Val Ser Leu Gly
 1               5                  10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
    50                  55                  60

Arg Phe Ser Gly Ser Gly Ser Lys Thr Asp Phe Thr Leu Thr Ile Ser
65                  70                  75                  80

Pro Val Glu Ala Glu Asp Ala Ala Thr Tyr Tyr Cys Gln Gln Ser Arg
                85                  90                  95

Glu Tyr Pro Tyr Thr Phe Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 8
<211> LENGTH: 119
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Glu Ser Gly Gly Gly Val Val Gln Pro Gly Arg
 1               5                  10                  15

Ser Leu Arg Leu Ser Cys Ser Ala Ser Gly Phe Thr Phe Ser Gly Tyr
            20                  25                  30

Gly Leu Ser Trp Val Arg Gln Ala Pro Gly Lys Gly Leu Glu Trp Val
        35                  40                  45

Ala Met Ile Ser Ser Gly Gly Ser Tyr Thr Tyr Tyr Ala Asp Ser Val
    50                  55                  60

Lys Gly Arg Phe Ala Ile Ser Arg Asp Asn Ala Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg His Gly Asp Asp Pro Ala Trp Phe Ala Tyr Trp Gly Gln Gly
            100                 105                 110

Thr Pro Val Thr Val Ser Ser
        115

<210> SEQ ID NO 9
<211> LENGTH: 110
<212> TYPE: PRT
<213> ORGANISM: Artificial Sequence
<220> FEATURE:
<223> OTHER INFORMATION: Synthetic Construct

<400> SEQUENCE: 9

Asp Ile Gln Leu Thr Gln Ser Pro Ser Ser Leu Ser Ala Ser Val Gly
1               5                   10                  15

Asp Arg Val Thr Ile Thr Cys Ser Val Ser Ser Ile Ser Ser Asn
            20                  25                  30

Asn Leu His Trp Tyr Gln Gln Lys Pro Gly Lys Ala Pro Lys Pro Trp
        35                  40                  45

Ile Tyr Gly Thr Ser Asn Leu Ala Ser Gly Val Pro Ser Arg Phe Ser
    50                  55                  60

Gly Ser Gly Ser Gly Thr Asp Tyr Thr Phe Thr Ile Ser Ser Leu Gln
65                  70                  75                  80

Pro Glu Asp Ile Ala Thr Tyr Tyr Cys Gln Gln Trp Ser Ser Tyr Pro
                85                  90                  95

Tyr Met Tyr Thr Phe Gly Gln Gly Thr Lys Val Glu Ile Lys
            100                 105                 110

<210> SEQ ID NO 10
<211> LENGTH: 109
<212> TYPE: PRT
<213> ORGANISM: Mus musculus

<400> SEQUENCE: 10

Gly Pro Glu Leu Val Lys Pro Gly Ala Ser Val Lys Ile Ser Cys Lys
1               5                   10                  15

Ala Ser Asp Tyr Ser Phe Thr Gly Tyr Phe Met Asn Trp Val Met Gln
            20                  25                  30

Ser His Gly Lys Ser Leu Glu Trp Ile Gly Arg Ile Phe Pro Tyr Asn
        35                  40                  45

Gly Asp Thr Phe Tyr Asn Gln Lys Phe Lys Gly Arg Ala Thr Leu Thr
    50                  55                  60

Val Asp Lys Ser Ser Ser Thr Ala His Met Glu Leu Arg Ser Leu Ala
65                  70                  75                  80

Ser Glu Asp Ser Ala Val Tyr Phe Cys Ala Arg Gly Thr His Tyr Phe
                85                  90                  95

Asp Tyr Trp Gly Gln Gly Thr Thr Leu Thr Val Ser Ser
            100                 105

<210> SEQ ID NO 11
<211> LENGTH: 100
<212> TYPE: PRT
<213> ORGANISM: Mus musculus

<400> SEQUENCE: 11

Pro Ala Ser Leu Ser Ala Ser Val Gly Glu Thr Val Thr Ile Thr Cys
1               5                   10                  15

-continued

```
Arg Thr Ser Glu Asn Ile Phe Ser Tyr Leu Ala Trp Tyr Gln Gln Lys
            20                  25                  30

Gln Gly Ile Ser Pro Gln Leu Leu Val Tyr Asn Ala Lys Thr Leu Ala
        35                  40                  45

Glu Gly Val Pro Ser Arg Phe Ser Gly Ser Gly Thr Gln Phe
 50                  55                  60

Ser Leu Lys Ile Asn Ser Leu Gln Pro Glu Asp Phe Gly Ser Tyr Tyr
 65                  70                  75                  80

Cys Gln His His Tyr Ala Phe Pro Trp Thr Phe Gly Gly Gly Ser Lys
                85                  90                  95

Leu Glu Ile Lys
            100

<210> SEQ ID NO 12
<211> LENGTH: 118
<212> TYPE: PRT
<213> ORGANISM: Artificial Sequence
<220> FEATURE:
<223> OTHER INFORMATION: Synthetic Construct

<400> SEQUENCE: 12

Gln Val Gln Leu Val Gln Ser Gly Ala Glu Val Val Lys Pro Gly Ala
 1               5                  10                  15

Ser Val Lys Ile Ser Cys Lys Ala Ser Gly Tyr Thr Phe Thr Gly Tyr
            20                  25                  30

Phe Met Asn Trp Val Lys Gln Ser Pro Gly Gln Ser Leu Glu Trp Ile
        35                  40                  45

Gly Arg Ile His Pro Tyr Asp Gly Asp Thr Phe Tyr Asn Gln Lys Phe
     50                  55                  60

Gln Gly Lys Ala Thr Leu Thr Val Asp Lys Ser Ser Asn Thr Ala His
 65                  70                  75                  80

Met Glu Leu Leu Ser Leu Thr Ser Glu Asp Phe Ala Val Tyr Tyr Cys
                85                  90                  95

Thr Arg Tyr Asp Gly Ser Arg Ala Met Asp Tyr Trp Gly Gln Gly Thr
            100                 105                 110

Thr Val Thr Val Ser Ser
        115

<210> SEQ ID NO 13
<211> LENGTH: 111
<212> TYPE: PRT
<213> ORGANISM: Artificial Sequence
<220> FEATURE:
<223> OTHER INFORMATION: Synthetic Construct

<400> SEQUENCE: 13

Asp Ile Val Leu Thr Gln Ser Pro Leu Ser Leu Ala Val Ser Leu Gly
 1               5                  10                  15

Gln Pro Ala Ile Ile Ser Cys Lys Ala Ser Gln Ser Val Ser Phe Ala
            20                  25                  30

Gly Thr Ser Leu Met His Trp Tyr His Gln Lys Pro Gly Gln Gln Pro
        35                  40                  45

Arg Leu Leu Ile Tyr Arg Ala Ser Asn Leu Glu Ala Gly Val Pro Asp
     50                  55                  60

Arg Phe Ser Gly Ser Gly Ser Lys Thr Asp Phe Thr Leu Thr Ile Ser
 65                  70                  75                  80

Pro Val Glu Ala Glu Asp Ala Ala Thr Tyr Tyr Cys Gln Gln Ser Arg
```

85                  90                  95
Glu Tyr Pro Tyr Thr Phe Gly Gly Thr Lys Leu Glu Ile Lys
            100                 105                 110

<210> SEQ ID NO 14
<211> LENGTH: 5
<212> TYPE: PRT
<213> ORGANISM: Artificial Sequence
<220> FEATURE:
<223> OTHER INFORMATION: Synthetic Construct

<400> SEQUENCE: 14

Gly Tyr Gly Leu Ser
 1               5

<210> SEQ ID NO 15
<211> LENGTH: 17
<212> TYPE: PRT
<213> ORGANISM: Artificial Sequence
<220> FEATURE:
<223> OTHER INFORMATION: Synthetic Construct

<400> SEQUENCE: 15

Met Ile Ser Ser Gly Gly Ser Tyr Thr Tyr Tyr Ala Asp Ser Val Lys
 1               5                  10                  15

Gly

<210> SEQ ID NO 16
<211> LENGTH: 10
<212> TYPE: PRT
<213> ORGANISM: Artificial Sequence
<220> FEATURE:
<223> OTHER INFORMATION: Synthetic Construct

<400> SEQUENCE: 16

His Gly Asp Asp Pro Ala Trp Phe Ala Tyr
 1               5                  10

<210> SEQ ID NO 17
<211> LENGTH: 12
<212> TYPE: PRT
<213> ORGANISM: Artificial Sequence
<220> FEATURE:
<223> OTHER INFORMATION: Synthetic Construct

<400> SEQUENCE: 17

Ser Val Ser Ser Ser Ile Ser Ser Asn Asn Leu His
 1               5                  10

<210> SEQ ID NO 18
<211> LENGTH: 7
<212> TYPE: PRT
<213> ORGANISM: Artificial Sequence
<220> FEATURE:
<223> OTHER INFORMATION: Synthetic Construct

<400> SEQUENCE: 18

Gly Thr Ser Asn Leu Ala Ser
 1               5

<210> SEQ ID NO 19
<211> LENGTH: 11
<212> TYPE: PRT
<213> ORGANISM: Artificial Sequence
<220> FEATURE:
<223> OTHER INFORMATION: Synthetic Construct

<400> SEQUENCE: 19

Gln Gln Trp Ser Ser Tyr Pro Tyr Met Tyr Thr
1               5                   10

<210> SEQ ID NO 20
<211> LENGTH: 5
<212> TYPE: PRT
<213> ORGANISM: Mus musculus

<400> SEQUENCE: 20

Gly Tyr Phe Met Asn
1               5

<210> SEQ ID NO 21
<211> LENGTH: 17
<212> TYPE: PRT
<213> ORGANISM: Mus musculus

<400> SEQUENCE: 21

Arg Ile Phe Pro Tyr Asn Gly Asp Thr Phe Tyr Asn Gln Lys Phe Lys
1               5                   10                  15

Gly

<210> SEQ ID NO 22
<211> LENGTH: 7
<212> TYPE: PRT
<213> ORGANISM: Mus musculus

<400> SEQUENCE: 22

Gly Thr His Tyr Phe Asp Tyr
1               5

<210> SEQ ID NO 23
<211> LENGTH: 11
<212> TYPE: PRT
<213> ORGANISM: Mus musculus

<400> SEQUENCE: 23

Arg Thr Ser Glu Asn Ile Phe Ser Tyr Leu Ala
1               5                   10

<210> SEQ ID NO 24
<211> LENGTH: 7
<212> TYPE: PRT
<213> ORGANISM: Mus musculus

<400> SEQUENCE: 24

Asn Ala Lys Thr Leu Ala Glu
1               5

<210> SEQ ID NO 25
<211> LENGTH: 9
<212> TYPE: PRT
<213> ORGANISM: Mus musculus

<400> SEQUENCE: 25

Gln His His Tyr Ala Phe Pro Trp Thr
1               5

<210> SEQ ID NO 26
<211> LENGTH: 5
<212> TYPE: PRT
<213> ORGANISM: Artificial Sequence

```
<220> FEATURE:
<223> OTHER INFORMATION: Synthetic Construct

<400> SEQUENCE: 26

Gly Tyr Phe Met Asn
1               5

<210> SEQ ID NO 27
<211> LENGTH: 17
<212> TYPE: PRT
<213> ORGANISM: Artificial Sequence
<220> FEATURE:
<223> OTHER INFORMATION: Synthetic Construct

<400> SEQUENCE: 27

Arg Ile His Pro Tyr Asp Gly Asp Thr Phe Tyr Asn Gln Lys Phe Gln
1               5                   10                  15

Gly

<210> SEQ ID NO 28
<211> LENGTH: 9
<212> TYPE: PRT
<213> ORGANISM: Artificial Sequence
<220> FEATURE:
<223> OTHER INFORMATION: Synthetic Construct

<400> SEQUENCE: 28

Tyr Asp Gly Ser Arg Ala Met Asp Tyr
1               5

<210> SEQ ID NO 29
<211> LENGTH: 15
<212> TYPE: PRT
<213> ORGANISM: Artificial Sequence
<220> FEATURE:
<223> OTHER INFORMATION: Synthetic Construct

<400> SEQUENCE: 29

Lys Ala Ser Gln Ser Val Ser Phe Ala Gly Thr Ser Leu Met His
1               5                   10                  15

<210> SEQ ID NO 30
<211> LENGTH: 7
<212> TYPE: PRT
<213> ORGANISM: Artificial Sequence
<220> FEATURE:
<223> OTHER INFORMATION: Synthetic Construct

<400> SEQUENCE: 30

Arg Ala Ser Asn Leu Glu Ala
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Construct

<400> SEQUENCE: 31

Gln Gln Ser Arg Glu Tyr Pro Tyr Thr
1               5

<210> SEQ ID NO 32
<211> LENGTH: 330
<212> TYPE: PRT
```

<213> ORGANISM: Homo sapiens

<400> SEQUENCE: 32

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 33
<211> LENGTH: 327
<212> TYPE: PRT
<213> ORGANISM: Artificial Sequence
<220> FEATURE:
<223> OTHER INFORMATION: Synthetic Construct

<400> SEQUENCE: 33

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
            325

<210> SEQ ID NO 34
<211> LENGTH: 107
<212> TYPE: PRT
<213> ORGANISM: Homo sapiens

<400> SEQUENCE: 34

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser

```
                    50                  55                  60
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105
```

<210> SEQ ID NO 35
<211> LENGTH: 257
<212> TYPE: PRT
<213> ORGANISM: Homo sapiens

<400> SEQUENCE: 35

```
Met Ala Gln Arg Met Thr Thr Gln Leu Leu Leu Leu Leu Val Trp Val
 1               5                  10                  15

Ala Val Val Gly Glu Ala Gln Thr Arg Ile Ala Trp Ala Arg Thr Glu
                20                  25                  30

Leu Leu Asn Val Cys Met Asn Ala Lys His His Lys Glu Lys Pro Gly
            35                  40                  45

Pro Glu Asp Lys Leu His Glu Gln Cys Arg Pro Trp Arg Lys Asn Ala
        50                  55                  60

Cys Cys Ser Thr Asn Thr Ser Gln Glu Ala His Lys Asp Val Ser Tyr
 65                  70                  75                  80

Leu Tyr Arg Phe Asn Trp Asn His Cys Gly Glu Met Ala Pro Ala Cys
                85                  90                  95

Lys Arg His Phe Ile Gln Asp Thr Cys Leu Tyr Glu Cys Ser Pro Asn
            100                 105                 110

Leu Gly Pro Trp Ile Gln Gln Val Asp Gln Ser Trp Arg Lys Glu Arg
        115                 120                 125

Val Leu Asn Val Pro Leu Cys Lys Glu Asp Cys Glu Gln Trp Trp Glu
130                 135                 140

Asp Cys Arg Thr Ser Tyr Thr Cys Lys Ser Asn Trp His Lys Gly Trp
145                 150                 155                 160

Asn Trp Thr Ser Gly Phe Asn Lys Cys Ala Val Gly Ala Ala Cys Gln
                165                 170                 175

Pro Phe His Phe Tyr Phe Pro Thr Pro Thr Val Leu Cys Asn Glu Ile
            180                 185                 190

Trp Thr His Ser Tyr Lys Val Ser Asn Tyr Ser Arg Gly Ser Gly Arg
        195                 200                 205

Cys Ile Gln Met Trp Phe Asp Pro Ala Gln Gly Asn Pro Asn Glu Glu
    210                 215                 220

Val Ala Arg Phe Tyr Ala Ala Met Ser Gly Ala Gly Pro Trp Ala Ala
225                 230                 235                 240

Ala Trp Pro Phe Leu Leu Ser Leu Ala Leu Met Leu Leu Trp Leu Leu
                245                 250                 255

Ser
```

<210> SEQ ID NO 36
<211> LENGTH: 25
<212> TYPE: PRT
<213> ORGANISM: Artificial Sequence
<220> FEATURE:
<223> OTHER INFORMATION: Synthetic Construct

<400> SEQUENCE: 36

Gly Cys Leu Val Lys Asp Tyr Phe Pro Glu Pro Val Cys Val Ser Trp
1               5                   10                  15

Asn Ser Gly Ala Leu Thr Ser Gly Val
            20                  25

<210> SEQ ID NO 37
<211> LENGTH: 25
<212> TYPE: PRT
<213> ORGANISM: Artificial Sequence
<220> FEATURE:
<223> OTHER INFORMATION: Synthetic Construct

<400> SEQUENCE: 37

Leu Val Lys Asp Tyr Phe Pro Glu Pro Val Thr Val Cys Trp Asn Ser
1               5                   10                  15

Gly Ala Leu Thr Ser Gly Val His Thr
            20                  25

<210> SEQ ID NO 38
<211> LENGTH: 25
<212> TYPE: PRT
<213> ORGANISM: Artificial Sequence
<220> FEATURE:
<223> OTHER INFORMATION: Synthetic Construct

<400> SEQUENCE: 38

Pro Val Thr Val Ser Trp Asn Ser Gly Ala Leu Thr Cys Gly Val His
1               5                   10                  15

Thr Phe Pro Ala Val Leu Gln Ser Ser
            20                  25

<210> SEQ ID NO 39
<211> LENGTH: 25
<212> TYPE: PRT
<213> ORGANISM: Artificial Sequence
<220> FEATURE:
<223> OTHER INFORMATION: Synthetic Construct

<400> SEQUENCE: 39

Ser Trp Asn Ser Gly Ala Leu Thr Ser Gly Val His Cys Phe Pro Ala
1               5                   10                  15

Val Leu Gln Ser Ser Gly Leu Tyr Ser
            20                  25

<210> SEQ ID NO 40
<211> LENGTH: 25
<212> TYPE: PRT
<213> ORGANISM: Artificial Sequence
<220> FEATURE:
<223> OTHER INFORMATION: Synthetic Construct

<400> SEQUENCE: 40

Val Val Thr Val Pro Ser Ser Ser Leu Gly Thr Gln Cys Tyr Ile Cys
1               5                   10                  15

Asn Val Asn His Lys Pro Ser Asn Thr
            20                  25

<210> SEQ ID NO 41
<211> LENGTH: 25
<212> TYPE: PRT
<213> ORGANISM: Artificial Sequence
<220> FEATURE:
<223> OTHER INFORMATION: Synthetic Construct

<400> SEQUENCE: 41

Val Val Thr Val Pro Ser Ser Asn Phe Gly Thr Gln Cys Tyr Thr Cys
1               5                   10                  15

Asn Val Asp His Lys Pro Ser Asn Thr
            20                  25

<210> SEQ ID NO 42
<211> LENGTH: 25
<212> TYPE: PRT
<213> ORGANISM: Artificial Sequence
<220> FEATURE:
<223> OTHER INFORMATION: Synthetic Construct

<400> SEQUENCE: 42

Val Val Thr Val Pro Ser Ser Leu Gly Thr Gln Cys Tyr Thr Cys
1               5                   10                  15

Asn Val Asn His Lys Pro Ser Asn Thr
            20                  25

<210> SEQ ID NO 43
<211> LENGTH: 25
<212> TYPE: PRT
<213> ORGANISM: Artificial Sequence
<220> FEATURE:
<223> OTHER INFORMATION: Synthetic Construct

<400> SEQUENCE: 43

Val Val Thr Val Pro Ser Ser Leu Gly Thr Lys Cys Tyr Thr Cys
1               5                   10                  15

Asn Val Asp His Lys Pro Ser Asn Thr
            20                  25

<210> SEQ ID NO 44
<211> LENGTH: 25
<212> TYPE: PRT
<213> ORGANISM: Artificial Sequence
<220> FEATURE:
<223> OTHER INFORMATION: Synthetic Construct

<400> SEQUENCE: 44

Val Val Thr Val Pro Ser Ser Leu Gly Thr Gln Thr Tyr Cys Cys
1               5                   10                  15

Asn Val Asn His Lys Pro Ser Asn Thr
            20                  25

<210> SEQ ID NO 45
<211> LENGTH: 25
<212> TYPE: PRT
<213> ORGANISM: Artificial Sequence
<220> FEATURE:
<223> OTHER INFORMATION: Synthetic Construct

<400> SEQUENCE: 45

Val Val Thr Val Pro Ser Ser Asn Phe Gly Thr Gln Thr Tyr Cys Cys
1               5                   10                  15

Asn Val Asp His Lys Pro Ser Asn Thr
            20                  25

<210> SEQ ID NO 46
<211> LENGTH: 25
<212> TYPE: PRT
<213> ORGANISM: Artificial Sequence
<220> FEATURE:
<223> OTHER INFORMATION: Synthetic Construct

```
<400> SEQUENCE: 46

Val Val Thr Val Pro Ser Ser Ser Leu Gly Thr Gln Thr Tyr Cys Cys
1               5                   10                  15

Asn Val Asn His Lys Pro Ser Asn Thr
            20                  25

<210> SEQ ID NO 47
<211> LENGTH: 25
<212> TYPE: PRT
<213> ORGANISM: Artificial Sequence
<220> FEATURE:
<223> OTHER INFORMATION: Synthetic Construct

<400> SEQUENCE: 47

Val Val Thr Val Pro Ser Ser Ser Leu Gly Thr Lys Thr Tyr Cys Cys
1               5                   10                  15

Asn Val Asp His Lys Pro Ser Asn Thr
            20                  25

<210> SEQ ID NO 48
<211> LENGTH: 18
<212> TYPE: PRT
<213> ORGANISM: Artificial Sequence
<220> FEATURE:
<223> OTHER INFORMATION: Synthetic Construct

<400> SEQUENCE: 48

Glu Ala Leu His Asn His Tyr Thr Gln Lys Ser Leu Cys Leu Ser Pro
1               5                   10                  15

Gly Lys

<210> SEQ ID NO 49
<211> LENGTH: 18
<212> TYPE: PRT
<213> ORGANISM: Artificial Sequence
<220> FEATURE:
<223> OTHER INFORMATION: Synthetic Construct

<400> SEQUENCE: 49

Glu Ala Leu His Asn Arg Phe Thr Gln Lys Ser Leu Cys Leu Ser Pro
1               5                   10                  15

Gly Lys

<210> SEQ ID NO 50
<211> LENGTH: 18
<212> TYPE: PRT
<213> ORGANISM: Artificial Sequence
<220> FEATURE:
<223> OTHER INFORMATION: Synthetic Construct

<400> SEQUENCE: 50

Glu Ala Leu His Asn His Tyr Thr Gln Lys Ser Leu Cys Leu Ser Leu
1               5                   10                  15

Gly Lys

<210> SEQ ID NO 51
<211> LENGTH: 20
<212> TYPE: PRT
<213> ORGANISM: Artificial Sequence
<220> FEATURE:
<223> OTHER INFORMATION: Synthetic Construct

<400> SEQUENCE: 51
```

```
Glu Val Thr His Gln Gly Cys Ser Ser Pro Val Thr Lys Ser Phe Asn
1               5                   10                  15

Arg Gly Glu Cys
            20

<210> SEQ ID NO 52
<211> LENGTH: 20
<212> TYPE: PRT
<213> ORGANISM: Artificial Sequence
<220> FEATURE:
<223> OTHER INFORMATION: Synthetic Construct

<400> SEQUENCE: 52

Glu Val Thr His Gln Gly Leu Ser Ser Pro Val Cys Lys Ser Phe Asn
1               5                   10                  15

Arg Gly Glu Cys
            20

<210> SEQ ID NO 53
<211> LENGTH: 20
<212> TYPE: PRT
<213> ORGANISM: Artificial Sequence
<220> FEATURE:
<223> OTHER INFORMATION: Synthetic Construct

<400> SEQUENCE: 53

Glu Val Thr His Gln Gly Leu Ser Ser Pro Cys Thr Lys Ser Phe Asn
1               5                   10                  15

Arg Gly Glu Cys
            20
```

ANTI-FOLATE RECEPTOR ALPHA (FRA) ANTIBODY-DRUG CONJUGATES AND METHODS OF USING THEREOF

CROSS-REFERENCE TO RELATED APPLICATIONS

This application claims the priority benefit of U.S. Provisional Application No. 62/015,321, filed on Jun. 20, 2014, which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 606592001000SEQLIST.TXT, date recorded: Jun. 16, 2015, size: 44 KB).

FIELD OF INVENTION

The invention is in the field of cancer therapeutics, and provides efficacy and specificity for the delivery of cytotoxic drugs specifically to cancer cells through an antibody-drug conjugate (ADC) format.

BACKGROUND

Antibody-drug conjugates (ADCs) are a class of therapeutics that combines the specificity of monoclonal antibodies (mAbs) with the potency of cytotoxic molecules. The use of ADC empowers the cancer killing activity of antibody by conjugated cytotoxic agents, while target-specific delivery avoids systemic toxicity caused by exposure to free toxic agents. As of May 2014, two ADCs have been approved by FDA for treating human cancers. Adcetris (Brentuximab vedotin or SGN-35), an anti-CD30 antibody conjugated with cytotoxic agent MMAE, is designed to treat CD30-positive relapsing lymphoma. Kadcyla (T-DM1), an anti-HER2 antibody conjugated with cytotoxic agent DM1, is designed to treat HER2-positive metastatic breast cancer.

The linker technology profoundly impacts ADC potency, specificity, and safety. Enzyme-labile linkers utilize the differential activities of proteases inside and outside of the cells to achieve control of the drug release. A drug can be conjugated to antibody via peptide bond, and can only be specifically cleaved by the action of lysosomal proteases present inside the cells, and at elevated levels in certain tumor types (Koblinski et al (2000) Clin. Chem. Acta 291:113-135). This ensures the stability of linker in the blood stream to limit the damage to healthy tissue. However, the increased hydrophobicity of some enzyme-labile linkers can lead to aggregation of ADC, particularly with strongly hydrophobic drugs. A hydrophilic self-immolative linker may provide better serum stability via specific enzyme-labile design, as well as achieve better efficacy via bystander effect on the heterogeneous cancer cells.

Folate receptor alpha (FRA), a membrane protein, which binds folic acid with high affinity and mediates the cellular uptake of folate via receptor-mediated endocytosis (Leamon et al., 1991, PNAS 88:5572-5576). Overexpression of FRA was found in 90% epithelial ovarian cancers, as well as numerous other cancers including endometrial cancer, kidney cancer, lung cancer, mesothelioma, breast cancer, brain cancer, and myeloid leukemia, whereas most normal tissues express low to negligible levels (Coney et al., 1991, Cancer Res. 51:6125-6132). The differential expression profiles of FRA in cancer versus normal tissues warrant the development of Ab-based therapeutics. A humanized form of the murine monoclonal anti-FRA antibody was shown effective in preclinical studies (Ebel et al., 2007, Cancer Immun 7:1-8), and is currently being evaluated in patients with FRA expressing tumors (Kalli et al., 2007, Curr Opin Investig 8:1067-1073). Furthermore, the ability of FRA to mediate endocytosis makes it an attractive candidate for the development of cancer-targeting ADC. To date, various drug conjugates and anti-FRA antibodies are being tested in clinical trials and have demonstrated safety (Xia et al., 2010, J Med Chem. 53:6811-6824; Zacchetti et al., 2009, Nucl Med Biol. 36: 759-770).

There is a need for anti-cancer therapeutics having improved efficacy that can deliver cytotoxic drugs to cancer cells through an antibody-drug conjugate (ADC) format.

SUMMARY

The compounds of the present disclosure comprise a drug moiety, a targeting moiety which is an antibody capable of targeting a selected cell population (such as a cell population expressing folate receptor alpha (FRA)), and a linker which contains an acyl unit, an optional spacer unit for providing distance between the drug moiety and the targeting moiety (such as an anti-FRA antibody), a peptide linker which can be cleavable under appropriate conditions, a hydrophilic self-immolative linker, and an optional second self-immolative spacer or cyclization self-elimination linker.

The present disclosure provides a compound of the formula (I):

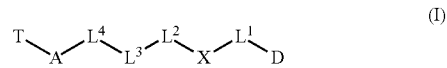

or a salt or solvate or stereoisomer thereof;

wherein:

D is a drug moiety;

T is a targeting moiety which is an antibody that specifically binds to a folate receptor alpha (FRA) (e.g., a human FRA);

X is a hydrophilic self-immolative linker;

$L^1$ is a bond, a second self-immolative linker, or a cyclization self-elimination linker;

$L^2$ is a bond or a second self-immolative linker;

wherein if $L^1$ is a second self-immolative linker or a cyclization self-elimination linker, then $L^2$ is a bond;

wherein if $L^2$ is a second self-immolative linker, then $L^1$ is a bond;

$L^3$ is a peptide linker;

$L^4$ is a bond or a spacer; and

A is an acyl unit.

The present disclosure provides a compound of the formula (II):

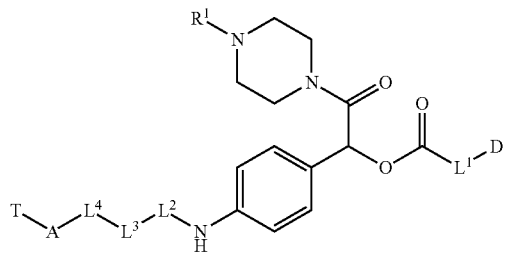

(II)

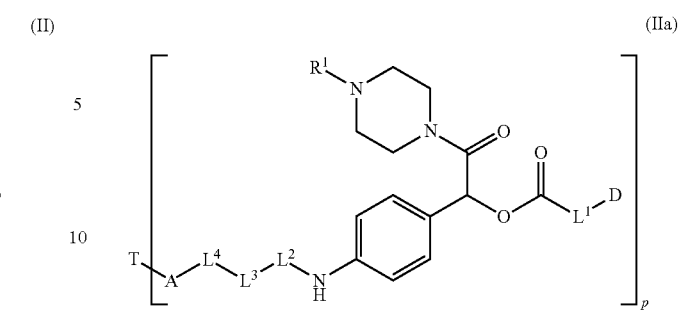

(IIa)

or a salt or solvate or stereoisomer thereof;
wherein:
D is a drug moiety;
T is a targeting moiety which is an antibody that specifically binds to a folate receptor alpha (FRA) (e.g., a human FRA);
$R^1$ is hydrogen, unsubstituted or substituted $C_{1-3}$ alkyl, or unsubstituted or substituted heterocyclyl;
$L^1$ is a bond, a second self-immolative linker, or a cyclization self-elimination linker;
$L^2$ is a bond or a second self-immolative linker;
  wherein if $L^1$ is a second self-immolative linker or a cyclization self-elimination linker, then $L^2$ is a bond;
  wherein if $L^2$ is a second self-immolative linker, then $L^1$ is a bond;
$L^3$ is a peptide linker;
$L^4$ is a bond or a spacer; and
A is an acyl unit.

The present disclosure provides a compound of the formula (Ia):

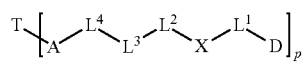

(Ia)

or a salt or solvate or stereoisomer thereof;
wherein:
p is 1 to 20;
D is a drug moiety;
T is a targeting moiety which is an antibody that specifically binds to a folate receptor alpha (FRA) (e.g., a human FRA);
X is a hydrophilic self-immolative linker;
$L^1$ is a bond, a second self-immolative linker, or a cyclization self-elimination linker;
$L^2$ is a bond or a second self-immolative linker;
  wherein if $L^1$ is a second self-immolative linker or a cyclization self-elimination linker, then $L^2$ is a bond;
  wherein if $L^2$ is a second self-immolative linker, then $L^1$ is a bond;
$L^3$ is a peptide linker;
$L^4$ is a bond or a spacer; and
A is an acyl unit.

The present disclosure provides a compound of the formula (IIa):

or a salt or solvate or stereoisomer thereof;
wherein:
p is 1 to 20;
D is a drug moiety;
T is a targeting moiety which is an antibody that specifically binds to a folate receptor alpha (FRA) (e.g., a human FRA);
$R^1$ is hydrogen, unsubstituted or substituted $C_{1-3}$ alkyl, or unsubstituted or substituted heterocyclyl;
$L^1$ is a bond, a second self-immolative linker, or a cyclization self-elimination linker;
$L^2$ is a bond or a second self-immolative linker;
  wherein if $L^1$ is a second self-immolative linker or a cyclization self-elimination linker, then $L^2$ is a bond;
  wherein if $L^2$ is a second self-immolative linker, then $L^1$ is a bond;
$L^3$ is a peptide linker;
$L^4$ is a bond or a spacer; and
A is an acyl unit.

In certain embodiments of the compounds above, p is 1 to 4. In certain embodiments, $L^1$ is a bond. In certain embodiments, $L^1$ is a second self-immolative linker or a cyclization self-elimination linker. In certain embodiments, $L^1$ is an aminobenzyloxycarbonyl linker. In certain embodiments, $L^1$ is selected from the group consisting of

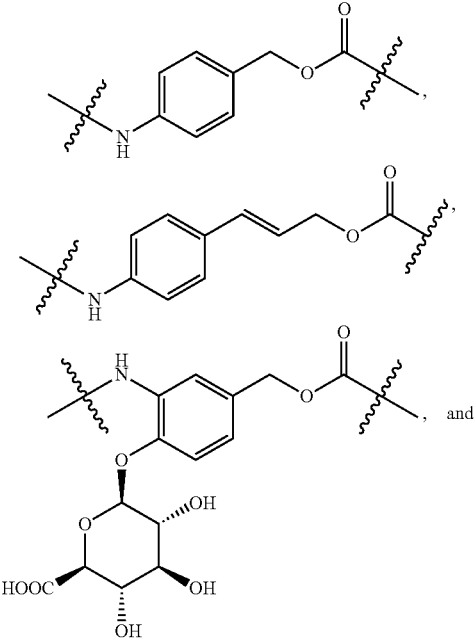

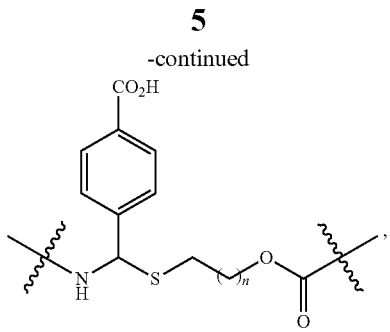

wherein n is 1 or 2.

In certain embodiments, $L^1$ is selected from the group consisting of

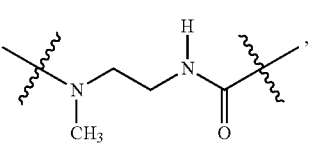

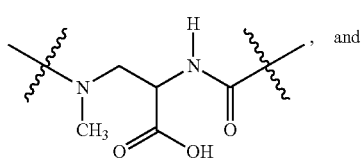, and

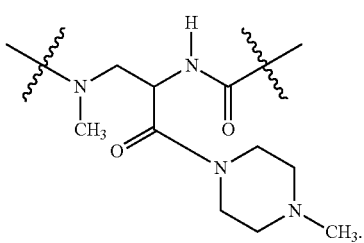

In certain embodiments of the compounds above, $L^2$ is a bond. In certain embodiments, $L^2$ is a second self-immolative linker. In certain embodiments, $L^2$ is an aminobenzyloxycarbonyl linker. In certain embodiments, $L^2$ is selected from

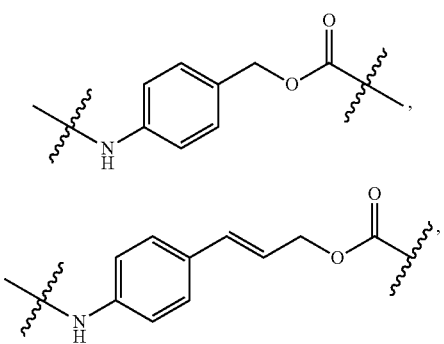

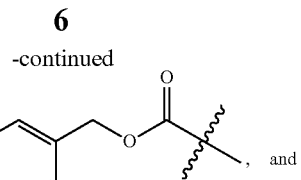, and

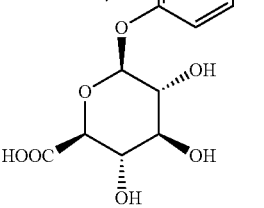

wherein n is 1 or 2.

In certain embodiments of the compounds above, $L^3$ is a peptide linker of 1 to 10 amino acid residues. In certain embodiments, $L^3$ is a peptide linker of 2 to 4 amino acid residues. In certain embodiments, $L^3$ is a peptide linker comprising at least one lysine or arginine residue. In certain embodiments, $L^3$ is a peptide linker comprising an amino acid residue selected from lysine, D-lysine, citrulline, arginine, proline, histidine, ornithine and glutamine. In certain embodiments, $L^3$ is a peptide linker comprising an amino acid residue selected from valine, isoleucine, phenylalanine, methionine, asparagine, proline, alanine, leucine, tryptophan, and tyrosine. In certain embodiments, $L^3$ is a dipeptide unit selected from valine-citrulline, proline-lysine, methionine-D-lysine, asparagine-D-lysine, isoleucine-proline, phenylalanine-lysine, and valine-lysine. In certain embodiments, $L^3$ is valine-citrulline.

In certain embodiments of the compounds above, $L^4$ is a bond. In certain embodiments, $L^4$ is a spacer. In certain embodiments, the spacer is polyalkylene glycol, alkylene, alkenylene, alkynylene, or polyamine. In certain embodiments, $L^4$ is $L^{4a}$-C(O), $L^{4a}$-C(O)—NH, $L^{4a}$-S(O)$_2$, or $L^{4a}$-S(O)$_2$—NH, wherein each $L^{4a}$ is independently polyalkylene glycol, alkylene, alkenylene, alkynylene, or polyamine. In certain embodiments, $L^4$ is $L^{4a}$-C(O), wherein $L^{4a}$ is polyalkylene glycol, alkylene, alkenylene, alkynylene, or polyamine. In certain embodiments, $L^4$ is $L^{4a}$-C(O), wherein $L^{4a}$ is a polyalkylene glycol. In certain embodiments, $L^4$ is $L^{4a}$-C(O), wherein $L^{4a}$ is a polyethylene glycol. In certain embodiments, the spacer is of the formula —CH$_2$—(CH$_2$—O—CH$_2$)$_m$—CH$_2$—C(O)—, wherein m is an integer from 0 to 30. In certain embodiments, $L^4$ is $L^{4a}$-C(O), wherein $L^{4a}$ is alkylene.

In certain embodiments of the compounds above, A is selected from the group consisting of

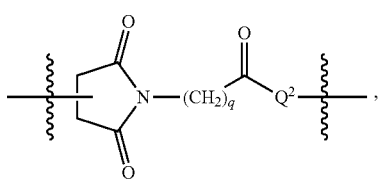

-continued

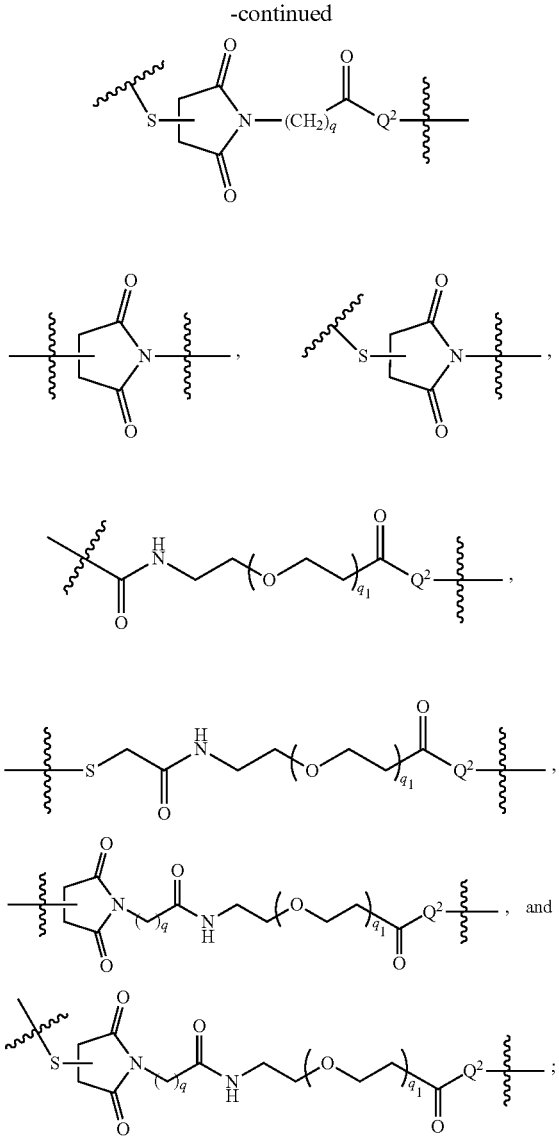

wherein each $Q^2$ is NH or O, each q is independently an integer from 1 to 10, and each $q_1$ is independently an integer from 1 to 10. In certain embodiments, q is 2, 3, 4, or 5. In certain embodiments, $q_1$ is 2, 3, 4, or 5. In certain embodiments, A is selected from the group consisting of wherein each $Q^2$ is independently NH or O and each q is independently an integer from 1 to 10. In certain embodiments, q is 2, 3, 4, or 5. In certain embodiments, A is selected from the group consisting of

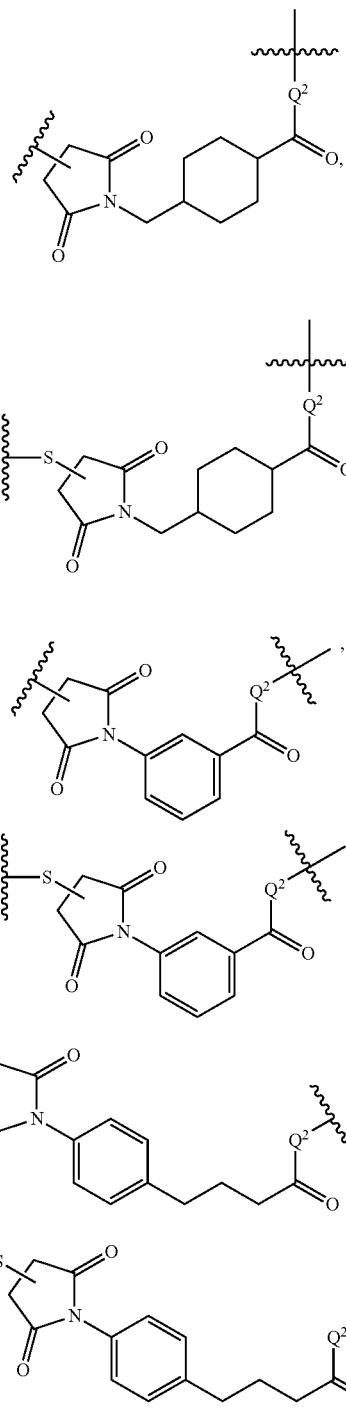

wherein each $Q^2$ is independently NH or O.

In certain embodiments of the compounds above, one or more amino acid residues of a heavy chain of the anti-folate receptor alpha (FRA) antibody are replaced with one or more cysteine residues. In certain embodiments, the antibody comprises a heavy chain constant region (e.g., a heavy chain constant region of a human IgG), wherein one or more amino acid residues in the heavy chain constant region (e.g., CH1, CH2, or CH3) are replaced with one or more cysteine residues. In certain embodiments, the antibody comprises a heavy chain constant region (e.g., a heavy chain constant region of a human IgG), wherein one or more amino acid residues selected from positions 155, 157, 165, 169, 197, 199, and 442 in the heavy chain constant region are replaced with one or more cysteine residues, wherein the numbering is according to the EU index of Kabat. In certain embodiments, the antibody comprises a heavy chain constant region of human IgG1, human IgG2, human IgG3, human IgG4 or human IgG4p, wherein one or more amino acid residues selected from positions 155, 157, 165, 169, 197, 199, and 442 in the heavy chain constant region are replaced with one or more cysteine residues, wherein the numbering is according to the EU index of Kabat. In certain embodiments, the antibody comprises a heavy chain constant region comprising the amino acid sequence of SEQ ID NO:32 and SEQ ID NO:33, wherein one or more amino acid residues selected from positions 155, 157, 165, 169, 197, 199, and 442 in the heavy chain constant region are replaced with one or more cysteine residues, wherein the numbering is according to the EU index of Kabat.

In certain embodiments of the compounds above, one or more amino acid residues of a light chain of the anti-folate receptor alpha (FRA) antibody are replaced with cysteine residues. In certain embodiments, the antibody comprises a light chain constant region (e.g., a human kappa light chain constant region), wherein one or more amino acid residues in the light chain constant region of the antibody are replaced with one or more cysteine residues. In certain embodiments, the antibody comprises a light chain constant region, wherein one or more amino acid residues selected from positions 201 and 206 in the light chain constant region are replaced with one or more cysteine residues, wherein the numbering is according to the EU index of Kabat. In certain embodiments, the antibody comprises a light chain constant region (such as kappa light chain constant region) of human IgG1, human IgG2, human IgG3, human IgG4 or human IgG4p, wherein one or more amino acid residues selected from positions 201 and 206 in the light chain constant region are replaced with one or more cysteine residues, and wherein the numbering is according to the EU index of Kabat. In certain embodiments, the antibody comprises a light chain constant region comprising the amino acid sequence of SEQ ID NO:34, wherein one or more amino acid residues selected from positions 201 and 206 in the light chain constant region are replaced with one or more cysteine residues, wherein the numbering is according to the EU index of Kabat.

In certain embodiments of the compounds above, D is linked to T by way of (or via) the added cysteine residue. In some embodiments, D is linked to T via the thiol group of the added cysteine residue connected through the linker moiety (-A-$L^4$-$L^3$-$L^2$-X-$L^1$-). In certain embodiments, D is an amino-containing drug moiety, wherein the drug is connected to $L^1$ or X through the amino group. In certain embodiments, D is duocarmycin, dolastatin, tubulysin, doxorubicin (DOX), paclitaxel, or mitomycin C (MMC), or an amino derivative thereof. In certain embodiments, D is an amino derivative of duocarmycin selected from the group consisting of

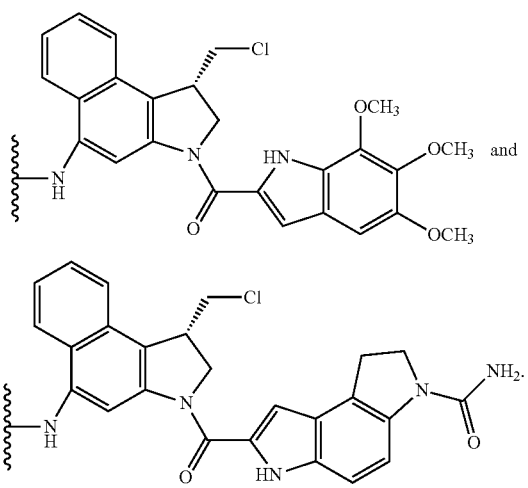

In certain embodiments, D is an amino derivative of dolastatin (e.g., monomethyl Dolastatin 10):

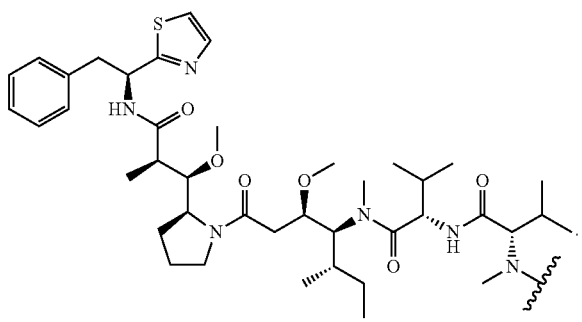 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)c1nccs1)OC)C(C)C)C(C)C]

In certain embodiments, -A-$L^4$-$L^3$-$L^2$- is

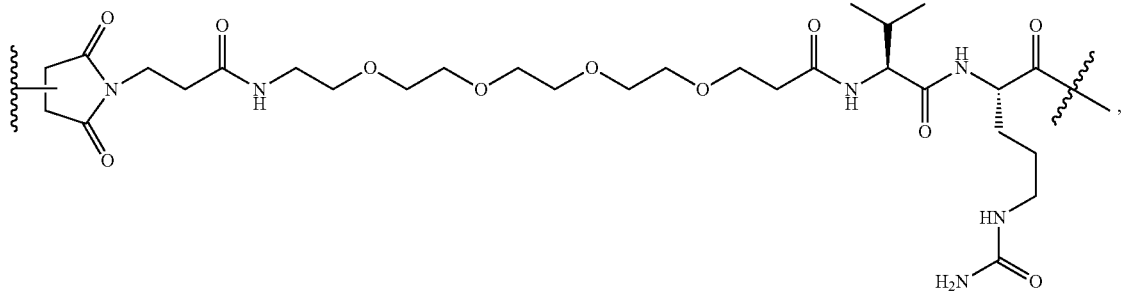

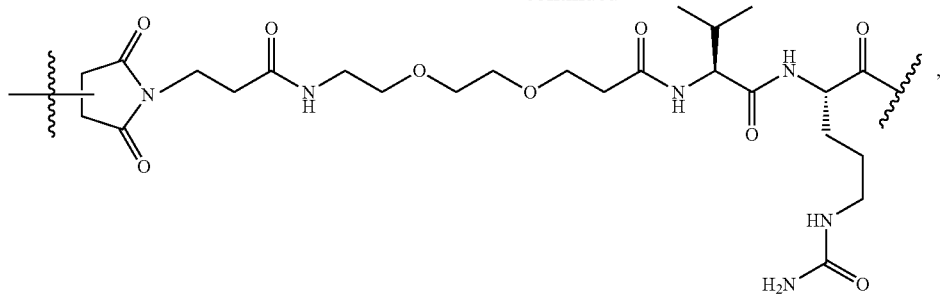
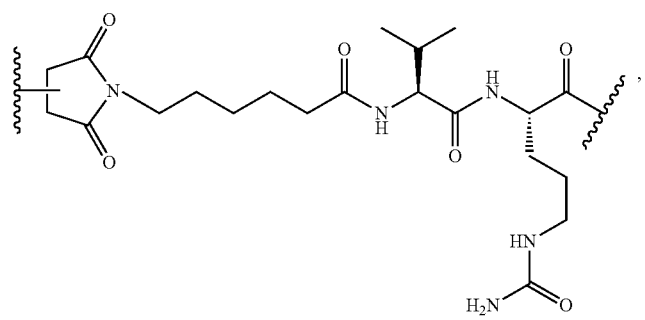
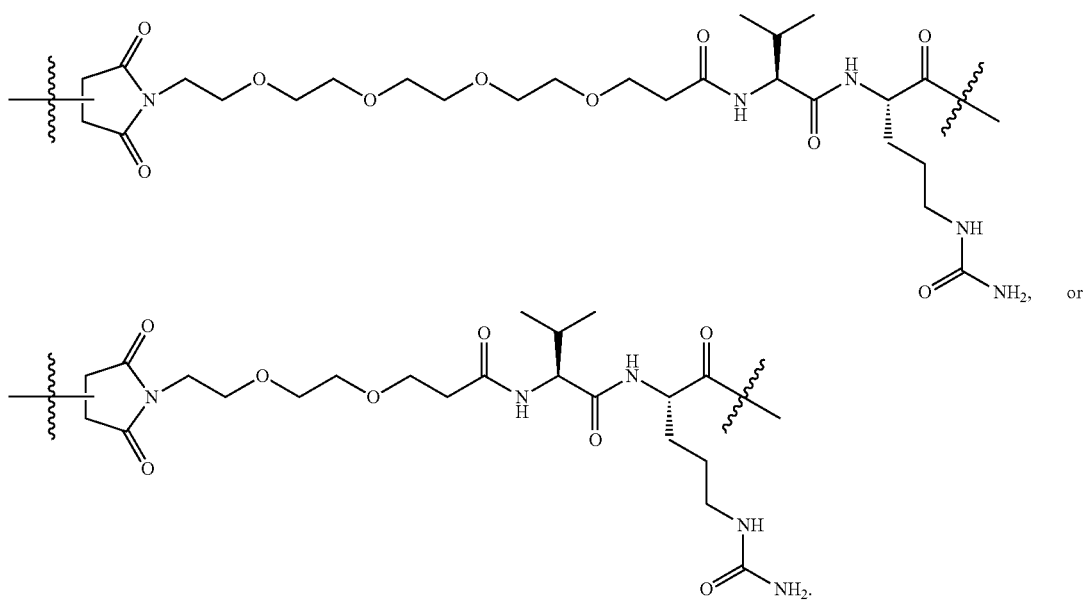
In certain embodiments, -A-L$^4$-L$^3$-L$^2$-X-L$^1$-D is:
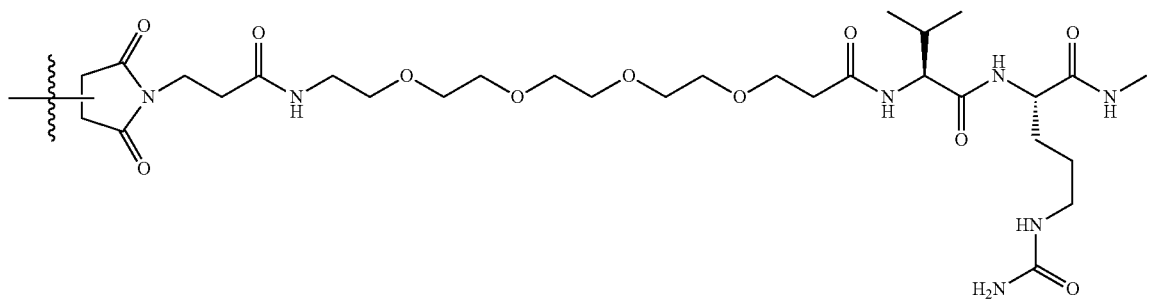

-continued

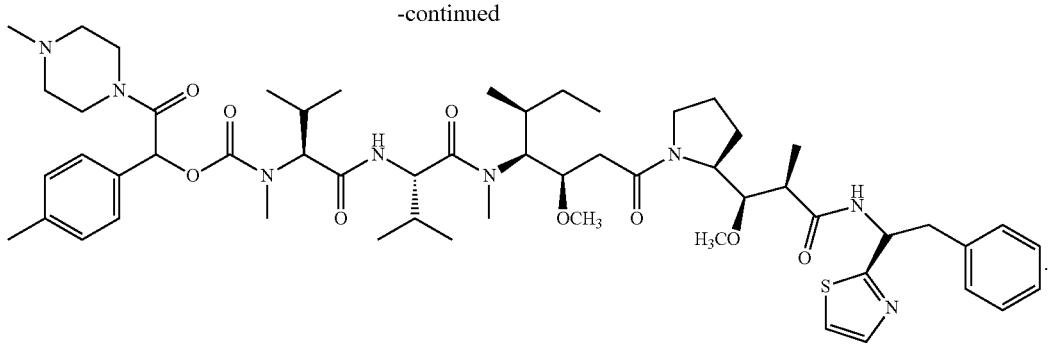

In certain embodiments, -A-L$^4$-L$^3$-L$^2$-X-L$^1$-D is:

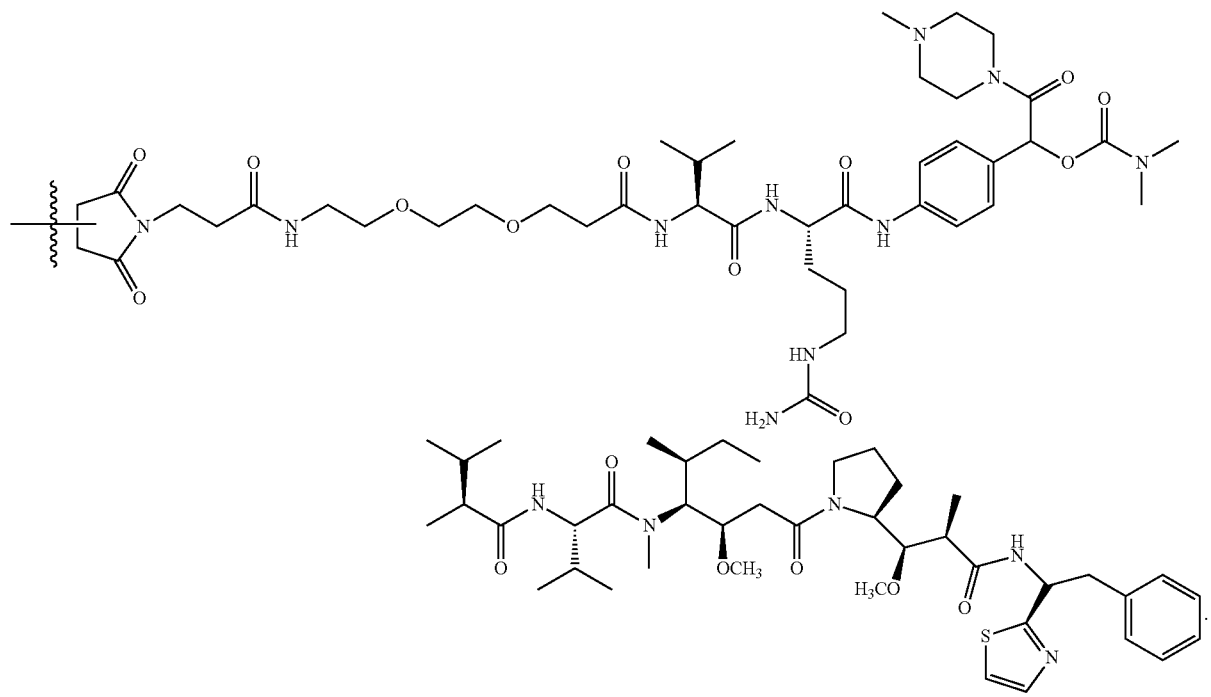

In certain embodiments, -A-L$^4$-L$^3$-L$^2$-X-L$^1$-D is:

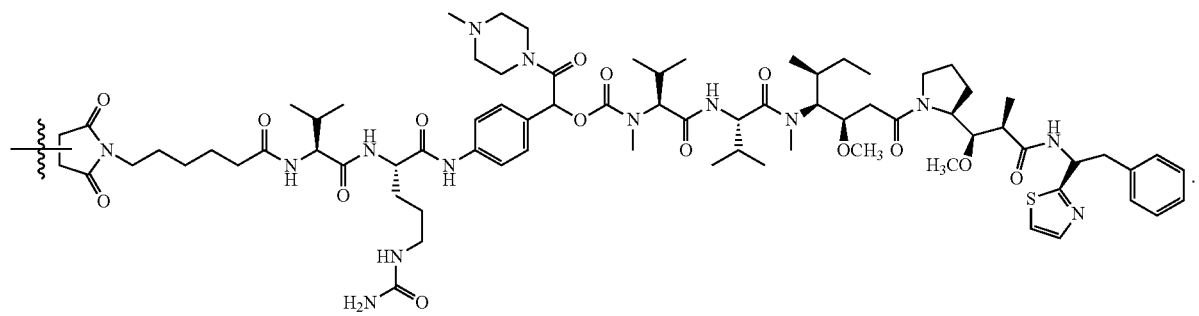

In certain embodiments of the compounds above, the anti-folate receptor alpha (FRA) antibody is a humanized antibody, a chimeric antibody or a human antibody.

In certain embodiments, the anti-folate receptor alpha (FRA) antibody comprises a heavy chain variable region and a light chain variable region, wherein:

(1) the heavy chain variable region comprises the three heavy chain HVRs (e.g., SEQ ID NOs: 14, 15, and 16) of antibody hLK26 and/or the light chain variable region comprises the three light chain HVRs (e.g., SEQ ID NOs: 17, 18, and 19) of antibody hLK26;
(2) the heavy chain variable region comprises the three heavy chain HVRs (e.g., SEQ ID NOs: 20, 21, and 22) of antibody 26B3 and/or the light chain variable region comprises the three light chain HVRs (e.g., SEQ ID NOs: 23, 24 and 25) of antibody 26B3; or
(3) the heavy chain variable region comprises the three heavy chain HVRs (e.g., SEQ ID NOs: 26, 27, and 28) of antibody hMov19 and/or the light chain variable region comprises the three light chain HVRs (e.g., SEQ ID NOs: 29, 30, and 31) of antibody hMov19.

In certain embodiments, the anti-folate receptor alpha (FRA) antibody comprises a heavy chain variable region and a light chain variable region, wherein:
(1) the heavy chain variable region comprises the three heavy chain HVRs (e.g., SEQ ID NOs: 14, 15, and 16) of the amino acid sequence of SEQ ID NO:8 and/or the light chain variable region comprises the three light chain HVRs (e.g., SEQ ID NOs: 17, 18, and 19) of the amino acid sequence of SEQ ID NO:9;
(2) the heavy chain variable region comprises the three heavy chain HVRs (e.g., SEQ ID NOs: 20, 21, and 22) of the amino acid sequence of SEQ ID NO:10 and/or the light chain variable region comprises the three light chain HVRs (e.g., SEQ ID NOs: 23, 24 and 25) of the amino acid sequence of SEQ ID NO:11; or
(3) the heavy chain variable region comprises the three heavy chain HVRs (e.g., SEQ ID NOs: 26, 27, and 28) of the amino acid sequence of SEQ ID NO:12 and/or the light chain variable region comprises the three light chain HVRs (e.g., SEQ ID NOs: 29, 30, and 31) of the amino acid sequence of SEQ ID NO:13.

In certain embodiments, the anti-folate receptor alpha (FRA) antibody comprises a heavy chain variable region and a light chain variable region, wherein
(1) the heavy chain variable region comprises the amino acid sequence of SEQ ID NO:8 and/or the light chain variable region comprising the amino acid sequence of SEQ ID NO:9;
(2) the heavy chain variable region comprises the amino acid sequence of SEQ ID NO:10 and/or the light chain variable region comprising the amino acid sequence of SEQ ID NO:11; or
(3) the heavy chain variable region comprises the amino acid sequence of SEQ ID NO:12 and/or the light chain variable region comprising the amino acid sequence of SEQ ID NO:13.

In certain embodiments, the anti-folate receptor alpha (FRA) antibody comprises a heavy chain and a light chain, wherein
(1) the heavy chain comprises the amino acid sequence of SEQ ID NO: 1 and/or the light chain comprises the amino acid sequence of SEQ ID NO: 3;
(2) the heavy chain comprises the amino acid sequence of SEQ ID NO: 2 and/or the light chain comprises the amino acid sequence of SEQ ID NO: 3;
(3) the heavy chain comprises a variable region comprising the amino acid sequence of SEQ ID NO: 10 and a constant region comprising the amino acid sequence of SEQ ID NO: 32 or 33 and/or the light chain comprises a variable region comprising the amino acid sequence of SEQ ID NO: 11 and a constant region comprising the amino acid sequence of SEQ ID NO: 34; or
(4) the heavy chain comprises the amino acid sequence of SEQ ID NO: 6 and/or the light chain comprises the amino acid sequence of SEQ ID NO: 7.

In certain embodiments, the antibody comprises a human heavy chain constant region comprising the amino acid sequence of SEQ ID NO:32 or SEQ ID NO:33 and a human kappa light chain constant region comprising the amino acid sequence of SEQ ID NO:34, wherein one or more amino acid residues selected from T155, S157, S165, T169, T197, T199, and S442 in the heavy chain constant region, and/or one or more amino acid residues selected from L201 and T206 in the light chain constant region are replaced with a cysteine residue, and wherein the numbering is according to the EU index of Kabat. In some of these embodiments, at least one (e.g., one) amino acid residue selected from T155, S157, S165, T169, T197, T199, and S442 in the heavy chain constant region, and/or at least one (e.g., one) amino acid residues selected from L201 and T206 in the light chain constant region is replaced with a cysteine residue. In certain embodiments, the antibody is an antigen-binding fragment selected from the group consisting of Fab, Fab', F(ab')$_2$, Fv, and ScFv.

The present disclosure provides a pharmaceutical composition comprising a compound described above and herein, or a salt or solvate or stereoisomer thereof; and a pharmaceutically acceptable carrier.

The present disclosure provides a method of killing a cell that expresses a human folate receptor alpha (FRA), comprising administering to the cell an amount of a compound described herein, or a salt or solvate or stereoisomer thereof, sufficient to kill the cell. In certain embodiments, the cell is a cancer cell. In certain embodiments, the cancer cell in is an individual (e.g., a human). In certain embodiments, the cancer cell is a lymphoma or leukemia cell. In certain embodiments, the cancer cell is a folate receptor alpha (FRA)-positive lymphoma or folate receptor alpha (FRA)-positive leukemia cell.

The present disclosure provides a method of treating cancer in an individual comprising administering to the individual an effective amount of a compound described herein, or a salt or solvate or stereoisomer thereof. In certain embodiments, the individual has cancer or has been diagnosed with cancer. In certain embodiments, the cancer is ovarian cancer, lung cancer, uterine cancer, testicular choriocarcinoma, ependymoma, mesothelioma, breast cancer, colon cancer, or renal cell carcinoma. In some embodiments, the cancer is a folate receptor alpha (FRA)-positive cancer. In certain embodiments, the individual is a human.

The present disclosure provides a kit comprising a compound described herein, or a salt or solvate or stereoisomer thereof. In certain embodiments, the kit further comprises instructions for use in the treatment of cancer.

Provided herein is a process for making a compound of formula (II):

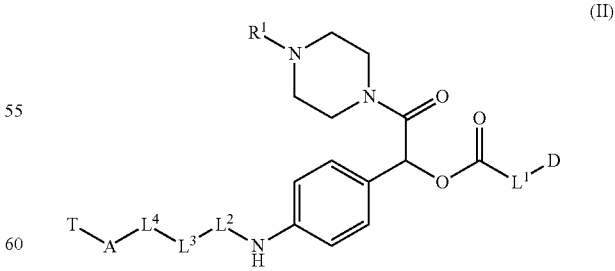

(II)

or a salt or solvate or stereoisomer thereof;
wherein:
D is a drug moiety;
T is a targeting moiety which is an antibody that specifically binds to a folate receptor alpha (FRA) (e.g., a human FRA);

$R^1$ is hydrogen, unsubstituted or substituted $C_{1-3}$ alkyl, or unsubstituted or substituted heterocyclyl;
$L^1$ is a bond, a second self-immolative linker, or a cyclization self-elimination linker;
$L^2$ is a bond or a second self-immolative linker;
  wherein if $L^1$ is a second self-immolative linker or a cyclization self-elimination linker, then $L^2$ is a bond;
  wherein if $L^2$ is a second self-immolative linker, then $L^1$ is a bond;
$L^3$ is a peptide linker;
$L^4$ is a bond or a spacer; and
A is an acyl unit;
comprising reacting the antibody with Compound Z:

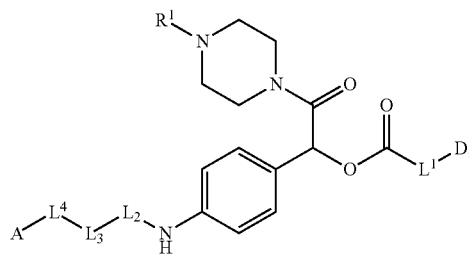

(Compound Z)

or a salt or solvate or stereoisomer thereof.

Provided herein is a process for making a compound of formula (IIa):

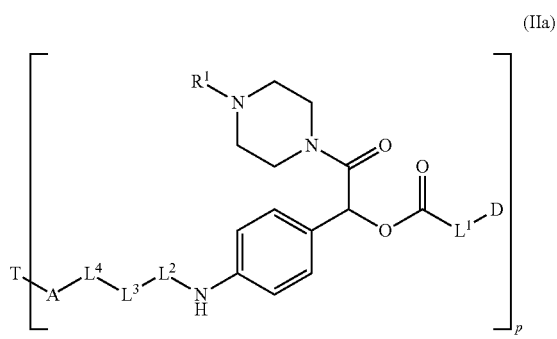

(IIa)

or a salt or solvate or stereoisomer thereof;
wherein:
p is 1 to 20;
D is a drug moiety;
T is a targeting moiety which is an antibody that specifically binds to a folate receptor alpha (FRA) (e.g., a human FRA);
$R^1$ is hydrogen, unsubstituted or substituted $C_{1-3}$ alkyl, or unsubstituted or substituted heterocyclyl;
$L^1$ is a bond, a second self-immolative linker, or a cyclization self-elimination linker;
$L^2$ is a bond or a second self-immolative linker;
  wherein if $L^1$ is a second self-immolative linker or a cyclization self-elimination linker, then $L^2$ is a bond;
  wherein if $L^2$ is a second self-immolative linker, then $L^1$ is a bond;
$L^3$ is a peptide linker;
$L^4$ is a bond or a spacer; and
A is an acyl unit;
comprising reacting the antibody with Compound Z:

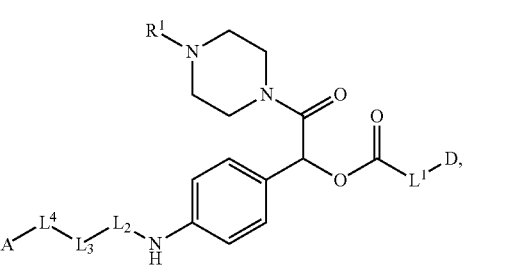

(Compound Z)

or a salt or solvate or stereoisomer thereof.

In certain embodiments of the methods and processes herein, the antibody comprises one or more sulfhydryl groups. In certain embodiments, one or more amino acid residues of a heavy chain of the anti-folate receptor alpha (FRA) antibody are replaced with one or more cysteine residues. In certain embodiments, one or more amino acid residues in the heavy chain constant region (e.g., CH1, CH2, or CH3) are replaced with one or more cysteine residues. In certain embodiments, the antibody comprises a heavy chain constant region (e.g., a heavy chain constant region of a human IgG), wherein one or more amino acid residues selected from positions 155, 157, 165, 169, 197, 199, and 442 in the heavy chain constant region are replaced with one or more cysteine residues, wherein the numbering is according to the EU index of Kabat. In certain embodiments, the antibody comprises a heavy chain constant region of human IgG1, human IgG2, human IgG3, human IgG4 or human IgG4p, wherein one or more amino acid residues selected from positions 155, 157, 165, 169, 197, 199, and 442 in the heavy chain constant region are replaced with one or more cysteine residues, wherein the numbering is according to the EU index of Kabat. In certain embodiments, the antibody comprises a heavy chain constant region comprising the amino acid sequence of SEQ ID NO:32 and SEQ ID NO:33, wherein one or more amino acid residues selected from positions 155, 157, 165, 169, 197, 199, and 442 in the heavy chain constant region are replaced with one or more cysteine residues, wherein the numbering is according to the EU index of Kabat.

In certain embodiments of the methods and processes described herein, one or more amino acid residues of a light chain of the antibody are replaced with one or more cysteine residues. In certain embodiments, one or more amino acid residues in the light chain constant region of the antibody are replaced with one or more cysteine residues. In certain embodiments, the antibody comprises a light constant region (such as a human kappa light chain constant region), wherein one or more amino acid residues selected from positions 201 and 206 in the light chain constant region are replaced with one or more cysteine residues, wherein the numbering is according to the EU index of Kabat. In certain embodiments, the antibody comprises a light chain constant region of human IgG1, human IgG2, human IgG3, human IgG4 or human IgG4p, wherein one or more amino acid residues selected from positions 201 and 206 in the light chain constant region are replaced with one or more cysteine residues, wherein the numbering is according to the EU index of Kabat. In certain embodiments, the antibody comprises a light chain constant region comprising the amino acid sequence of SEQ ID NO:34, wherein one or more amino acid residues selected from positions 201 and 206 in the light chain constant region are replaced with one or more cysteine residues, wherein the numbering is according to the EU index of Kabat.

In certain embodiments of the methods or processes herein, D is linked to T by way of (or via) the added cysteine residue. In some embodiments, D is linked to T via the thiol group of the added cysteine residue connected through the linker moiety (-A-L$^4$-L$^3$-L$^2$-X-L$^1$-).

In certain embodiments of the methods or processes herein, the anti-folate receptor alpha (FRA) antibody is a humanized antibody, a chimeric antibody or a human antibody. In certain embodiments, the anti-folate receptor alpha (FRA) antibody comprises a heavy chain variable region and a light chain variable region, wherein:

(1) the heavy chain variable region comprises the three heavy chain HVRs (e.g., SEQ ID NOs: 14, 15, and 16) of antibody hLK26 and/or the light chain variable region comprises the three light chain HVRs (e.g., SEQ ID NOs: 17, 18, and 19) of antibody hLK26;

(2) the heavy chain variable region comprises the three heavy chain HVRs (e.g., SEQ ID NOs: 20, 21, and 22) of antibody 26B3 and/or the light chain variable region comprises the three light chain HVRs (e.g., SEQ ID NOs: 23, 24 and 25) of antibody 26B3; or (3) the heavy chain variable region comprises the three heavy chain HVRs (e.g., SEQ ID NOs: 26, 27, and 28) of antibody hMov19 and/or the light chain variable region comprises the three light chain HVRs (e.g., SEQ ID NOs: 29, 30, and 31) of antibody hMov19.

In certain embodiments of the methods or processes herein, the anti-folate receptor alpha (FRA) antibody is a humanized antibody, a chimeric antibody or a human antibody. In certain embodiments, the anti-folate receptor alpha (FRA) antibody comprises a heavy chain variable region and a light chain variable region, wherein:

(1) the heavy chain variable region comprises the three heavy chain HVRs (e.g., SEQ ID NOs: 14, 15, and 16) of the amino acid sequence of SEQ ID NO:8 and/or the light chain variable region comprises the three light chain HVRs (e.g., SEQ ID NOs: 17, 18, and 19) of the amino acid sequence of SEQ ID NO:9;

(2) the heavy chain variable region comprises the three heavy chain HVRs (e.g., SEQ ID NOs: 20, 21, and 22) of the amino acid sequence of SEQ ID NO:10 and/or the light chain variable region comprises the three light chain HVRs (e.g., SEQ ID NOs: 23, 24 and 25) of the amino acid sequence of SEQ ID NO:11; or (3) the heavy chain variable region comprises the three heavy chain HVRs (e.g., SEQ ID NOs: 26, 27, and 28) of the amino acid sequence of SEQ ID NO:12 and/or the light chain variable region comprises the three light chain HVRs (e.g., SEQ ID NOs: 29, 30, and 31) of the amino acid sequence of SEQ ID NO:13.

In certain embodiments of the methods and processes herein, the anti-folate receptor alpha (FRA) antibody comprises a heavy chain variable region and a light chain variable region, wherein:

(1) the heavy chain variable region comprises the amino acid sequence of SEQ ID NO:8 and/or the light chain variable region comprising the amino acid sequence of SEQ ID NO:9;

(2) the heavy chain variable region comprises the amino acid sequence of SEQ ID NO:10 and/or the light chain variable region comprising the amino acid sequence of SEQ ID NO:11; or (3) the heavy chain variable region comprises the amino acid sequence of SEQ ID NO:12 and/or the light chain variable region comprising the amino acid sequence of SEQ ID NO:13.

In certain embodiments, the anti-folate receptor alpha (FRA) antibody comprises a heavy chain and a light chain, wherein (1) the heavy chain comprises the amino acid sequence of SEQ ID NO: 1 and/or the light chain comprises the amino acid sequence of SEQ ID NO: 3;

(2) the heavy chain comprises the amino acid sequence of SEQ ID NO: 2 and/or the light chain comprises the amino acid sequence of SEQ ID NO: 3;

(3) the heavy chain comprises a variable region comprising the amino acid sequence of SEQ ID NO: 10 and a constant region comprising the amino acid sequence of SEQ ID NO: 32 or 33 and/or the light chain comprises a variable region comprising the amino acid sequence of SEQ ID NO: 11 and a constant region comprising the amino acid sequence of SEQ ID NO: 34; or (4) the heavy chain comprises the amino acid sequence of SEQ ID NO: 6 and/or the light chain comprises the amino acid sequence of SEQ ID NO: 7.

In certain embodiments of the methods and processes herein, the antibody comprises a heavy chain constant region comprising the amino acid sequence of SEQ ID NO:32 or SEQ ID NO:33 and a human kappa light chain constant region comprising the amino acid sequence of SEQ ID NO:34, wherein one or more amino acid residues selected from T155, S157, S165, T169, T197, T199, and S442 in the heavy chain constant region, and/or one or more amino acid residues selected from L201 and T206 in the kappa light chain constant region are replaced with a cysteine residue, and wherein the numbering is according to the EU index of Kabat. In some of these embodiments, at least one (e.g., one) amino acid residue selected from T155, S157, S165, T169, T197, T199, and S442 in the heavy chain constant region, and/or at least one (e.g., one) amino acid residue selected from L201 and T206 in the light chain constant region is replaced with a cysteine residue.

The present disclosure provides a compound, or a salt or solvate or stereoisomer thereof, wherein the compound is prepared by a method or process described herein, wherein the antibody comprises one or more sulfhydryl groups.

The present disclosure provides a pharmaceutical composition comprising a compound, or a salt or solvate or stereoisomer thereof, wherein the compound is prepared by a process described herein, wherein the antibody comprises one or more sulfhydryl groups, and a pharmaceutically acceptable carrier.

It is to be understood that one, some, or all of the properties of the various embodiments described herein may be combined to form other embodiments of the present invention. These and other aspects of the invention will become apparent to one of skill in the art.

DEFINITIONS

Figure 1:
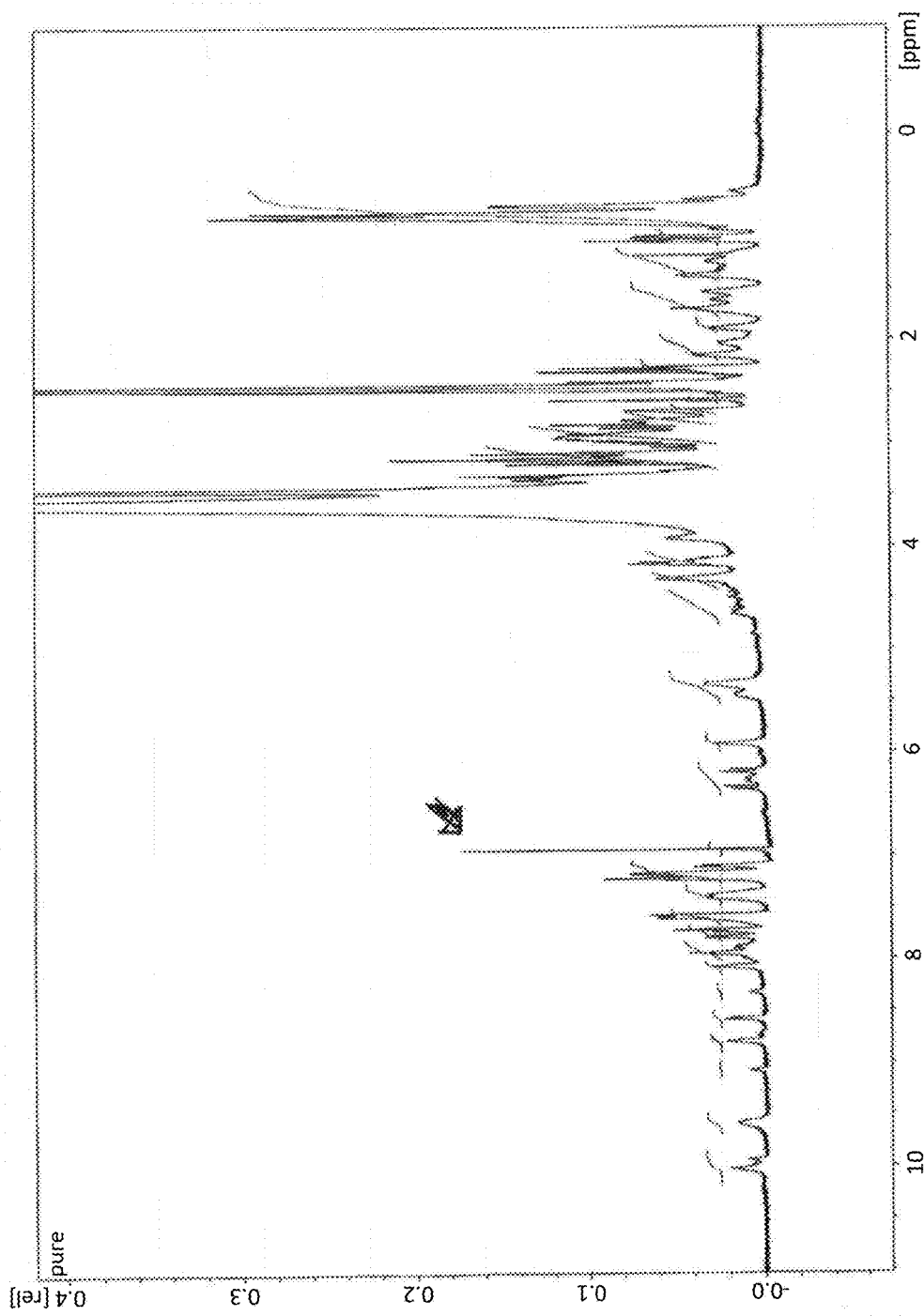
FIG. 1 shows an NMR spectrum of Tap-18H.

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl (CH$_3$—), ethyl (CH$_3$CH$_2$—), n-propyl (CH$_3$CH$_2$CH$_2$—), isopropyl ((CH$_3$)$_2$CH—), n-butyl (CH$_3$CH$_2$CH$_2$CH$_2$—), isobutyl ((CH$_3$)$_2$CHCH$_2$—), sec-butyl ((CH$_3$)(CH$_3$CH$_2$)CH—), t-butyl ((CH$_3$)$_3$C—), n-pentyl (CH$_3$CH$_2$CH$_2$CH$_2$CH$_2$—), neopentyl ((CH$_3$)$_3$CCH$_2$—), and n-hexyl (CH$_3$(CH$_2$)$_5$—).

"Alkylene" refers to divalent aliphatic hydrocarbylene groups preferably having from 1 to 10 and more preferably 1 to 3 carbon atoms that are either straight-chained or branched. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Alkenyl" refers to straight chain or branched hydrocarbyl groups having from 2 to 10 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

"Alkenylene" refers to straight chain or branched hydrocarbylene groups having from 2 to 10 carbon atoms and preferably 2 to 4 carbon atoms and having at least 1 and preferably from 1 to 2 sites of double bond unsaturation. Examples of alkenylene include, but is not limited to, vinylene (—CH=CH—), allylene (—CH$_2$C=C—), and but-3-en-1-ylene (—CH$_2$CH$_2$C=CH—). Included within this term are the cis and trans isomers or mixtures of these isomers.

"Alkynyl" refers to straight or branched hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

"Alkynylene" refers to straight or branched hydrocarbylene groups having from 2 to 6 carbon atoms and preferably 2 to 3 carbon atoms and having at least 1 and preferably from 1 to 2 sites of triple bond unsaturation. Examples of alkynylene include, but are not limited to, acetylenylene (—C≡C—), and propargylene (—CH$_2$C≡C—).

"Amino" refers to the group —NH$_2$.

"Substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

"Aryl" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxyl ester, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, sulfonylamino, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantyl, and the like.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuranyl, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxyl ester, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, sulfonylamino, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl, and trihalomethyl.

Examples of heteroaryls include, but are not limited to, pyrrole, imidazole, pyrazole, pyridine, pyrazine, pyrimidine, pyridazine, indolizine, isoindole, indole, purine, isoquinoline, quinoline, phthalazine, naphthyridine, quinoxaline, quinazoline, cinnoline, pteridine, carbazole, carboline, phenanthridine, acridine, phenanthroline, isothiazole, phenazine, isoxazole, phenoxazine, phenothiazine, piperidine, piperazine, phthalimide, 4,5,6,7-tetrahydrobenzo[b]thiophene, thiazole, thiophene, benzo[b]thiophene, and the like.

"Heterocycle," "heterocyclic," "heterocycloalkyl" or "heterocyclyl" refers to a saturated or partially unsaturated group having a single ring or multiple condensed rings, including fused, bridged, or spiro ring systems, and having from 3 to 20 ring atoms, including 1 to 10 hetero atoms. These ring atoms are selected from the group consisting of carbon, nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for N-oxide, —S(O)—, or —SO$_2$— moieties.

Examples of heterocycles include, but are not limited to, azetidine, dihydroindole, indazole, quinolizine, imidazolidine, imidazoline, piperidine, piperazine, indoline, 1,2,3,4-tetrahydroisoquinoline, thiazolidine, morpholinyl, thiomorpholinyl (also referred to as thiamorpholinyl), 1,1-dioxothiomorpholinyl, piperidinyl, pyrrolidine, tetrahydrofuranyl, and the like.

Where a heteroaryl or heterocyclyl group is "substituted," unless otherwise constrained by the definition for the heteroaryl or heterocyclic substituent, such heteroaryl or heterocyclic groups can be substituted with 1 to 5, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, azido, cyano, halogen, hydroxyl, oxo, thioketo, carboxyl, carboxyl ester, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, sulfonylamino, —SO-alkyl, —SO-substituted alkyl, —SO-aryl, —SO-heteroaryl, —SO-heterocyclyl, —SO$_2$-alkyl, —SO$_2$-substituted alkyl, —SO$_2$-aryl, —SO$_2$-heteroaryl, and —SO$_2$-heterocyclyl.

"Polyalkylene glycol" refers to straight or branched polyalkylene glycol polymers such as polyethylene glycol, polypropylene glycol, and polybutylene glycol. A polyalkylene glycol subunit is a single polyalkylene glycol unit. For example, an example of a polyethylene glycol subunit would be an ethylene glycol, —O—CH$_2$—CH$_2$—O—, or propylene glycol, —O—CH$_2$—CH$_2$—CH$_2$—O—, capped with a hydrogen at the chain termination point. Other examples of poly(alkylene glycol) include, but are not limited to, PEG, PEG derivatives such as methoxypoly(ethylene glycol) (mPEG), poly(ethylene oxide), PPG, poly(tetramethylene glycol), poly(ethylene oxide-co-propylene oxide), or copolymers and combinations thereof.

"Polyamine" refers to polymers having an amine functionality in the monomer unit, either incorporated into the backbone, as in polyalkyleneimines, or in a pendant group as in polyvinyl amines.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR$^{70}$, =N—OR$^{70}$, =N$_2$ or =S) on saturated carbon atoms in the specified group or radical are, unless otherwise specified, —R$^{60}$, halo, =O, —OR$^{70}$, —SR$^{70}$, —NR$^{80}$R$^{80}$, trihalomethyl, —CN, —OCN, —SCN, —NO, —NO$_2$, =N$_2$, —N$_3$, —S(O)R$^{70}$, —S(O)$_2$R$^{70}$, —SO$_3^-$M$^+$, —S(O)$_2$OR$^{70}$, —OS(O)$_2$R$^{70}$, —OSO$_3^-$M$^+$, —OS(O)$_2$OR$^{70}$, —PO$_3^{2-}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —C(O)O$^-$M$^+$, —C(O)OR$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —OC(O)O$^-$M$^+$, —OC(O)OR$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$ is selected from the group consisting of optionally substituted alkyl, cycloalkyl, heterocycloalkyl, heterocycloalkylalkyl, cycloalkylalkyl, aryl, arylalkyl, heteroaryl and heteroarylalkyl, each R$^{70}$ is independently hydrogen or R$^{60}$; each R$^{80}$ is independently R$^{70}$ or alternatively, two R$^{80}$'s, taken together with the nitrogen atom to which they are bonded, form a 3-, 4-, 5-, 6-, or 7-membered heterocycloalkyl which may optionally include from 1 to 4 of the same or different additional heteroatoms selected from the group consisting of O, N and S, of which N may have —H, C$_1$-C$_4$ alkyl, —C(O)C$_{1-4}$alkyl, —CO$_2$C$_{1-4}$alkyl, or —S(O)$_2$C$_{1-4}$alkyl substitution; and each M$^+$ is a counter ion with a net single positive charge. Each M$^+$ may independently be, for example, an alkali ion, such as K$^+$, Na$^+$, Li$^+$; an ammonium ion, such as $^+$N(R$^{60}$)$_4$; or an alkaline earth ion, such as [Ca$^{2+}$]$_{0.5}$, [Mg$^{2+}$]$_{0.5}$, or [Ba$^{2+}$]$_{0.5}$ ("subscript 0.5 means that one of the counter ions for such divalent alkali earth ions can be an ionized form of a compound of the embodiments and the other a typical counter ion such as chloride, or two ionized compounds disclosed herein can serve as counter ions for such divalent alkali earth ions, or a doubly ionized compound of the embodiments can serve as the counter ion for such divalent alkali earth ions).

In addition to the disclosure herein, substituent groups for hydrogens on unsaturated carbon atoms in "substituted" alkene, alkyne, aryl and heteroaryl groups are, unless otherwise specified, —R$^{60}$, halo, —O$^-$M$^+$, —OR$^{70}$, —SR$^{70}$, —NR$^{80}$R$^{80}$, trihalomethyl, —CF$_3$, —CN, —OCN, —SCN, —NO, —NO$_2$, —N$_3$, —S(O)R$^{70}$, —S(O)$_2$R$^{70}$, —SO$_3$R$^{70}$, —OS(O)$_2$R$^{70}$, —OSO$_3^-$M$^+$, —OSO$_3$R$^{70}$, —PO$_3^{2-}$(M$^+$)$_2$, —P(O)(OR$^{70}$)O$^-$M$^+$, —P(O)(OR$^{70}$)$_2$, —C(O)R$^{70}$, —C(S)R$^{70}$, —C(NR$^{70}$)R$^{70}$, —CO$_2^-$M$^+$, —CO$_2$R$^{70}$, —C(S)OR$^{70}$, —C(O)NR$^{80}$R$^{80}$, —C(NR$^{70}$)NR$^{80}$R$^{80}$, —OC(O)R$^{70}$, —OC(S)R$^{70}$, —CO$_2^-$M$^+$, —CO$_2$R$^{70}$, —OC(S)OR$^{70}$, —NR$^{70}$C(O)R$^{70}$, —NR$^{70}$C(S)R$^{70}$, —NR$^{70}$CO$_2^-$M$^+$, —NR$^{70}$CO$_2$R$^{70}$, —NR$^{70}$C(S)OR$^{70}$, —NR$^{70}$C(O)NR$^{80}$R$^{80}$, —NR$^{70}$C(NR$^{70}$)R$^{70}$ and —NR$^{70}$C(NR$^{70}$)NR$^{80}$R$^{80}$, where R$^{60}$, R$^{70}$, R$^{80}$ and M$^+$ are as previously defined, provided that in case of substituted alkene or alkyne, the substituents are not —O$^-$M$^+$, —OR$^{70}$, —SR$^{70}$, or —S$^-$M$^+$.

In addition to the substituent groups disclosed with respect to the individual terms herein, substituent groups for hydrogens on nitrogen atoms in "substituted" heterocycloalkyl and cycloalkyl groups are, unless otherwise specified, —$R^{60}$, —$O^-M^+$, —$OR^{70}$, —$SR^{70}$, —$S^-M^+$, —$NR^{80}R^{80}$, trihalomethyl, —$CF_3$, —CN, —NO, —$NO_2$, —S(O)$R^{70}$, —S(O)$_2R^{70}$, —S(O)$_2O^-M^+$, —S(O)$_2OR^{70}$, —OS(O)$_2R^{70}$, —OS(O)$_2O^-M^+$, —OS(O)$_2OR^{70}$, —$PO_3^{2-}$($M^+$)$_2$, —P(O)(O$R^{70}$)$O^-M^+$, —P(O)(O$R^{70}$)(O$R^{70}$), —C(O)$R^{70}$, —C(S)$R^{70}$, —C(N$R^{70}$)$R^{70}$, —C(O)O$R^{70}$, —C(S)O$R^{70}$, —C(O)N$R^{80}R^{80}$, —C(N$R^{70}$)N$R^{80}R^{80}$, —OC(O)$R^{70}$, —OC(S)$R^{70}$, —OC(O)O$R^{70}$, —OC(S)O$R^{70}$, —N$R^{70}$C(O)$R^{70}$, —N$R^{70}$C(S)$R^{70}$, —N$R^{70}$C(O)O$R^{70}$, —N$R^{70}$C(S)O$R^{70}$, —N$R^{70}$C(O)N$R^{80}R^{80}$, —N$R^{70}$C(N$R^{70}$)$R^{70}$ and —N$R^{70}$C(N$R^{70}$)N$R^{80}R^{80}$, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

A wavy line in the structure drawing of a group represents an attachment point of the group to the parent structure.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

As used herein, an "effective dosage" or "effective amount" of drug, compound, conjugate, drug conjugate, antibody drug conjugate, or pharmaceutical composition is an amount sufficient to effect beneficial or desired results. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent and preferably stop) cancer cell infiltration into peripheral organs; inhibit (i.e., slow to some extent and preferably stop) tumor metastasis; inhibiting, to some extent, tumor growth; and/or relieving to some extent one or more of the symptoms associated with the disorder. An effective dosage can be administered in one or more administrations. For purposes of the present disclosure, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during or after administration of the other treatment modality to the individual.

As used herein, "treatment" or "treating" is an approach for obtaining beneficial or desired results including and preferably clinical results. For purposes of the present disclosure, beneficial or desired clinical results include, but are not limited to, one or more of the following: reducing the proliferation of (or destroying) cancerous cells, decreasing symptoms resulting from the disease, increasing the quality of life of those suffering from the disease, decreasing the dose of other medications required to treat the disease, delaying the progression of the disease, and/or prolonging survival of individuals.

As used herein, "delaying development of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "individual" or a "subject" is a mammal, more preferably a human. Mammals also include, but are not limited to, farm animals, sport animals, pets (such as cats, dogs, horses), primates, mice and rats.

As used herein, the term "specifically recognizes" or "specifically binds" refers to measurable and reproducible interactions such as attraction or binding between a target and an antibody (or a molecule or a moiety), that is determinative of the presence of the target in the presence of a heterogeneous population of molecules including biological molecules. For example, an antibody that specifically or preferentially binds to an epitope is an antibody that binds this epitope with greater affinity, avidity, more readily, and/or with greater duration than it binds to other epitopes of the target or non-target epitopes. It is also understood that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ $M^{-1}$ or $10^4$ $M^{-1}$, sometimes about $10^5$ $M^{-1}$ or $10^6$ $M^{-1}$, in other instances about $10^6$ $M^{-1}$ or $10^7$ $M^{-1}$, about $10^8$ $M^{-1}$ to $10^9$ $M^{-1}$, or about $10^{10}$ $M^{-1}$ to $10^{11}$ $M^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, the terms "cancer," "tumor," "cancerous," and "malignant" refer to or describe the physiological condition in mammals that is typically characterized by unregulated cell growth. Examples of cancer include but are not limited to, carcinoma, including adenocarcinoma, lymphoma, blastoma, melanoma, and sarcoma. More particular examples of such cancers include squamous cell cancer, small-cell lung cancer, non-small cell lung cancer, lung adenocarcinoma, lung squamous cell carcinoma, gastrointestinal cancer, Hodgkin's and non-Hodgkin's lymphoma, pancreatic cancer, glioblastoma, cervical cancer, glioma, ovarian cancer, liver cancer such as hepatic carcinoma and hepatoma, bladder cancer, breast cancer, colon cancer, colorectal cancer, endometrial or uterine carcinoma, salivary gland carcinoma, kidney cancer such as renal cell carcinoma and Wilms' tumors, basal cell carcinoma, melanoma, mesothelioma, prostate cancer, thyroid cancer, testicular cancer, esophageal cancer, gallbladder cancer, and various types of head and neck cancer.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

Reference to "about" a value or parameter herein includes (and describes) embodiments that are directed to that value or parameter per se. For example, description referring to "about X" includes description of "X."

It is understood that aspect and variations of the invention described herein include "consisting" and/or "consisting essentially of" aspects and variations.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, $4^{th}$ edition, New York: Oxford University Press, 2002, pp. 360-361, 1084-1085; Smith and March, March's Advanced Organic Chemistry: Reactions, Mechanisms, and Structure, $5^{th}$ edition, Wiley-Interscience, 2001.

The nomenclature used herein to name the subject compounds is illustrated in the Examples herein. This nomenclature has generally been derived using the commercially-available AutoNom software (MDL, San Leandro, Calif.).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. All combinations of the embodiments pertaining to the chemical groups represented by the variables are specifically embraced by the present invention and are disclosed herein just as if each and every combination was individually and explicitly disclosed, to the extent that such combinations embrace compounds that are stable compounds (i.e., compounds that can be isolated, characterized, and tested for biological activity). In addition, all subcombinations of the chemical groups listed in the embodiments describing such variables are also specifically embraced by the present invention and are disclosed herein just as if each and every such sub-combination of chemical groups was individually and explicitly disclosed herein.

DETAILED DESCRIPTION

The present disclosure provides compounds (anti-FRA antibody-drug conjugates) with a hydrophilic self-immolative linker, which may be cleavable under appropriate conditions and incorporates a hydrophilic group to provide better solubility of the conjugate. The hydrophilic self immolative linker may provide increased solubility of drug conjugates for cytotoxic drugs which are often hydrophobic. Other advantages of using a hydrophilic self-immolative linker in a drug conjugate include increased stability of the drug conjugate and decreased aggregation of the drug conjugate.

The present disclosure provides antibody-drug conjugates that may have superior serum stability. For example, in contrast to antibody-drug conjugates wherein a hydroxyl group of a drug is linked to a spacer via a labile carbonate linkage that is susceptible to rapid hydrolysis in aqueous buffer or human serum, the antibody-drug conjugates of the present embodiments utilizing a benzyloxycarbonyl linkage may be relatively more stable under the same conditions, and may selectively undergo fragmentation to release the drug upon treatment with protease, e.g., cathepsin B. Serum stability is a desirable property for antibody-drug conjugates where it is desired to administer inactive drug to the patient's serum, have that inactive drug concentrate at a target by way of the ligand, and then have that antibody-drug conjugate converted to an active form only in the vicinity of the target.

The present disclosure provides antibody-drug conjugates which may have decreased aggregation. Increased associated hydrophobicity of some enzyme-labile linkers may lead to aggregation of antibody-drug conjugates, particularly with strongly hydrophobic drugs. With incorporation of a hydrophilic group into the linker, there may be decreased aggregation of the antibody-drug conjugate.

The compounds (antibody-drug conjugates) of the present disclosure comprise a drug moiety, a targeting moiety capable of targeting a selected cell population (e.g., FRA expressing cells), and a linker which contains an acyl unit, an optional spacer unit for providing distance between the drug moiety and the targeting moiety, a peptide linker which can be cleavable under appropriate conditions, a hydrophilic self-immolative linker, and an optional second self-immolative spacer or cyclization self-elimination linker. Each of the features is discussed below.

The present disclosure provides a compound of Formula (I):

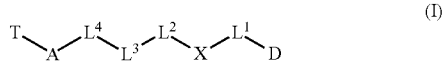

or a salt or solvate or stereoisomer thereof;
wherein:
D is a drug moiety;
T is a targeting moiety;
X is a hydrophilic self-immolative linker;
$L^1$ is a bond, a second self-immolative linker, or a cyclization self-elimination linker;
$L^2$ is a bond or a second self-immolative linker;
    wherein if $L^1$ is a second self-immolative linker or a cyclization self-elimination linker, then $L^2$ is a bond;
    wherein if $L^2$ is a second self-immolative linker, then $L^1$ is a bond;
$L^3$ is a peptide linker;
$L^4$ is a bond or a spacer; and
A is an acyl unit.

In some embodiments, the targeting moiety is an antibody that specifically binds to a FRA (e.g., a human FRA). In some embodiments, the targeting moiety is an anti-FRA antibody which has one or more attachment sites for linking to the drug moiety. For example, a targeting moiety T can have multiple sites for linking to a linker-drug moiety (e.g., $A-L^4-L^3-L^2-X-L^1-D$). Thus, also provided is a compound of Formula (Ia):

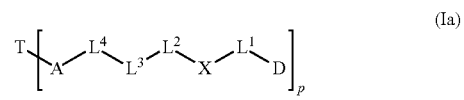

or a salt or solvate or stereoisomer thereof; wherein D, T, X, $L^1$, $L^2$, $L^3$, $L^4$ and A are as defined for Formula (I), and p is 1 to 20. In some embodiments, p is 1 to 8. In some embodiments, p is 1 to 6. In some embodiments, p is 1 to 4. In some embodiments, p is 2 to 4. In some embodiments, p is 1, 2, 3 or 4. In some embodiments, p is 2. In some embodiments, p is 3. In some embodiments, p is 4.

Peptide Linker

In Formula (I), $L^3$ is a peptide linker. In certain embodiments, $L^3$ is a peptide linker of 1 to 10 amino acid residues. In certain embodiments, $L^3$ is a peptide linker of 2 to 4 amino acid residues. In certain instances, $L^3$ is a dipeptide linker.

An amino acid residue can be a naturally-occurring or non-natural amino acid residue. The terms "natural amino acid" and "naturally-occurring amino acid" refer to Ala, Asp, Cys, Glu, Phe, Gly, His, Ile, Lys, Leu, Met, Asn, Pro, Gln, Arg, Ser, Thr, Val, Trp, and Tyr. "Non-natural amino acids" (i.e., amino acids do not occur naturally) include, by way of non-limiting example, homoserine, homoarginine, citrulline, phenylglycine, taurine, iodotyrosine, seleno-cysteine, norleucine ("Nle"), norvaline ("Nva"), beta-alanine, L- or D-naphthalanine, ornithine ("Orn"), and the like.

Amino acids also include the D-forms of natural and non-natural amino acids. "D-" designates an amino acid having the "D" (dextrorotary) configuration, as opposed to the configuration in the naturally occurring ("L-") amino acids. Where no specific configuration is indicated, one skilled in the art would understand the amino acid to be an L-amino acid. The amino acids can, however, also be in racemic mixtures of the D- and L-configuration. Natural and non-natural amino acids can be purchased commercially (Sigma Chemical Co.; Advanced Chemtech) or synthesized using methods known in the art Amino acid substitutions may be made on the basis of similarity in polarity, charge, solubility, hydrophobicity, hydrophilicity, and/or the amphipathic nature of the residues as long as their biological activity is retained.

The amino acid residue sequence can be specifically tailored so that it will be selectively enzymatically cleaved from the resulting peptidyl derivative drug-conjugate by one or more of the tumor-associated proteases.

In certain embodiments, $L^3$ is a peptide linker comprising at least one lysine or arginine residue.

In certain embodiments, $L^3$ is a peptide linker comprising an amino acid residue selected from lysine, D-lysine, citrulline, arginine, proline, histidine, ornithine and glutamine.

In certain embodiments, $L^3$ is a peptide linker comprising an amino acid residue selected from valine, isoleucine, phenylalanine, methionine, asparagine, proline, alanine, leucine, tryptophan, and tyrosine.

In certain embodiments, $L^3$ is a dipeptide linker selected from valine-citrulline, proline-lysine, methionine-D-lysine, asparagine-D-lysine, isoleucine-proline, phenylalanine-lysine, and valine-lysine. In certain embodiments, $L^3$ is valine-citrulline.

Numerous specific peptide linker molecules suitable for use in the present disclosure can be designed and optimized in their selectivity for enzymatic cleavage by a particular tumor-associated protease. Certain peptide linkers for use in the present disclosure are those which are optimized toward the proteases, cathepsin B and D.

Hydrophilic Self-Immolative Linker

In Formula (I), X is a hydrophilic self-immolative linker.

The compound of the present disclosure employs a hydrophilic self-immolative spacer moiety which spaces and covalently links together the drug moiety and the targeting moiety and incorporates a hydrophilic group, which provides better solubility of the compound. Increased associated hydrophobicity of some enzyme-labile linkers can lead to aggregation of drug conjugates, particularly with strongly hydrophobic drugs. With incorporation of a hydrophilic group into the linker, there may be a decreased aggregation of the drug conjugate.

A self-immolative spacer may be defined as a bifunctional chemical moiety which is capable of covalently linking together two spaced chemical moieties into a normally stable tripartite molecule, can release one of the spaced chemical moieties from the tripartite molecule by means of enzymatic cleavage; and following enzymatic cleavage, can spontaneously cleave from the remainder of the molecule to release the other of the spaced chemical moieties.

In certain embodiments, X is a benzyloxycarbonyl group. In certain embodiments, X is

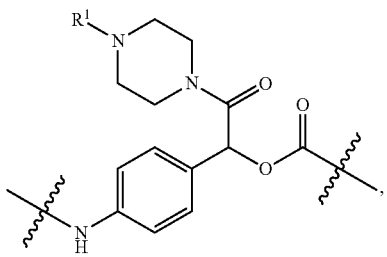

wherein $R^1$ is hydrogen, unsubstituted or substituted $C_{1-3}$ alkyl, or unsubstituted or substituted heterocyclyl.

In such instance, the present disclosure provides a compound of Formula (II):

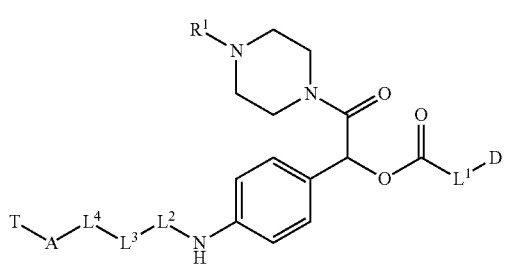

(II)

or a salt or solvate or stereoisomer thereof;
wherein:
D is a drug moiety;
T is a targeting moiety;
$R^1$ is hydrogen, unsubstituted or substituted $C_{1-3}$ alkyl, or unsubstituted or substituted heterocyclyl;

$L^1$ is a bond, a second self-immolative linker, or a cyclization self-elimination linker;
$L^2$ is a bond, a second self-immolative linker;
  wherein if $L^1$ is a second self-immolative linker or a cyclization self-elimination linker, then $L^2$ is a bond;
  wherein if $L^2$ is a second self-immolative linker, then $L^1$ is a bond;
$L^3$ is a peptide linker;
$L^4$ is a bond or a spacer; and
A is an acyl unit.

In some embodiments, provided is a compound of Formula (IIa):

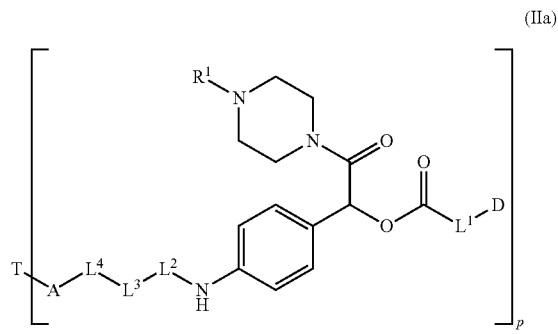

(IIa)

or a salt or solvate or stereoisomer thereof; wherein D, T, $L^1$, $L^2$, $L^3$, $L^4$ and A are as defined for Formula (II), and p is 1 to 20. In some embodiments, p is 1 to 8. In some embodiments, p is 1 to 6. In some embodiments, p is 1 to 4. In some embodiments, p is 2 to 4. In some embodiments, p is 1, 2, 3 or 4. In some embodiments, p is 2. In some embodiments, p is 3. In some embodiments, p is 4.

In certain embodiments of Formula (II) or (IIa), $R^1$ is hydrogen. In certain instances, $R^1$ is methyl.

It is intended and understood that each and every variation of D, T, $L^1$, $L^2$, $L^3$, $L^4$ and A described for formula (I) or (Ia) may be applied to Formula (II) or (IIa) as if each and every variation and combinations thereof is individually described. For example, in some embodiments, the targeting moiety of formula (II) or (IIa) is an antibody that specifically binds to a folate receptor alpha (FRA) (e.g., a human FRA). It is further intended and understood that each and every variation of one of D, T, $L^1$, $L^2$, $L^3$, $L^4$ and A described for formula (I) may be combined with each and every variation of another one of D, T, $L^1$, $L^2$, $L^3$, $L^4$ and A described for formula (I), where applicable, as if each and every combination is individually described.

The release of the drug moiety is based on the self-elimination reaction of aminobenzyloxycarbonyl group. For illustration purposes, a reaction scheme with an aminobenzyloxycarbonyl group with a drug and peptide attached is shown below.

Scheme 1

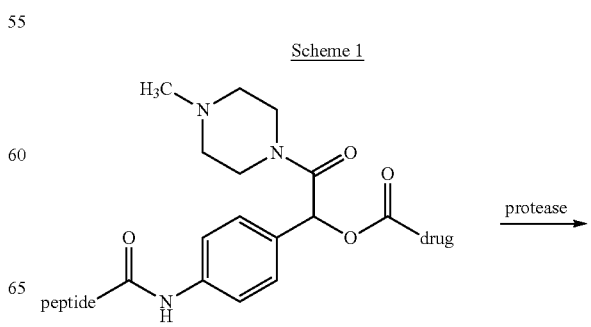

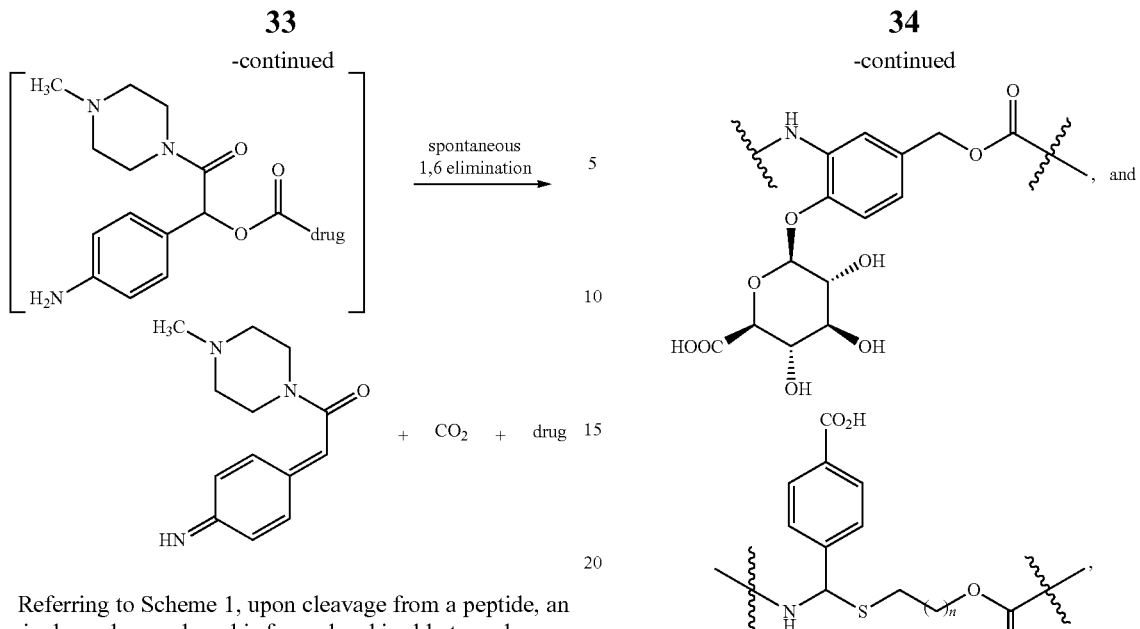

Referring to Scheme 1, upon cleavage from a peptide, an aminobenzyloxycarbonyl is formed and is able to undergo a spontaneous 1,6 elimination to form a cyclohexa-2,5-dien-imine derivative and carbon dioxide and release the drug.

Optional Second Self-Immolative Linker or Cyclization Self-Elimination Linker

A second self-immolative linker or cyclization self-elimination linker provides an additional linker for allowance of fine-tuning the cleavage of the compound to release the drug moiety.

In Formula (I) or (Ia), $L^1$ is a bond, a second self-immolative linker, or a cyclization self-elimination linker; $L^2$ is a bond or a second self-immolative linker; wherein if $L^1$ is a second self-immolative linker or a cyclization self-elimination linker, then $L^2$ is a bond; and wherein if $L^2$ is a second self-immolative linker, then $L^1$ is a bond. Thus, there is an optional second self-immolative linker or a cyclization self-elimination linker adjacent the hydrophilic self-immolative linker.

In certain embodiments, $L^1$ is a bond and $L^2$ is a bond. In certain embodiments, $L^1$ is a second self-immolative linker or a cyclization self-elimination linker and $L^2$ is a bond. In certain embodiments, $L^1$ is a bond and $L^2$ is a second self-immolative linker.

In Formula (I) or (Ia), in certain embodiments, $L^1$ is a bond. In certain embodiments, $L^1$ is a second self-immolative spacer or a cyclization self-elimination linker, which separates the hydrophilic self-immolative linker and the drug moiety. In certain embodiments, $L^1$ is an aminobenzyloxycarbonyl linker.

In certain embodiments, $L^1$ is selected from:

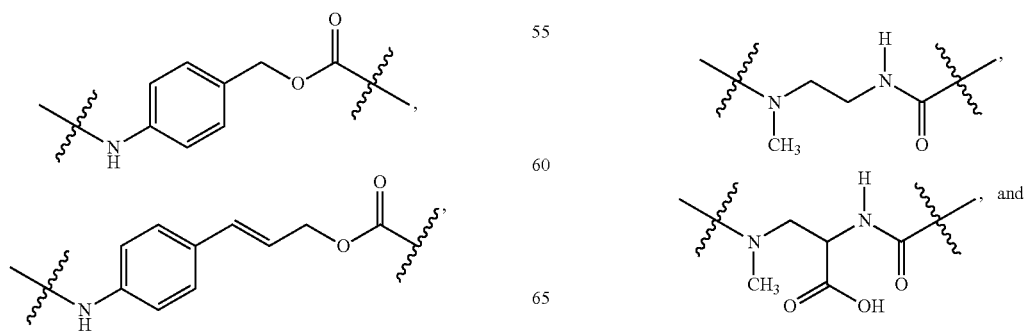

wherein n is 1 or 2.

In certain instances, the second self-immolative linker or cyclization self-elimination linker provides design potential for a wider variety of moieties that can be used. For example, in Formula (II) or (IIa), a carbamate linkage (—O—C(O)—N(H)—) linkage between the hydrophilic self-immolative linker and the drug moiety would provide a stable drug conjugate and would readily cleave to provide a free drug moiety. The hydrophilic self-immolative linker will typically terminate with an oxycarbonyl group (—O—C(O)—). If the drug moiety has an amino-reactive group that may be used to react to form a carbamate group, then the second self-immolative unit or cyclization self-elimination linker is not necessary; although it may still be employed. However, if the drug does not contain an amino group, but instead contains some other reactive functional group, then such drugs may still be incorporated into an aminobenzyloxycarbonyl-containing compound of the present embodiments by including a second, intermediate self-immolative spacer or cyclization self-elimination linker between the drug moiety and the aminobenzyloxycarbonyl group.

The cyclization self-elimination linkers of $L^1$ below provide linkage of hydroxyl-containing or thiol-containing drug moieties to the aminobenzyloxycarbonyl group of the hydrophilic self-immolative linker:

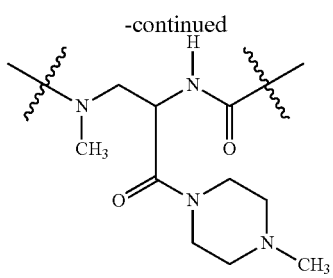

The cyclization self-elimination linkers in the compounds of the embodiments provide for cleavage of the compound to release the drug moiety. The elimination mechanism of the adjacent hydrophilic self-immolative linker would reveal an amino group of $L^1$. The amino group can then react with the carbamate group or thiocarbamate linkage of $L^1$ and the drug moiety in a cyclization reaction to release the hydroxyl-containing or thiol-containing drug moiety.

In Formula (I) or (Ia), in certain embodiments, $L^2$ is a bond. In certain embodiments, $L^2$ is a second self-immolative spacer which separates the hydrophilic self-immolative linker and the peptide linker. In certain embodiments, $L^2$ is an aminobenzyloxycarbonyl linker.

In certain embodiments, $L^2$ is selected from

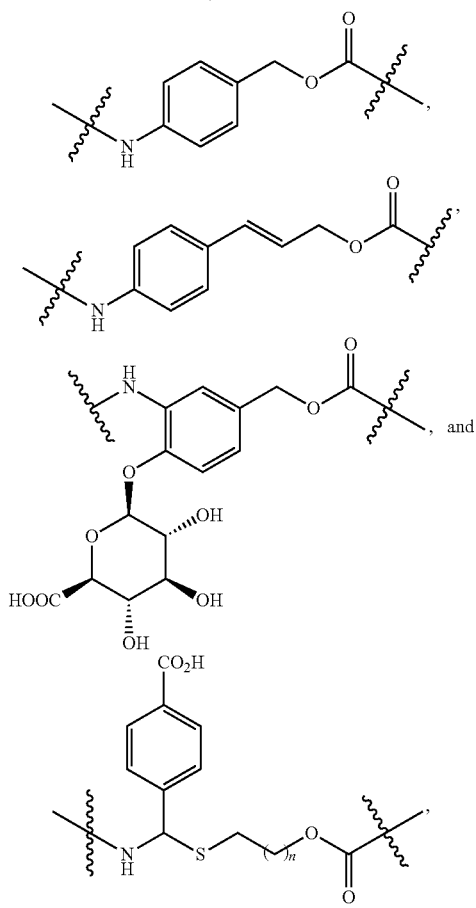

wherein n is 1 or 2.

Optional Spacer

In Formula (I) or (Ia), $L^4$ is a bond or a spacer. In certain embodiments, $L^4$ is a bond. In certain embodiments, $L^4$ is a spacer, which can provide distance between the drug moiety and the targeting moiety.

In certain embodiments, a spacer is selected from alkyl, substituted alkyl, alkenyl, substituted alkenyl, alkynyl, substituted alkynyl, aryl, substituted aryl, cycloalkyl, substituted cycloalkyl, heteroaryl, substituted heteroaryl, heterocyclic, substituted heterocyclic, and heteroatoms, and combinations thereof. The spacer can be homogenous or heterogeneous in its atom content (e.g., spacers containing only carbon atoms or spacers containing carbon atoms as well as one or more heteroatoms present on the spacer. Preferably, the spacer contains 1 to 50 carbon atoms and 0 to 30 heteroatoms selected from oxygen, nitrogen and sulfur. The spacer may also be chiral or achiral, linear, branched or cyclic.

In certain embodiments, L4 is a spacer selected from polyalkylene glycol, alkylene, alkenylene, alkynylene, and polyamine. Examples of alkenylene include, but is not limited to, vinylene (—CH=CH—), allylene (—CH$_2$C=C—), and but-3-en-1-ylene (—CH$_2$CH$_2$C=CH—). Examples of alkynylene include, but are not limited to, acetylenylene (—C≡C—), and propargylene (—CH$_2$C≡C—).

In certain embodiments, $L^4$ is a spacer that comprises a functional group that can provide linkage to the terminal end of the peptide linkage. Functional groups, such as C(O), C(O)—NH, S(O)$_2$, and S(O)$_2$—NH, can provide linkage to the terminal end of the peptide linkage. In certain instances, $L^4$ is $L^{4a}$-C(O), $L^{4a}$-C(O)—NH, $L^{4a}$-S(O)$_2$, $L^{4a}$-S(O)$_2$—$_{NH}$, wherein $L^{4a}$ is selected from polyalkylene glycol, alkylene, alkenylene, alkynylene, and polyamine. In certain instances, $L^4$ is $L^{4a}$-C(O), wherein $L^{4a}$ is selected from polyalkylene glycol, alkylene, alkenylene, alkynylene, and polyamine.

In certain embodiments, $L^4$ is $L^{4a}$-C(O), wherein $L^{4a}$ is a polyalkylene glycol. In certain embodiments, $L^4$ is $L^{4a}$-C(O), wherein $L^{4a}$ is a polyethylene glycol. In certain embodiments, the spacer is of the formula —CH$_2$—(CH$_2$—O—CH$_2$)$_m$—CH$_2$—C(O)—, wherein m is an integer from 0 to 30.

In certain embodiments, $L^4$ is $L^{4a}$-C(O), wherein $L^{4a}$ is alkylene. In certain embodiments, $L^4$ is $L^{4a}$-C(O), wherein $L^{4a}$ is C$_{1-10}$alkylene, C$_{1-8}$alkylene, or C$_{1-6}$alkylene. In certain embodiments, $L^4$ is $L^{4a}$-C(O), wherein $L^{4a}$ is C$_4$alkylene, C$_5$alkylene, or C$_6$alkylene. In certain embodiments, $L^4$ is $L^{4a}$-C(O), wherein $L^{4a}$ is C$_5$alkylene.

Acyl Unit

In Formula (I) or (Ia), A is an acyl unit. In certain embodiments, the acyl unit "A" comprises a sulfur atom and is linked to the targeting moiety via a sulfur atom derived from the targeting moiety. In such instance, a dithio bond is formed between the acyl unit and the targeting moiety.

In certain embodiments, A is selected from

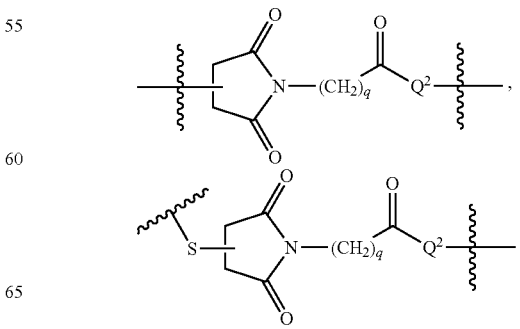

-continued

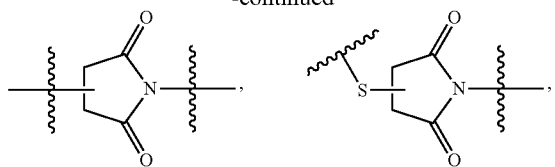

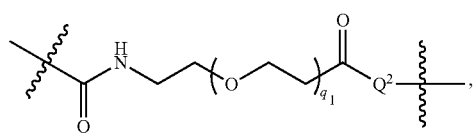

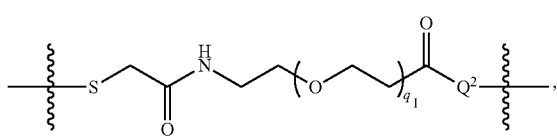

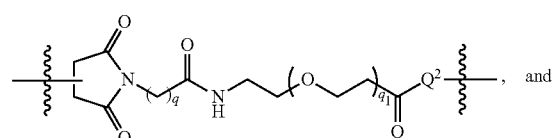

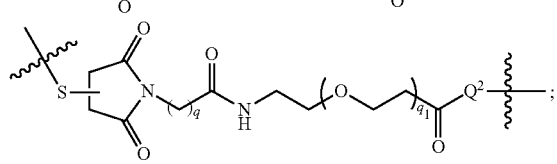

wherein $Q^2$ is NH or O, each q is independently an integer from 1 to 10, and each $q_1$ is independently an integer from 1 to 10. In some embodiments, q is an integer from 2 to 5, such as 2, 3, 4, or 5. In some embodiments, $q_1$ is an integer from 2 to 5, such as 2, 3, 4, or 5.

In certain embodiments, A is

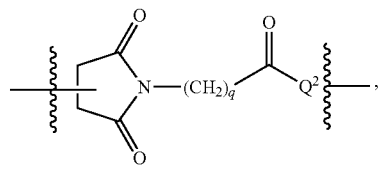

wherein $Q^2$ is NH or O and q is an integer from 1 to 10. In certain instance, q is a number from 2 to 5, such as 2, 3, 4, or 5.

In certain embodiments, A is

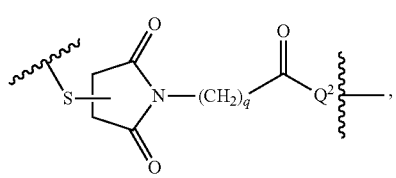

wherein $Q^2$ is NH or O and q is an integer from 1 to 10. In certain instance, q is a number from 2 to 5, such as 2, 3, 4, or 5.

In certain embodiments, A is selected from

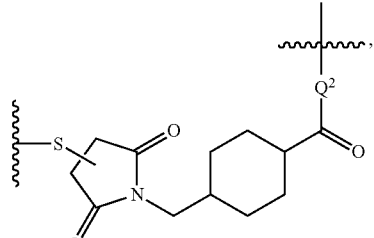

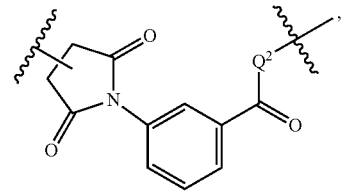

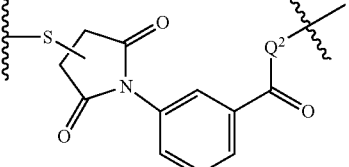

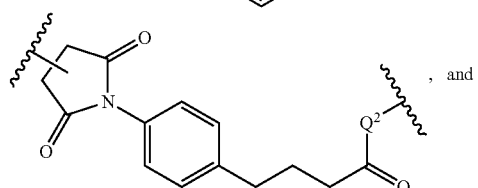

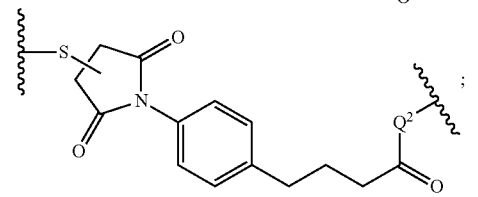

wherein $Q^2$ is NH or O.

Drug Moiety

The drug conjugates of the present embodiments are effective for the usual purposes for which the corresponding drugs are effective, and have superior efficacy because of the ability, inherent in the targeting moiety, to transport the drug to the desired cell where it is of particular benefit.

The preferred drugs for use in the present embodiments are cytotoxic drugs, such as those which are used for cancer therapy. Such drugs include, in general, DNA damaging agents, anti-metabolites, natural products and their analogs. Certain classes of cytotoxic agents include, for example, enzyme inhibitors such as dihydrofolate reductase inhibitors, thymidylate synthase inhibitors, DNA intercalators, DNA cleavers, topoisomerase inhibitors, the anthracycline family of drugs, the vinca drugs, the mitomycins, the bleomycins, the cytotoxic nucleosides, the pteridine family of drugs, diynenes, the podophyllotoxins, differentiation inducers, and taxols. Certain useful members of those classes include, for example, methotrexate, methopterin, dichloromethotrexate, 5-fluorouracil, 6-mercaptopurine, cytosine arabinoside, melphalan, leurosine, leurosideine, actinomycin, daunorubicin, doxorubicin, mitomycin C, mitomycin A, carminomycin, aminopterin, tallysomycin, podophyllotoxin and podophyllotoxin derivatives such as etoposide or etoposide phosphate, vinblastine, vincristine, vindesine, taxol, taxotere retinoic acid, butyric acid, $N^8$-acetyl spermidine, camptothecin, and their analogues. Other drugs include dolastatin and duocarmycin.

One skilled in the art may make chemical modifications to the desired compound in order to make reactions of that compound more convenient for purposes of preparing conjugates of the invention.

In certain embodiments, D is a drug moiety having a chemically reactive functional group by means of which the drug is bonded to $L^1$ or X. In certain instances, the functional group is selected from a primary amine, a secondary amine, hydroxyl, and sulfhydryl. In certain instances, the functional group is a primary amine or a secondary amine. In certain instances, the functional group is hydroxyl. In certain instances, the functional group is sulfhydryl.

As discussed above, the hydrophilic self-immolative linker will typically terminate with an oxycarbonyl group (—O—C(O)—). Thus, an amino-containing drug moiety would readily react with the oxycarbonyl group to form a carbamate group. In certain embodiments, D is an amino-containing drug moiety, wherein the drug is connected to $L^1$ or X through the amino group.

However, if the drug moiety does not contain an amino group, the second self-immolative linker or cyclization self-elimination linker of $L^1$ can provide design potential for a wider variety of moieties that can be used. In certain embodiments, D is a hydroxyl-containing or sulfhydryl-containing drug moiety, wherein the drug is connected to $L^1$ through the hydroxyl or sulfhydryl group.

Representative amino-containing drugs include mitomycin-C, mitomycin-A, daunorubicin, doxorubicin, aminopterin, actinomycin, bleomycin, 9-amino camptothecin, $N^8$-acetyl spermidine, 1-(2-chloroethyl)-1,2-dimethanesulfonyl hydrazide, tallysomycin, cytarabine, dolastatin and derivatives thereof. Amino-containing drugs also include amino derivatives of drugs that do not naturally contain an amino group. In certain embodiments, D is duocarmycin, dolastatin, tubulysin, doxorubicin, paclitaxel, or mitomycin C (MMC), or amino derivatives thereof.

Representative hydroxyl-containing drugs include etoposide, camptothecin, taxol, esperamicin, 1,8-dihydroxy-bicyclo[7.3.1]trideca-4-9-diene-2,6-diyne-13-one, (U.S. Pat. No. 5,198,560), podophyllotoxin, anguidine, vincristine, vinblastine, morpholine-doxorubicin, n-(5,5-diacetoxy-pentyl) doxorubicin, duocarmycin, and derivatives thereof.

Representative sulfhydryl-containing drugs include esperamicin and 6-mercaptopurine, and derivatives thereof.

A certain group of cytotoxic agents for use as drugs in the present embodiments include drugs of the following formulae:

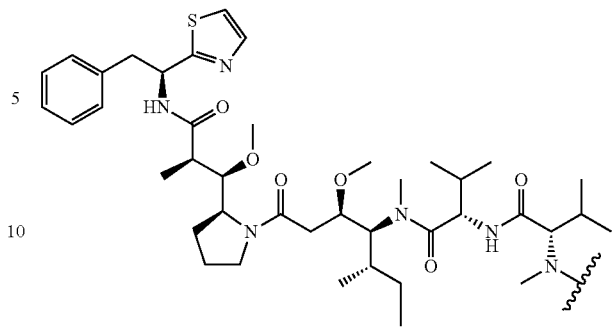

(amino derivative of dolastatin)

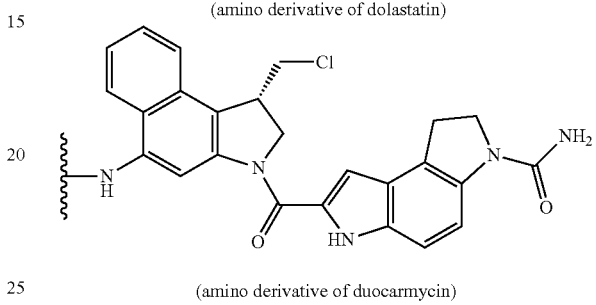

(amino derivative of duocarmycin)

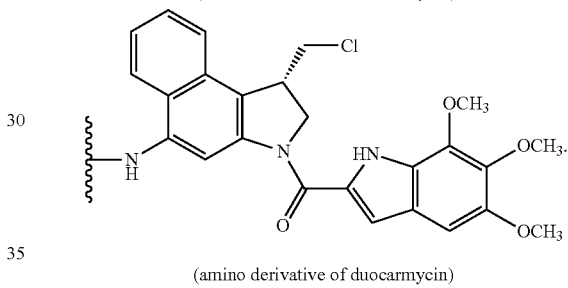

(amino derivative of duocarmycin)

Targeting Moiety

A targeting moiety as described in the present disclosure refers to a moiety or molecule that specifically binds, complexes with, reacts with, or associates with a given cell population (e.g., a FRA expressing cells). In a conjugate described herein, a targeting moiety described herein is linked via a linker to a drug moiety in the conjugate. In some embodiments, the targeting moiety is capable of delivering a drug moiety (e.g., a drug moiety used for therapeutic purpose) to a particular target cell population which the targeting moiety binds, complexes with, reacts with, or associates with.

In some embodiments, the targeting moiety is an antibody (or an antibody moiety or an antibody targeting moiety). In some embodiments, the targeting moiety comprises sulfhydryl (—SH) group (e.g., a free reactive sulfhydryl (—SH) group) or can be modified to contain such a sulfhydryl group. In some embodiments, the targeting moiety comprises an antibody with a sulfhydryl group (e.g., a free reactive sulfhydryl group). In some embodiments, the targeting moiety comprises a free thiol group such as an antibody with a free thiol group or can be modified to contain such a thio group. In some embodiments, the targeting moiety comprising a sulfhydryl group or thiol group bonds to a linker via the sulfur atom in the sulfhydryl group.

In some embodiments, the targeting moiety (e.g., an antibody targeting moiety) has one or more attachment sites for linking to the drug moiety. For example, a targeting moiety T (e.g., an antibody) can have multiple sites (e.g., multiple sulfhydryl groups) for linking to a linker-drug moiety (e.g., A-$L^4$-$L^3$-$L^2$-X-$L^1$-D where A is suitable for bonding to a sulfhydryl group of the targeting antibody). In some embodiments, the targeting moiety can have 1 to 20 sites of attachment. In some embodiments, the targeting moiety can have 1 to 20, 1 to 10, 1 to 8, 1 to 6, 1 to 4, 2 to 8, 2 to 6, or 2 to 4 sites of attachment. In some embodiments, the targeting moiety has 1, 2, 3, 4, 5, 6, 7, or 8 sites of attachment. In some embodiments, the targeting moiety has 2 sites of attachment. In some embodiments, the targeting moiety has 1 site of attachment. In some embodiments, the targeting moiety has 4 sites of attachment. In some instances, certain potential sites of attachment may not be accessible for bonding to a drug moiety. Thus, the number of attachment sites in a targeting moiety T may result in a drug conjugate that has fewer number of drug moieties attached than the number of potential sites of attachment. In some embodiments, one or more of the sites of attachment may be accessible for bonding a drug moiety. For example, an antibody targeting moiety can have one or two sulfhydryl groups on each chain of the antibody accessible for bonding to drug moiety via a linker.

An antibody described herein refers to an immunoglobulin molecule capable of specific binding to a target (i.e., FRA) through at least one antigen recognition site, located in the variable region of the immunoglobulin molecule. As used herein, the term "antibody" encompasses not only intact polyclonal or monoclonal antibodies, but also antigen-binding fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

An antibody included or used in a targeting moiety described herein (or an antibody targeting moiety) can encompass monoclonal antibodies, polyclonal antibodies, antibody fragments (e.g., Fab, Fab', F(ab')$_2$, Fv, Fc, etc.), chimeric antibodies, humanized antibodies, human antibodies (e.g., fully human antibodies), single chain (ScFv), bispecific antibodies, multispecific antibodies, mutants thereof, fusion proteins comprising an antibody portion, and any other modified configuration of the immunoglobulin molecule that comprises an antigen recognition site of the required specificity. The antibodies may be murine, rat, camel, human, or any other origin (including humanized antibodies). In some embodiments, an antibody used in a targeting moiety described herein (or an antibody targeting moiety) is any one of the following: bispecific antibody, multispecific, single-chain, bifunctional, and chimeric and humanized molecules having affinity for a polypeptide conferred by at least one hypervariable region (HVR) or complementarity determining region (CDR) of the antibody. Antibodies used in the present disclosure also include single domain antibodies which are either the variable domain of an antibody heavy chain or the variable domain of an antibody light chain. Holt et al., *Trends Biotechnol.* 21:484-490, 2003. Methods of making domain antibodies comprising either the variable domain of an antibody heavy chain or the variable domain of an antibody light chain, containing three of the six naturally occurring HVRs or CDRs from an antibody, are also known in the art. See, e.g., Muyldermans, *Rev. Mol. Biotechnol.* 74:277-302, 2001.

In some embodiments, an antibody included or used in a targeting moiety described herein (or an antibody targeting moiety) is a monoclonal antibody. As used herein, a monoclonal antibody refers to an antibody of substantially homogeneous antibodies, i.e., the individual antibodies comprising the population are identical except for possible naturally-occurring mutations that may be present in minor amounts. Furthermore, in contrast to polyclonal antibody preparations, which typically include different antibodies directed against different determinants (epitopes), monoclonal antibody is not a mixture of discrete antibodies. The modifier "monoclonal" indicates the character of the antibody as being obtained from a substantially homogeneous population of antibodies, and is not to be construed as requiring production of the antibody by any particular method. For example, the monoclonal antibodies used in the present disclosure may be made by the hybridoma method first described by Kohler and Milstein, 1975, Nature, 256:495, or may be made by recombinant DNA methods such as described in U.S. Pat. No. 4,816,567. The monoclonal antibodies may also be isolated from phage libraries generated using the techniques described in McCafferty et al., 1990, Nature, 348:552-554, for example.

In some embodiments, an antibody included or used in a targeting moiety described herein (or an antibody targeting moiety) is a chimeric antibody. As used herein, a chimeric antibody refers to an antibody having a variable region or part of variable region from a first species and a constant region from a second species. An intact chimeric antibody comprises two copies of a chimeric light chain and two copies of a chimeric heavy chain. The production of chimeric antibodies is known in the art (Cabilly et al. (1984), *Proc. Natl. Acad. Sci. USA*, 81:3273-3277; Harlow and Lane (1988), *Antibodies: a Laboratory Manual*, Cold Spring Harbor Laboratory). Typically, in these chimeric antibodies, the variable region of both light and heavy chains mimics the variable regions of antibodies derived from one species of mammals, while the constant portions are homologous to the sequences in antibodies derived from another. One clear advantage to such chimeric forms is that, for example, the variable regions can conveniently be derived from presently known sources using readily available hybridomas or B cells from non-human host organisms in combination with constant regions derived from, for example, human cell preparations. While the variable region has the advantage of ease of preparation, and the specificity is not affected by its source, the constant region being human is less likely to elicit an immune response from a human subject when the antibodies are injected than would the constant region from a non-human source. However, the definition is not limited to this particular example.

In some embodiments, an antibody included or used in a targeting moiety described herein (or an antibody targeting moiety) is a humanized antibody. As used herein, humanized antibodies refer to forms of non-human (e.g. murine) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a HVR or CDR of the recipient are replaced by residues from a HVR or CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported HVR or CDR or framework sequences, but are included to further refine and optimize antibody performance. In general, the humanized antibody will comprise substantially all of at least one, and typically two, variable domains, in which all or substantially all of the HVR or CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Antibodies may have Fc regions modified as described in WO 99/58572. Other forms of humanized antibodies have one or more HVRs or CDRs (one, two, three, four, five, six) which are altered with respect to the original antibody, which are also termed one or more HVRs or CDRs "derived from" one or more HVRs or CDRs from the original antibody.

In some embodiments, an antibody included or used in a targeting moiety described herein (or an antibody targeting moiety) is a human antibody. As used herein, a human antibody means an antibody having an amino acid sequence corresponding to that of an antibody produced by a human and/or has been made using any of the techniques for making human antibodies known in the art. A human antibody used herein includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, Nature Biotechnology, 14:309-314; Sheets et al., 1998, PNAS, (USA) 95:6157-6162; Hoogenboom and Winter, 1991, J. Mol. Biol., 227:381; Marks et al., 1991, J. Mol. Biol., 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g., Cole et al., Monoclonal Antibodies and Cancer Therapy, Alan R. Liss, p. 77 (1985); Boerner et al., 1991, J. Immunol., 147 (1):86-95; and U.S. Pat. No. 5,750,373.

In some embodiments, an antibody included or used in a targeting moiety described herein (or an antibody targeting moiety) specifically binds to a folate receptor alpha (i.e., FRA) (e.g., a human FRA). In some embodiments, an antibody included or used in a targeting moiety described herein (or an antibody targeting moiety) specifically binds to an extracellular domain of FRA (e.g., an extracellular domain of a human FRA). As used herein, "FRA" refers to both wild type sequences and naturally occurring variant sequences. A non-limiting example of a FRA recognized by antibodies of this invention is human FRA (Accession No. P15328).

Provided below is the amino acid sequence of a human folate receptor alpha:

```
(human FRA)
                                           SEQ ID NO: 35
MAQRMTTQLL LLLVWVAVVG EAQTRIAWAR TELLNVCMNA

KHHKEKPGPE DKLHEQCRPW RKNACCSTNT SQEAHKDVSY

LYRFNWNHCG EMAPACKRHF IQDTCLYECS PNLGPWIQQV

DQSWRKERVL NVPLCKEDCE QWWEDCRTSY TCKSNWHKGW

NWTSGFNKCA VGAACQPFHF YFPTPTVLCN EIWTHSYKVS

NYSRGSGRCI QMWFDPAQGN PNEEVARFYA AAMSGAGPWA

AWPFLLSLAL MLLWLLS
```

In some embodiments, the anti-FRA antibody described herein binds to a mature FRA (e.g., a human FRA) expressed on the cell surface of a human cell (e.g., a human cancer cell). In some embodiments, the anti-FRA antibody described herein binds a mature FRA expressed on the cell surface of a human cancer cell (e.g., an ovarian cancer cell, a lung cancer cell, a uterine cancer cell, a testicular choriocarcinoma cell, an ependymoma cell, a mesothelioma cell, a breast cancer cell, a colon cancer cell, or a renal cell carcinoma cell).

Examples of anti-FRA antibodies and their amino acid sequences are provided in Table 1 below.

TABLE 1

| SEQ ID NO. | Description |
| --- | --- |
| 1 | hLK26-IgG1 heavy chain |
| 2 | hLK26-IgG4p heavy chain |
| 3 | hLK26-kappa light chain |
| 4 | 26B3 (mouse) IgG1 heavy chain |
| 5 | 26B3 (mouse) kappa light chain |
| 6 | hMov19-IgG1 heavy chain |
| 7 | hMov19-kappa light chain |
| 8 | hLK26 heavy chain variable region |
| 9 | hLK26 light chain variable region |
| 10 | 26B3 heavy chain variable region |
| 11 | 26B3 light chain variable region |
| 12 | hMov19 heavy chain variable region |
| 13 | hMov19 light chain variable region |

Amino Acid Sequences of anti-FRA antibodies

IgG4p denotes the human IgG4 antibody with mutation of Ser228 to Pro (S228P), which would prevent Fab arm exchange with another IgG4 in vivo Stubenrauch et al., (2010) Drug Metab Dispos. 38(1):84-91.

Underline portions of the sequences shown below denote the sequences of the variable regions. Bolded portions of the sequences shown below denote the CDRs.

```
SEQ ID NO: 1 (hLK26-IgG1 heavy chain):
EVQLVESGGGVVQPGRSLRLSCSASGFTFSGYGLSWVRQAPGKGLEWVA

MISSGGSYTYYADSVKGRFAISRDNAKNTLFLQMDSLRPEDTGVYFCAR

HGDDPAWFAYWGQGTPVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF
```

-continued

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK

SEQ ID NO: 2 (hLK26-IgG4p heavy chain):
EVQLVESGGGVVQPGRSLRLSCSASGFTFSGYGLSWVRQAPGKGLEWVA

MISSGGSYTYYADSVKGRFAISRDNAKNTLFLQMDSLRPEDTGVYFCAR

HGDDPAWFAYWGQGTPVTVSSASTKGPSVFPLAPCSRSTSESTAALGCL

VKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLPPPK

PKDTLMISRTPEVTCVVVDVSQEDPEVQFNWYVDGVEVHNAKTKPREEQ

FNSTYRVVSVLTVLHQDWLNGKEYKCKVSNKGLPSSIEKTISKAKGQPR

EPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLS

LSLGK

SEQ ID NO: 3 (hLK26-kappa light chain):
DIQLTQSPSSLSASVGDRVTITCSVSSSISSNNLHWYQQKPGKAPKPWI

YGTSNLASGVPSRFSGSGSGTDYTFTISSLQPEDIATYYCQQWSSYPYM

YTFGQGTKVEIKRTVAAPSVFIFPPSDEQLKSGTASVVCLLNNFYPREA

KVQWKVDNALQSGNSQESVTEQDSKDSTYSLSSTLTLSKADYEKHKVYA

CEVTHQGLSSPVTKSFNRGEC

SEQ ID NO: 4 (26B3 (mouse) IgG1 heavy chain):
GPELVKPGASVKISCKASDYSFTGYFMNWVMQSHGKSLEWIGRIFPYNG

DTFYNQKFKGRATLTVDKSSSTAHMELRSLASEDSAVYFCARGTHYFDY

WGQGTTLTVSSAKTTPPSVYPLAPGSAAQTNSMVTLGCLVKGYFPEPVT

VTWNSGSLSSGVHTFPAVLQSDLYTLSSSVTVPSSPRPSETVTCNVAHP

ASSTKVDKKIVPRDCGCKPCICTVPEVSSVFIFPPKPKDVLTITLTPKV

TCVVVDISKDDPEVQFSWFVDDVEVHTAQTQPREEQFNSTFRSVSELPI

MHQDWLNGKEFKCRVNSAAFPAPIEKTISKTKGRPKAPQVYTIPPPKEQ

MAKDKVSLTCMITDFFPEDITVEWQWNGQPAENYKNTQPIMNTNGSYFV

YSKLNVQKSNWEAGNTFTCSVLHEGLHNHHTEKSLSHSPGK

SEQ ID NO: 5 (26B3 (mouse) kappa light chain):
PASLSASVGETVTITCRTSENIFSYLAWYQQKQGISPQLLVYNAKTLAE

GVPSRFSGSGSGTQFSLKINSLQPEDFGSYYCQHHYAFPWTFGGGSKLE

IKRADAAPTVSIFPPSSEQLTSGGASVVCFLNNFYPKDINVKWKIDGSE

RQNGVLNSWTDQDSKDSTYSMSSTLTLTKDEYERHNSYTCEATHKTSTS

PIVKSFNRNEC

SEQ ID NO: 6 (hMov19-IgG1 heavy chain):
QVQLVQSGAEVVKPGASVKISCKASGYTFTGYFMNWVKQSPGQSLEWIG

RIHPYDGDTFYNQKFQGKATLTVDKSSNTAHMELLSLTSEDFAVYYCTR

YDGSRAMDYWGQGTTVTVSSASTKGPSVFPLAPSSKSTSGGTAALGCLV

KDYFPEPVTVSWNSGALTSGVHTFPAVLQSSGLYSLSSVVTVPSSSLGT

QTYICNVNHKPSNTKVDKKVEPKSCDKTHTCPPCPAPELLGGPSVFLFP

PKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNY

KTTPPVLDSDGSFFLYSKLTVDKSRWQQGNVFSCSVMHEALHNHYTQKS

LSLSPGK

SEQ ID NO: 7 (hMov19-kappa light chain):
DIVLTQSPLSLAVSLGQPAIISCKASQSVSFAGTSLMHWYHQKPGQQPR

LLIYRASNLEAGVPDRFSGSGSKTDFTLTISPVEAEDAATYYCQQSREY

PYTFGGGTKLEIKRTVAAPSVFIFPPSDEQLKSGTASVVCLLNNFYPRE

AKVQWKVDNALQSGNSQESVTEQDSKDSTYSLSSTLTLSKADYEKHKVY

ACEVTHQGLSSPVTKSFNRGEC

SEQ ID NO: 8 (hLK26 heavy chain variable region)
EVQLVESGGGVVQPGRSLRLSCSASGFTFSGYGLSWVRQAPGKGLEWVA

MISSGGSYTYYADSVKGRFAISRDNAKNTLFLQMDSLRPEDTGVYFCAR

HGDDPAWFAYWGQGTPVTVSS

SEQ ID NO: 9 (hLK26 light chain variable region)
DIQLTQSPSSLSASVGDRVTITCSVSSSISSNNLHWYQQKPGKAPKPWI

YGTSNLASGVPSRFSGSGSGTDYTFTISSLQPEDIATYYCQQWSSYPYM

YTFGQGTKVEIK

SEQ ID NO: 10 (26B3 heavy chain variable region)
GPELVKPGASVKISCKASDYSFTGYFMNWVMQSHGKSLEWIGRIFPYNG

DTFYNQKFKGRATLTVDKSSSTAHMELRSLASEDSAVYFCARGTHYFDY

WGQGTTLTVSS

SEQ ID NO: 11 (26B3 light chain variable region)
PASLSASVGETVTITCRTSENIFSYLAWYQQKQGISPQLLVYNAKTLAE

GVPSRFSGSGSGTQFSLKINSLQPEDFGSYYCQHHYAFPWTFGGGSKLE

IK

SEQ ID NO: 12 (hMov19 heavy chain variable region)
QVQLVQSGAEVVKPGASVKISCKASGYTFTGYFMNWVKQSPGQSLEWIG

RIHPYDGDTFYNQKFQGKATLTVDKSSNTAHMELLSLTSEDFAVYYCTR

YDGSRAMDYWGQGTTVTVSS

SEQ ID NO: 13 (hMov19 light chain variable region)
DIVLTQSPLSLAVSLGQPAIISCKASQSVSFAGTSLMHWYHQKPGQQPR

LLIYRASNLEAGVPDRFSGSGSKTDFTLTISPVEAEDAATYYCQQSREY

PYTFGGGTKLEIK

The CDRs of the anti-FRA antibodies above are provided in Table 2 below.

TABLE 2

| Amino Acid Sequences of CDRs of anti-FRA Antibody | | | |
|---|---|---|---|
| | hLK26 | 26B3 | hMov19 |
| CDR-H1 | GYGLS (SEQ ID NO: 14) | GYFMN (SEQ ID NO: 20) | GYFMN (SEQ ID NO: 26) |

TABLE 2-continued

Amino Acid Sequences of CDRs of anti-FRA Antibody

| | hLK26 | 26B3 | hMov19 |
|---|---|---|---|
| CDR-H2 | MISSGGSYTYYAD SVKG (SEQ ID NO: 15) | RIFPYNGDTFYNQ KFKG (SEQ ID NO: 21) | RIHPYDGDTFYNQ KFQG (SEQ ID NO: 27) |
| CDR-H3 | HGDDPAWFAY (SEQ ID NO: 16) | GTHYFDY (SEQ ID NO: 22) | YDGSRAMDY (SEQ ID NO: 28) |
| CDR-L1 | SVSSSISSNNLH MH (SEQ ID NO: 17) | RTSENIFSYLA (SEQ ID NO: 23) | KASQSVSFAGTSL MH (SEQ ID NO: 29) |
| CDR-L2 | GTSNLAS (SEQ ID NO: 18) | NAKTLAE (SEQ ID NO: 24) | RASNLEA (SEQ ID NO: 30) |
| CDR-L3 | QQWSSYPYMYT (SEQ ID NO: 19) | QHHYAFPWT (SEQ ID NO: 25) | QQSREYPYT (SEQ ID NO: 31) |

Amino acid sequences of heavy chain constant regions are provided below:

(IgG1 heavy chain constant region)
SEQ ID NO: 32
ASTKGPSVFPLAPSSKSTSGGTAALGCLVKDYFPEPVTVSWNSGALTSG

VHTFPAVLQSSGLYSLSSVVTVPSSSLGTQTYICNVNHKPSNTKVDKKV

EPKSCDKTHTCPPCPAPELLGGPSVFLFPPKPKDTLMISRTPEVTCVVV

DVSHEDPEVKFNWYVDGVEVHNAKTKPREEQYNSTYRVVSVLTVLHQDW

LNGKEYKCKVSNKALPAPIEKTISKAKGQPREPQVYTLPPSRDELTKNQ

VSLTCLVKGFYPSDIAVEWESNGQPENNYKTTPPVLDSDGSFFLYSKLT

VDKSRWQQGNVFSCSVMHEALHNHYTQKSLSLSPGK (IgG4p heavy chain constant region)
SEQ ID NO: 33
ASTKGPSVFPLAPCSRSTSESTAALGCLVKDYFPEPVTVSWNSGALTSG

VHTFPAVLQSSGLYSLSSVVTVPSSSLGTKTYTCNVDHKPSNTKVDKRV

ESKYGPPCPPCPAPEFLGGPSVFLFPPKPKDTLMISRTPEVTCVVVDVS

QEDPEVQFNWYVDGVEVHNAKTKPREEQFNSTYRVVSVLTVLHQDWLNG

KEYKCKVSNKGLPSSIEKTISKAKGQPREPQVYTLPPSQEEMTKNQVSL

TCLVKGFYPSDIAVEWESNGQPENNYKTTPPVLDSDGSFFLYSRLTVDK

SRWQEGNVFSCSVMHEALHNHYTQKSLSLSLGK (kappa light chain constant region)
SEQ ID NO: 34
RTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPV

TKSFNRGEC

In some embodiments, the anti-FRA antibody is antibody hLK26, hMov19, or an antibody derived from any of these antibodies. In some embodiments, the anti-FRA antibody is antibody 26B3 or an antibody derived from antibody 26B3 (e.g., such as a humanized or chimeric antibody). The light chain and heavy chain variable sequences of antibody hLK26, hMov19, and 26B3 are set forth above in Table 1. In some embodiments, the anti-FRA antibody comprises one, two, or three HVRs (or CDRs) from a light chain and/or a heavy chain of the antibody hLK26 or hMov19 (or an antibody derived from any one of these antibodies). In some embodiments, the anti-FRA antibody comprises one, two, or three HVRs (or CDRs) from a light chain or a heavy chain of the antibody hLK26 or hMov19 (or an antibody derived from any one of these antibodies), such as the CDR sequences set forth above in Table 2. In some embodiments, the anti-FRA antibody comprises one, two, or three HVRs (or CDRs) from a light chain and a heavy chain of the antibody hLK26 or hMov19 (or an antibody derived from any one of these antibodies), such as the CDR sequences set forth above in Table 2. In some embodiments, the anti-FRA antibody comprises one, two, or three HVRs (or CDRs) from a light chain and/or a heavy chain of antibody 26B3 or an antibody derived from antibody 26B3 (e.g., such as a humanized or chimeric antibody). In some embodiments, the anti-FRA antibody comprises one, two, or three HVRs (or CDRs) from a light chain or a heavy chain of antibody 26B3 or an antibody derived from antibody 26B3 (e.g., such as a humanized or chimeric antibody), such as the CDR sequences set forth above in Table 2. In some embodiments, the anti-FRA antibody comprises one, two, or three HVRs (or CDRs) from a light chain and a heavy chain of antibody 26B3 or an antibody derived from antibody 26B3 (e.g., such as a humanized or chimeric antibody), such as the CDR sequences set forth above in Table 2. In some embodiments, the anti-FRA antibody comprises a fragment or a region of the antibody hLK26 or hMov19. In some embodiments, the anti-FRA antibody comprises a fragment or a region of an antibody derived from the antibody 26B3 (e.g., such as a humanized or chimeric antibody). In one embodiment, the fragment comprises a light chain variable region of the antibody hLK26 or hMov19. In one embodiment, the fragment comprises a light chain variable region of antibody 26B3 or an antibody derived from antibody 26B3 (e.g., such as a humanized or chimeric antibody). In another embodiment, the fragment comprises a heavy chain variable region of the antibody hLK26 or hMov19. In another embodiment, the fragment comprises a heavy chain variable region of antibody 26B3 or an antibody derived from antibody 26B3 (e.g., such as a humanized or chimeric antibody). In some embodiments, the anti-FRA antibody comprises light chain and heavy chain variable regions of the antibody hLK26 or hMov19. In some embodiments, the anti-FRA antibody comprises light chain and heavy chain variable regions of antibody 26B3 or an antibody derived from antibody 26B3 (e.g., such as a humanized or chimeric antibody). In yet another embodiment, the fragment comprises one, two, or three HVRs (or CDRs) from a light chain and/or a heavy chain of the antibody hLK26, 26B3, or hMov19. In yet another embodiment, the fragment comprises one, two, or three HVRs (or CDRs) from a light chain or a heavy chain of the antibody hLK26, 26B3, or hMov19. In yet another embodiment, the fragment comprises one, two, or three HVRs (or CDRs) from a light chain and a heavy chain of the antibody hLK26, 26B3, or hMov19. In some embodiments, the one or more HVRs (or CDRs) derived from antibody hLK26, 26B3, or hMov19 are at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to at least one, at least two, at least three, at least four, at least five, or at least six HVRs (or CDRs) of hLK26, 26B3, or hMov19.

In some embodiments, the anti-FRA antibody comprises a heavy chain variable region comprising one, two or three HVRs (or CDRs) from SEQ ID NO:8 and/or a light chain variable region comprising one, two or three HVRs (or CDRs) from SEQ ID NO:9. In some embodiments, the anti-FRA antibody comprises a heavy chain variable region comprising one, two or three HVRs (or CDRs) from SEQ ID NO:8. In some embodiments, the anti-FRA antibody comprises a light chain variable region comprising one, two or three HVRs (or CDRs) from SEQ ID NO:9. In some embodiments, the anti-FRA antibody comprises a heavy chain variable region comprising one, two or three HVRs (or CDRs) from SEQ ID NO:8 and a light chain variable region comprising one, two or three HVRs (or CDRs) from SEQ ID NO:9. In some embodiments, the anti-FRA antibody comprises a heavy chain variable region comprising one, two or three HVRs (or CDRs) selected from SEQ ID NOs: 14-16. In some embodiments, the anti-FRA antibody comprises a light chain variable region comprising one, two or three HVRs (or CDRs) selected from SEQ ID NOs:17-19. In some embodiments, the anti-FRA antibody comprises a heavy chain variable region comprising one, two or three HVRs (or CDRs) selected from SEQ ID NOs: 14-16, and a light chain variable region comprising one, two or three HVRs (or CDRs) selected from SEQ ID NOs:17-19. In some embodiments, the antibody comprises a heavy chain variable region comprising the three HVRs (or CDRs) from SEQ ID NO:8 and/or a light chain variable region comprising the three HVRs (or CDRs) from SEQ ID NO:9. In some embodiments, the antibody comprises a heavy chain variable region comprising the three HVRs (or CDRs) from SEQ ID NO:8. In some embodiments, the antibody comprises a light chain variable region comprising the three HVRs (or CDRs) from SEQ ID NO:9. In some embodiments, the antibody comprises a heavy chain variable region comprising the three HVRs (or CDRs) from SEQ ID NO:8 and a light chain variable region comprising the three HVRs (or CDRs) from SEQ ID NO:9. In some embodiments, the anti-FRA antibody comprises a heavy chain variable region comprising the heavy chain variable region (VH) CDR1 sequence set forth in SEQ ID NO:14, the VH CDR2 sequence set forth in SEQ ID NO:15, and the VH CDR3 sequence set forth in SEQ ID NO:16. In some embodiments, the anti-FRA antibody comprises a light chain variable region comprising the light chain variable region (VL) CDR1 sequence set forth in SEQ ID NO:17, the VL CDR2 sequence set forth in SEQ ID NO:18, and the VL CDR3 sequence set forth in SEQ ID NO:19. In some embodiments, the anti-FRA antibody comprises a heavy chain variable region comprising the VH CDR1 sequence set forth in SEQ ID NO:14, the VH CDR2 sequence set forth in SEQ ID NO:15, and the VH CDR3 sequence set forth in SEQ ID NO:16, and a light chain variable region comprising the VL CDR1 sequence set forth in SEQ ID NO:17, the VL CDR2 sequence set forth in SEQ ID NO:18, and the VL CDR3 sequence set forth in SEQ ID NO:19.

In some embodiments, the antibody comprises a heavy chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:8, and/or a light chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:9. In some embodiments, the antibody comprises a heavy chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:8, or a light chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:9. In some embodiments, the antibody comprises a heavy chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:8, and a light chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:9. In some embodiments, the antibody comprises a heavy chain variable region comprising the amino acid sequence of SEQ ID NO:8 and/or a light chain variable region comprising amino acid sequence of SEQ ID NO:9. In some embodiments, the antibody comprises a heavy chain variable region comprising the amino acid sequence of SEQ ID NO:8. In some embodiments, the antibody comprises a light chain variable region comprising amino acid sequence of SEQ ID NO:9. In some embodiments, the antibody comprises a heavy chain variable region comprising the amino acid sequence of SEQ ID NO:8 and a light chain variable region comprising amino acid sequence of SEQ ID NO:9.

In some embodiments, the antibody comprises a heavy chain comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:1 or SEQ ID NO:2, and/or a light chain comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:3. In some embodiments, the antibody comprises a heavy chain comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:1 or SEQ ID NO:2, or a light chain comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:3. In some embodiments, the antibody comprises a heavy chain comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:1 or SEQ ID NO:2, and a light chain comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:3. In some embodiments, the antibody comprises a heavy chain comprising the amino acid sequence of SEQ ID NO:1 or 2 and/or a light chain variable region comprising amino acid sequence of SEQ ID NO:3. In some embodiments, the antibody comprises a heavy chain comprising the amino acid sequence of SEQ ID NO:1 or 2. In some embodiments, the antibody comprises a light chain variable region comprising amino acid sequence of SEQ ID NO:3. In some embodiments, the antibody comprises a heavy chain comprising the amino acid sequence of SEQ ID NO:1 or 2 and a light chain variable region comprising amino acid sequence of SEQ ID NO:3. In some embodiments, the antibody is humanized antibody.

In some embodiments, the anti-FRA antibody comprises a heavy chain variable region comprising one, two or three HVRs (or CDRs) from SEQ ID NO:10 and/or a light chain variable region comprising one, two or three HVRs (or CDRs) from SEQ ID NO:11. In some embodiments, the anti-FRA antibody comprises a heavy chain variable region comprising one, two or three HVRs (or CDRs) from SEQ ID NO:10. In some embodiments, the anti-FRA antibody comprises a light chain variable region comprising one, two or three HVRs (or CDRs) from SEQ ID NO:11. In some embodiments, the anti-FRA antibody comprises a heavy chain variable region comprising one, two or three HVRs (or CDRs) from SEQ ID NO:10 and a light chain variable region comprising one, two or three HVRs (or CDRs) from SEQ ID NO:11. In some embodiments, the anti-FRA antibody comprises a heavy chain variable region comprising one, two or three HVRs (or CDRs) selected from SEQ ID NOs: 20-22. In some embodiments, the anti-FRA antibody comprises a light chain variable region comprising one, two or three HVRs (or CDRs) selected from SEQ ID NOs:23-25. In some embodiments, the anti-FRA antibody comprises a heavy chain variable region comprising one, two or three HVRs (or CDRs) selected from SEQ ID NOs: 20-22, and a light chain variable region comprising one, two or three HVRs (or CDRs) selected from SEQ ID NOs:23-25. In some embodiments, the antibody comprises a heavy chain variable region comprising the three HVRs (or CDRs) from SEQ ID NO:10 and/or a light chain variable region comprising the three HVRs (or CDRs) from SEQ ID NO:11. In some embodiments, the antibody comprises a heavy chain variable region comprising the three HVRs (or CDRs) from SEQ ID NO:10. In some embodiments, the antibody comprises a light chain variable region comprising the three HVRs (or CDRs) from SEQ ID NO:11. In some embodiments, the antibody comprises a heavy chain variable region comprising the three HVRs (or CDRs) from SEQ ID NO:10 and a light chain variable region comprising the three HVRs (or CDRs) from SEQ ID NO:11. In some embodiments, the anti-FRA antibody comprises a heavy chain variable region comprising the heavy chain variable region (VH) CDR1 sequence set forth in SEQ ID NO:20, the VH CDR2 sequence set forth in SEQ ID NO:21, and the VH CDR3 sequence set forth in SEQ ID NO:22. In some embodiments, the anti-FRA antibody comprises a light chain variable region comprising the light chain variable region (VL) CDR1 sequence set forth in SEQ ID NO:23, the VL CDR2 sequence set forth in SEQ ID NO:24, and the VL CDR3 sequence set forth in SEQ ID NO:25. In some embodiments, the anti-FRA antibody comprises a heavy chain variable region comprising the VH CDR1 sequence set forth in SEQ ID NO:20, the VH CDR2 sequence set forth in SEQ ID NO:21, and the VH CDR3 sequence set forth in SEQ ID NO:22, and a light chain variable region comprising the VL CDR1 sequence set forth in SEQ ID NO:23, the VL CDR2 sequence set forth in SEQ ID NO:24, and the VL CDR3 sequence set forth in SEQ ID NO:25.

In some embodiments, the antibody comprises a heavy chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:10, and/or a light chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:11. In some embodiments, the antibody comprises a heavy chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:10, or a light chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:11. In some embodiments, the antibody comprises a heavy chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:10, and a light chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:11. In some embodiments, the antibody comprises a heavy chain variable region comprising amino acid sequence of SEQ ID NO:10 and/or a light chain variable region comprising amino acid sequence of SEQ ID NO:11. In some embodiments, the antibody comprises a heavy chain variable region comprising amino acid sequence of SEQ ID NO:10. In some embodiments, the antibody comprises or a light chain variable region comprising amino acid sequence of SEQ ID NO:11. In some embodiments, the antibody comprises a heavy chain variable region comprising amino acid sequence of SEQ ID NO:10 or a light chain variable region comprising amino acid sequence of SEQ ID NO:11.

In some embodiments, the antibody comprises a heavy chain constant region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:32 or 33, and/or a light chain constant region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:34. In some embodiments, the antibody comprises a heavy chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:32 or 33, or a light chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:34. In some embodiments, the antibody comprises a heavy chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:32 or 33, and a light chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:34. In some embodiments, the antibody comprises a heavy chain constant region comprising amino acid sequence of SEQ ID NO: 32 or 33 and/or a light chain constant region comprising amino acid sequence of SEQ ID NO:34. In some embodiments, the antibody comprises a heavy chain constant region comprising amino acid sequence of SEQ ID NO: 32 or 33. In some embodiments, the antibody comprises a light chain constant region comprising amino acid sequence of SEQ ID NO:34. In some embodiments, the antibody comprises a heavy chain constant region comprising amino acid sequence of SEQ ID NO: 32 or 33 and a light chain constant region comprising amino acid sequence of SEQ ID NO:34.

In some embodiments, the antibody is chimeric antibody. In some embodiments, the antibody is humanized antibody.

In some embodiments, the anti-FRA antibody comprises a heavy chain variable region comprising one, two or three HVRs (or CDRs) from SEQ ID NO:12 and/or a light chain variable region comprising one, two or three HVRs (or CDRs) from SEQ ID NO:13. In some embodiments, the anti-FRA antibody comprises a heavy chain variable region comprising one, two or three HVRs (or CDRs) from SEQ ID NO:12. In some embodiments, the anti-FRA antibody comprises a light chain variable region comprising one, two or three HVRs (or CDRs) from SEQ ID NO:13. In some embodiments, the anti-FRA antibody comprises a heavy chain variable region comprising one, two or three HVRs (or CDRs) from SEQ ID NO:12 and a light chain variable region comprising one, two or three HVRs (or CDRs) from SEQ ID NO:13. In some embodiments, the anti-FRA antibody comprises a heavy chain variable region comprising one, two or three HVRs (or CDRs) selected from SEQ ID NOs: 26-28. In some embodiments, the anti-FRA antibody comprises a light chain variable region comprising one, two or three HVRs (or CDRs) selected from SEQ ID NOs:29-31. In some embodiments, the anti-FRA antibody comprises a heavy chain variable region comprising one, two or three HVRs (or CDRs) selected from SEQ ID NOs: 26-28, and a light chain variable region comprising one, two or three HVRs (or CDRs) selected from SEQ ID NOs:29-31. In some embodiments, the antibody comprises a heavy chain variable region comprising the three HVRs (or CDRs) from SEQ ID NO:12 and/or a light chain variable region comprising the three HVRs (or CDRs) from SEQ ID NO:13. In some embodiments, the antibody comprises a heavy chain variable region comprising the three HVRs (or CDRs) from SEQ ID NO:12. In some embodiments, the antibody comprises a light chain variable region comprising the three HVRs (or CDRs) from SEQ ID NO:13. In some embodiments, the antibody comprises a heavy chain variable region comprising the three HVRs (or CDRs) from SEQ ID NO:12 and a light chain variable region comprising the three HVRs (or CDRs) from SEQ ID NO:13. In some embodiments, the anti-FRA antibody comprises a heavy chain variable region comprising the heavy chain variable region (VH) CDR1 sequence set forth in SEQ ID NO:26, the VH CDR2 sequence set forth in SEQ ID NO:27, and the VH CDR3 sequence set forth in SEQ ID NO:28. In some embodiments, the anti-FRA antibody comprises a light chain variable region comprising the light chain variable region (VL) CDR1 sequence set forth in SEQ ID NO:29, the VL CDR2 sequence set forth in SEQ ID NO:30, and the VL CDR3 sequence set forth in SEQ ID NO:31. In some embodiments, the anti-FRA antibody comprises a heavy chain variable region comprising the VH CDR1 sequence set forth in SEQ ID NO:26, the VH CDR2 sequence set forth in SEQ ID NO:27, and the VH CDR3 sequence set forth in SEQ ID NO:28, and a light chain variable region comprising the VL CDR1 sequence set forth in SEQ ID NO:29, the VL CDR2 sequence set forth in SEQ ID NO:30, and the VL CDR3 sequence set forth in SEQ ID NO:31.

In some embodiments, the antibody comprises a heavy chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:12, and/or a light chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:13. In some embodiments, the antibody comprises a heavy chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:12, or a light chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:13. In some embodiments, the antibody comprises a heavy chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:12, and a light chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:13. In some embodiments, the antibody comprises a heavy chain variable region comprising amino acid sequence of SEQ ID NO:12 and/or a light chain variable region comprising amino acid sequence of SEQ ID NO:13. In some embodiments, the antibody comprises a heavy chain variable region comprising amino acid sequence of SEQ ID NO:12. In some embodiments, the antibody comprises a light chain variable region comprising amino acid sequence of SEQ ID NO:13. In some embodiments, the antibody comprises a heavy chain variable region comprising amino acid sequence of SEQ ID NO:12 and a light chain variable region comprising amino acid sequence of SEQ ID NO:13.

In some embodiments, the antibody comprises a heavy chain constant region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:32 or 33, and/or a light chain constant region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:34. In some embodiments, the antibody comprises a heavy chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:32 or 33, or a light chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:34. In some embodiments, the antibody comprises a heavy chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:32 or 33, and a light chain variable region comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:34. In some embodiments, the antibody comprises a heavy chain constant region comprising amino acid sequence of SEQ ID NO: 32 or 33 and/or a light chain constant region comprising amino acid sequence of SEQ ID NO:34. In some embodiments, the antibody comprises a heavy chain constant region comprising amino acid sequence of SEQ ID NO: 32 or 33. In some embodiments, the antibody comprises a light chain constant region comprising amino acid sequence of SEQ ID NO:34. In some embodiments, the antibody comprises a heavy chain constant region comprising amino acid sequence of SEQ ID NO: 32 or 33 and a light chain constant region comprising amino acid sequence of SEQ ID NO:34.

In some embodiments, the antibody comprises a heavy chain comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:6, and/or a light chain comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:7. In some embodiments, the antibody comprises a heavy chain comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:6. In some embodiments, the antibody comprises a light chain comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:7. In some embodiments, the antibody comprises a heavy chain comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:6, and a light chain comprising an amino acid sequence at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identical to the sequence of SEQ ID NO:7. In some embodiments, the antibody comprises a heavy chain comprising the amino acid sequence of SEQ ID NO: 6 and/or a light chain variable region comprising amino acid sequence of SEQ ID NO:7. In some embodiments, the antibody comprises a heavy chain comprising the amino acid sequence of SEQ ID NO: 6. In some embodiments, the antibody comprises a light chain variable region comprising amino acid sequence of SEQ ID NO:7. In some embodiments, the antibody comprises a heavy chain comprising the amino acid sequence of SEQ ID NO: 6 and a light chain variable region comprising amino acid sequence of SEQ ID NO:7. In some embodiments, the antibody is humanized antibody.

In some embodiments, an anti-FRA antibody included or used in a targeting moiety described herein (or an antibody targeting moiety) specifically binds to a FRA (such as a human FRA) expressed by cancer cells (e.g., FRA-positive ovarian cancer cells, lung cancer cells, uterine cancer cells, testicular choriocarcinoma cells, ependymoma cells, mesothelioma cells, breast cancer cells, colon cancer cells, or renal cell carcinoma cells).

As used herein, "percent (%) amino acid sequence identity" and "homology" with respect to a sequence refers to the percentage of amino acid residues in a candidate sequence that are identical with the amino acid residues in the specific sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

In some embodiments, a CDR described herein is Kabat CDR, Chothia CDR, or contact CDR. In some embodiments, the CDR is a Kabat CDR. In some embodiments, the CDR is a Chothia CDR. In other embodiments, the CDR is a combination of a Kabat and a Chothia CDR (also termed "combined CDR" or "extended CDR"). In other words, for any given embodiment containing more than one CDR, the CDRs may be any of Kabat, Chothia, and/or combined. Methods of determining CDRs are known in the field.

A variable region of an antibody refers to the variable region of the antibody light chain or the variable region of the antibody heavy chain, either alone or in combination. Generally, the variable region(s) mediate antigen binding and define specificity of a particular antibody for its particular antigen. The variable regions may have relatively invariant stretches called framework regions (FRs) (e.g., FR of 15-30 amino acids) separated by shorter regions of extreme variability called "hypervariable regions" ("HVR") (e.g., HVRs that are each 9-12 amino acids long). In some embodiments, the variable domains of native heavy and light chains each comprise four FRs, largely adopting a beta-sheet configuration, connected by three hypervariable regions, which form loops connecting, and in some cases forming part of, the beta-sheet structure. The hypervariable regions in each chain may be held together in close proximity by the FRs and, with the hypervariable regions from the other chain, contribute to the formation of the antigen-binding site of antibodies (see Kabat et al., Sequences of Proteins of Immunological Interest. 5th Ed. Public Health Service, National Institutes of Health, Bethesda, Md. (1991)). The constant domains may not be involved directly in binding an antibody to an antigen, but may exhibit various effector functions, such as participation of the antibody in antibody dependent cellular cytotoxicity (ADCC). A constant region of an antibody refers to the constant region of the antibody light chain or the constant region of the antibody heavy chain, either alone or in combination. A constant region of an antibody generally provides structural stability and other biological functions such as antibody chain association, secretion, transplacental mobility, and complement binding, but is not involved with binding to the antigen. The amino acid sequence and corresponding exon sequences in the genes of the constant region will be dependent upon the species from which it is derived; however, variations in the amino acid sequence leading to allotypes will be relatively limited for particular constant regions within a species. The variable region of each chain is joined to the constant region by a linking polypeptide sequence. The linkage sequence is coded by a "J" sequence in the light chain gene, and a combination of a "D" sequence and a "J" sequence in the heavy chain gene.

The term "hypervariable region" ("HVR") when used herein refers to the amino acid residues of an antibody which are responsible for antigen-binding. The hypervariable region generally comprises amino acid residues from a "complementarity determining region" or "CDR" (e.g. around about residues 24-34 (L1), 50-56 (L2) and 89-97 (L3) in the VL, and around about 31-35B (H1), 50-65 (H2) and 95-102 (H3) in the VH (in one embodiment, H1 is around about 31-35); Kabat et al., Sequences of Proteins of Immunological Interest. 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the VL, and 26-32 (H1), 53-55 (H2) and 96-101 (H3) in the VH; Chothia and Lesk J. Mol. Biol. 196:901-917 (1987)). There are multiple ways for determining CDRs, for example, an approach based on cross-species sequence variability (i.e., Kabat et al. Sequences of Proteins of Immunological Interest, (5th ed., 1991, National Institutes of Health, Bethesda Md.)); and an approach based on crystallographic studies of antigen-antibody complexes (Al-lazikani et al. (1997) J. Mol. Biol. 273:927-948)). The HVRs that are Kabat complementarity-determining regions (CDRs) are based on sequence variability and are the most commonly used (Kabat et al., supra). Chothia refers instead to the location of the structural loops (Chothia and Lesk J. Mol. Biol. 196:901-917 (1987)). The AbM HVRs represent a compromise between the Kabat CDRs and Chothia structural loops, and are used by Oxford Molecular's AbM antibody-modeling software. The "contact" HVRs are based on an analysis of the available complex crystal structures. As used herein, a CDR may be a CDR defined by any of the approaches or by a combination of any two or three of the approaches. The CDR may be Kabat CDR, Chothia CDR, or contact CDR. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat numbering) |
| H1 | H31-H35 | H26-H35 | H26-H32 | H30-H35 (Chothia numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to Kabat et al., supra, for each of these extended-HVR definitions.

In some embodiments, the antibody is a cysteine engineered antibody comprising a free cysteine amino acid in the heavy chain or light chain (e.g., heavy chain and/or light chain constant region, and/or heavy chain and/or light chain variable region). Engineering of a free cysteine amino acid in the antibody may provide a reactive electrophilic functionality that may further enable antibody conjugate compounds such as antibody-drug conjugate (ADC) compounds with drug molecules at specific sites (i.e., site-specific conjugation). Examples of cysteine engineered antibodies and means to generate cysteine engineered antibodies are provided by Junutula, J R et al., (2008) Nat. Biotech. 26(8): 925-932; Lyons, A et al., (1990) Prot. Engineering 3(8):703-708; and Stimmel, J B et al., (2000) J. Biol. Chem. 275(39): 30445-30450. In some embodiments, the antibody is engineered to substitute amino acid residues (e.g., naturally occurring amino acids) on the heavy chain (e.g., in the constant region) or light chain (e.g., in the constant region) with one or more cysteine residues provided that the reactive thiol groups of the cysteine residues have little or no impact of antibody folding or assembly and do not significantly alter antigen binding. In some embodiments, the cysteine residues are evaluated for the reactivity of the newly introduced, engineered cysteine thiol groups. The thiol reactivity value is a relative, numerical term in the range of 0 to 1.0 and can be measured for any cysteine engineered antibody. In some embodiments, the thiol reactivity values of cysteine engineered antibodies of the invention are any one of about 0.6 to 1.0; 0.7 to 1.0; or 0.8 to 1.0. Cysteine engineered antibodies for site-specific conjugation of provided by WO 2006/034488, WO 2010/141902, WO 2013/093809, WO 2008/038024, WO 2008/070593, WO 2009/092011, WO 2011/005481 and WO 2011/156328.

A cysteine engineered antibody may be prepared by mutagenizing a nucleic acid sequence of a parent antibody by replacing one or more amino acid residues by cysteine to encode the cysteine engineered antibody; expressing the cysteine engineered antibody; and isolating the cysteine engineered antibody. In some embodiments, the cysteine engineered antibody is an antibody fragment; for example, a Fab, Fab', F(ab')2, Fv, or a single chain (ScFv) antibody. In some embodiments, the antibody is engineered to include one or more cysteine substitutions of amino acid residues T155, S157, S165, T169, T197, T199 and S442 in the heavy chain as well as L201, V205 and T206 in the light chain (EU numbering). In some embodiments of the invention, an antibody described herein (e.g., antibody hLK26, hMov19, or an antibody derived from antibody 26B3, such as a humanized or chimeric antibody) or an antibody derived from any of these antibodies is engineered to comprise one or more free cysteine residues. The engineered cysteine residues are also referred to as "added cysteine residues".

In some embodiments, one or more amino acid residues at any one or more of the following positions of the IgG heavy chain are replaced with a cysteine residue: 40, 43, 84, 88, 103, 112, 113, 114, 115, 131, 132, 133, 134, 135, 136, 137, 138, 139, 161, 168, 172, 234, 235, 237, 239, 246, 249, 265, 267, 269, 270, 276, 278, 282, 283, 284, 287, 289, 292, 293, 297, 298, 299, 300, 302, 303, 312, 314, 315, 318, 320, 324, 326, 327, 330, 332, 333, 334, 335, 336, 337, 339, 345, 347, 354, 355, 356, 358, 359, 360, 361, 362, 370, 373, 376, 378, 380, 382, 383, 384, 386, 388, 398, 390, 392, 393, 400, 401, 404, 411, 413, 414, 416, 418, 419, 421, 422, 428, 431, 432, 437, 438, 439, 440, 442, 443, and 444; numbering according to the EU index of Kabat et al. (1991, NIH Publication 91-3242, National Technical Information Service, Springfield, Va., hereinafter "Kabat").

In some embodiments, one, two, three, four, five, six, seven, eight, nine, or ten or more amino acid residues at any combination of the following positions of the IgG heavy chain are replaced with a cysteine residue: 40, 43, 84, 88, 103, 112, 113, 114, 115, 131, 132, 133, 134, 135, 136, 137, 138, 139, 161, 168, 172, 234, 235, 237, 239, 246, 249, 265, 267, 269, 270, 276, 278, 282, 283, 284, 287, 289, 292, 293, 297, 298, 299, 300, 302, 303, 312, 314, 315, 318, 320, 324, 326, 327, 330, 332, 333, 334, 335, 336, 337, 339, 345, 347, 354, 355, 356, 358, 359, 360, 361, 362, 370, 373, 376, 378, 380, 382, 383, 384, 386, 388, 398, 390, 392, 393, 400, 401, 404, 411, 413, 414, 416, 418, 419, 421, 422, 428, 431, 432, 437, 438, 439, 440, 442, 443, and 444; numbering according to the EU index of Kabat.

In some embodiments, one or more amino acid residues at any one or more of the following positions of the IgG heavy chain (e.g., human IgG1, human IgG2, human IgG3, human IgG4, or human IgG4p) are replaced with a cysteine residue: T155, S157, S165, T169, T197, T199 and S442; numbering according to the EU index of Kabat. The mutation position (EU numbering) and flanking sequences of amino acids are listed in the Table 3 below.

TABLE 3

Mutation Position (EU Numbering) and Flanking Sequences of Amino Acids

| EU numbering | Flanking Sequence | SEQ ID NO: |
|---|---|---|
| T155C (CH1) | GCLVKDYFPEPVCVSWNSGALTSGV (hIgG1~4) | 36 |
| S157C (CH1) | LVKDYFPEPVTVCWNSGALTSGVHT (hIgG1~4) | 37 |
| S165C (CH1) | PVTVSWNSGALTCGVHTFPAVLQSS (hIgG1~4) | 38 |
| T169C (CH1) | SWNSGALTSGVHCFPAVLQSSGLYS (hIgG1~4) | 39 |
| T197C (CH1) | VVTVPSSSLGTQCYICNVNHKPSNT (hIgG1) | 40 |
| | VVTVPSSNGGTQCYTCNVDHKPSNT (hIgG2) | 41 |

TABLE 3-continued

Mutation Position (EU Numbering) and Flanking Sequences of Amino Acids

| EU numbering | Flanking Sequence | SEQ ID NO: |
|---|---|---|
| | VVTVPSSSLGTQCYTCNVNHKPSNT (hIgG3) | 42 |
| | VVTVPSSSLGTKCYTCNVDHKPSNT (hIgG4) | 43 |
| I199C (CH1) | VVTVPSSSLGTQTYCCNVNHKPSNT (hIgG1) | 44 |
| T199C (CH1) | VVTVPSSNFGTQTYCCNVDHKPSNT (hIgG2) | 45 |
| | VVTVPSSSLGTQTYCCNVNHKPSNT (hIgG3) | 46 |
| | VVTVPSSSLGTKTYCCNVDHKPSNT (hIgG4) | 47 |
| S442C (CH3) | EALHNHYTQKSLCLSPGK (hIgG1, hIgG2) | 48 |
| | EALHNRFTQKSLCLSPGK (hIgG3) | 49 |
| | EALHNHYTQKSLCLSLGK (hIgG4) | 50 |

In some embodiments, the anti-FRA antibody described herein comprises a heavy constant region comprising an amino acid sequence of SEQ ID NO: 32 or SEQ ID NO: 33. In some embodiments, the anti-FRA antibody described herein comprises a light constant region comprising an amino acid sequence of SEQ ID NO: 34. In some embodiments, the anti-FRA antibody described herein comprises a heavy constant region comprising an amino acid sequence of SEQ ID NO: 32 or SEQ ID NO: 33 and a light constant region comprising an amino acid sequence of SEQ. ID NO: 34.

Additional positions on IgG heavy chain that can be engineered cysteine for site-specific conjugation include (EU numbering) 118-215, 234-239, 246, 248, 249, 254, 265, 267, 269, 270, 273, 276, 278, 279, 282, 283, 284, 286, 287, 289, 292, 293, 294, 297, 298, 299, 300, 302, 303, 312, 314, 315, 318, 320, 324, 326, 327, 330, 332-337, 339, 341-447 (described in US 2012/0148580 A1; WO 2013/093809 A1; US 2009/0258420 A1; U.S. Pat. No. 7,521,541 B2; U.S. Pat. No. 7,855,275 B2; US 2011/0137017 A1; US 2012/0213705 A1; US 2011/0033378 A1; U.S. Pat. No. 8,455,622 B2).

Additional positions on IgG light chain that can be engineered cysteine for site-specific conjugation include (EU numbering) 108-211 (described in WO 2013/093809 A1; US 2009/0258420 A1; U.S. Pat. No. 7,855,275 B2; U.S. Pat. No. 8,455,622 B2).

In some embodiments, one or more amino acid residues at any one or more of the following positions of the IgG lambda light chain are replaced with a cysteine residue: 7, 15, 20, 22, 25, 43, 110, 111, 125, 144, 149, 155, 158, 161, 168, 185, 188, 189, 191, 197, 205, 206, 207, 208 and 210, according to the EU index of Kabat.

In some embodiments, one, two, three, four, five, six, seven, eight, nine, or ten or more amino acid residues at any combination of the following positions of the IgG lambda light chain are replaced with a cysteine residue: 7, 15, 20, 22, 25, 43, 110, 111, 125, 144, 149, 155, 158, 161, 168, 185, 188, 189, 191, 197, 205, 206, 207, 208 and 210, according to the EU index of Kabat.

In some embodiments, one or more amino acid residues at any one or more of the following positions of the IgG kappa light chain are replaced with a cysteine residue: 7, 15, 20, 22, 25, 43, 110, 111, 144, 168, 183 and 210, according to the numbering of Kabat.

In some embodiments, one, two, three, four, five, six, seven, eight, nine, or ten or more amino acid residues at any combination of the following positions of the IgG kappa light chain are replaced with a cysteine residue: 7, 15, 20, 22, 25, 43, 110, 111, 144, 168, 183 and 210, according to the numbering of Kabat.

In some embodiments, one or more amino acid residues at any one or more of the following positions of the IgG kappa light chain are replaced with a cysteine residue: L201, V205 and T206; numbering according to the EU index of Kabat. The mutation position (EU numbering) and flanking sequences of amino acids are listed in the Table 4 below.

TABLE 4

Mutation Position (EU Numbering) and Flanking Sequences of Amino Acids

| EU numbering | Flanking Sequence | SEQ ID NO: |
|---|---|---|
| L201C (CL) | EVTHQGCSSPVTKSFNRGEC | 51 |
| T206C (CL) | EVTHQGLSSPVCKSFNRGEC | 52 |
| V205C (CL) | EVTHQGLSSPCTKSFNRGEC | 53 |

In some embodiments, the antibody comprises a heavy chain constant region and a light chain constant region, wherein one or more amino acid residues selected from T155, S157, S165, T169, T197, T199, and S442 in the heavy chain constant region or one or more amino acid residues selected from L201 and T206 in the light chain constant region are replaced with a cysteine residue, and wherein the numbering is according to the EU index of Kabat. In some embodiments, the antibody comprises a heavy chain constant region and a light chain constant region, wherein one or more amino acid residues selected from T155, S157, S165, T169, T197, T199, and S442 in the heavy chain constant region and one or more amino acid residues selected from L201 and T206 in the light chain constant region are replaced with a cysteine residue, and wherein the numbering is according to the EU index of Kabat.

In some embodiments, the antibody is isolated. An isolated antibody refers to an antibody which has been identified and separated and/or recovered from a component of its natural environment. In some embodiments, the antibody is substantially pure. The term "substantially pure" may refer to material which is at least 50% pure (i.e., free from contaminants), more preferably at least 90% pure, more preferably at least 95% pure, more preferably at least 98% pure, more preferably at least 99% pure. In some embodiments, the antibody is a monoclonal antibody. In some embodiments, the antibody is a humanized antibody. In some embodiments, the antibody is a chimeric antibody. In some embodiments, the antibody is a human antibody. In some embodiments, the antibody is IgG (such as $IgG_1$, $IgG_2$, or $IgG_4$). In some embodiments, the antibody is human IgG such as human $IgG_1$. In some embodiments, the antibody is a human IgG comprising the IgG4p constant domain.

The antibodies described herein may further include analogs and derivatives that are either modified, i.e., by the covalent attachment of any type of molecule as long as such covalent attachment permits the antibody to retain its antigen binding immunospecificity. For example, the derivatives and analogs of the antibodies include those that have been further modified, e.g., by glycosylation, acetylation, pegylation, phosphylation, amidation, derivatization by known protecting/blocking groups, proteolytic cleavage, linkage to a cellular ligand or other protein, etc. Chemical modifications can be carried out by known techniques, including, but not limited to specific chemical cleavage, acetylation, formulation, etc. Additionally, the analog or derivative can contain one or more unnatural amino acids.

In some embodiments, the antibody targeting moiety T in compounds of formulae (I)-(V), or a salt or solvate or stereoisomer thereof, is an antibody partially conjugated with a drug moiety, such that it may be further linked to additional drug moieties. Thus, in some embodiments, it is intended that a compound of the formula (I) or a salt or solvate or stereoisomer thereof embraces a compound of the formula (Ia) or a salt or solvate or stereoisomer thereof. Likewise, a compound of the formula (II) or a salt or solvate or stereoisomer thereof is intended to embrace a compound of the formula (IIa) or a salt or solvate or stereoisomer thereof; a compound of the formula (III) or a salt or solvate or stereoisomer thereof is intended to embrace a compound of the formula (IIIa) or a salt or solvate or stereoisomer thereof; a compound of the formula (IV) or a salt or solvate or stereoisomer thereof is intended to embrace a compound of the formula (IVa) or a salt or solvate or stereoisomer thereof; and a compound of the formula (V) or a salt or solvate or stereoisomer thereof is intended to embrace a compound of the formula (Va) or a salt or solvate or stereoisomer thereof.

Methods of making a targeting moiety (e.g., an antibody, a polypeptide, a peptide, or non-peptidyl moiety) are known in the art, such as the methods described in U.S. Pat. No. 7,674,605, U.S. Pat. No. 7,982,017, PCT/US2007/013587 (Publication No. WO 2007/146172), or PCT/US2008/087515 (Publication No. WO 2009/079649).

Representative Linkers

In certain instances, the "-A-$L^4$-$L^3$-$L^2$-" or "-A-$L^4$-$L^3$-" portion in the compound of Formula (I), (Ia), (II) or (IIa) is:

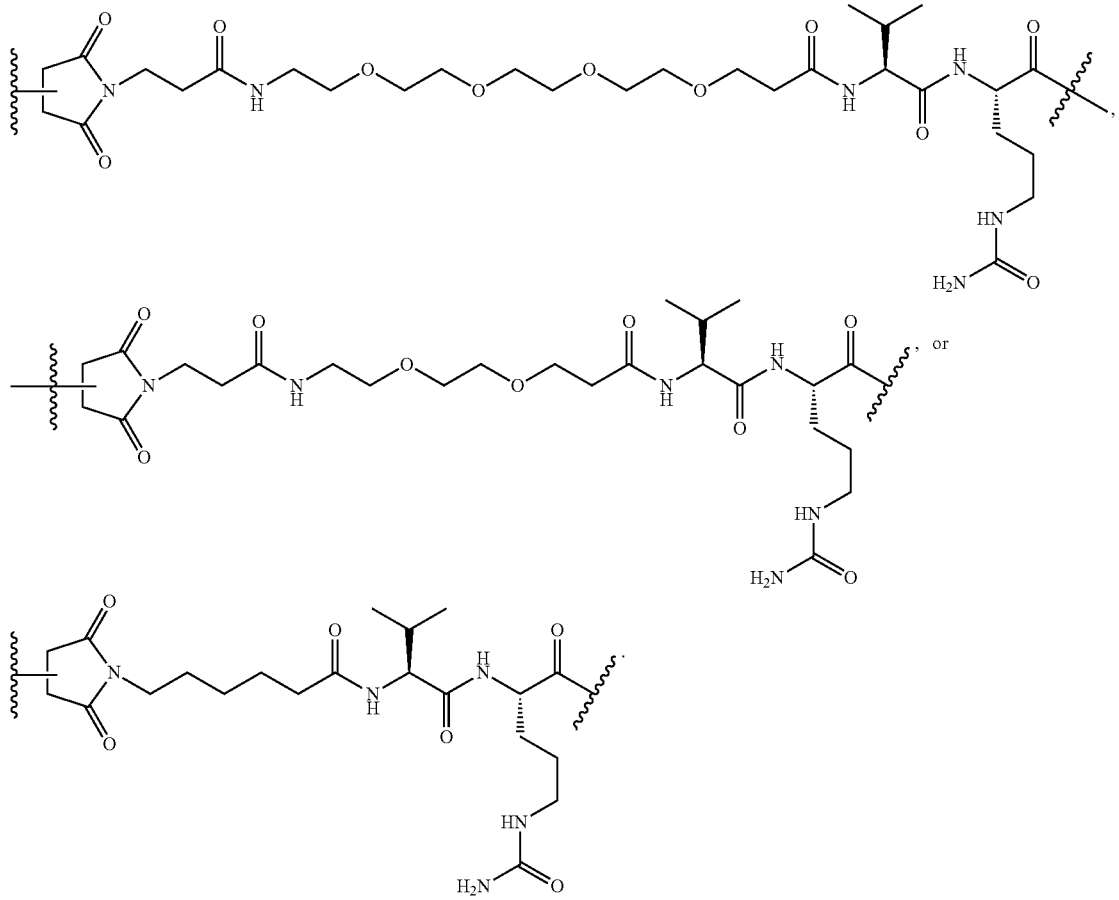

In certain instances, the "-A-$L^4$-$L^3$-$L^2$-" or "-A-$L^4$-$L^3$-" portion in the compound of Formula (I), (Ia), (II) or (IIa) is:

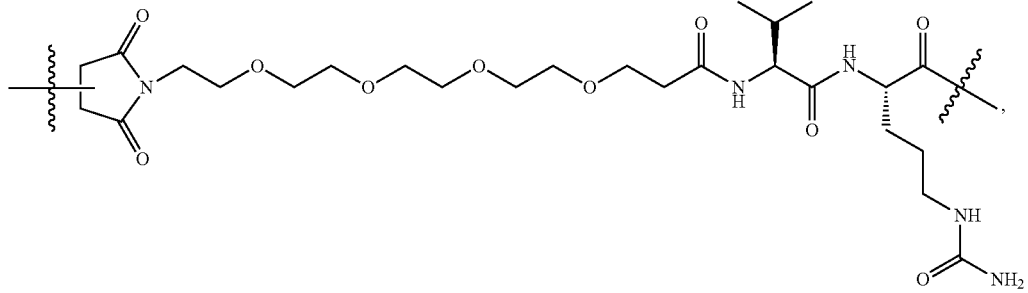

In certain instances, the "-A-L$^4$-L$^3$-L$^2$-" or "-A-L$^4$-L$^3$-" portion in the compound of Formula (I), (Ia), (II) or (IIa) is:
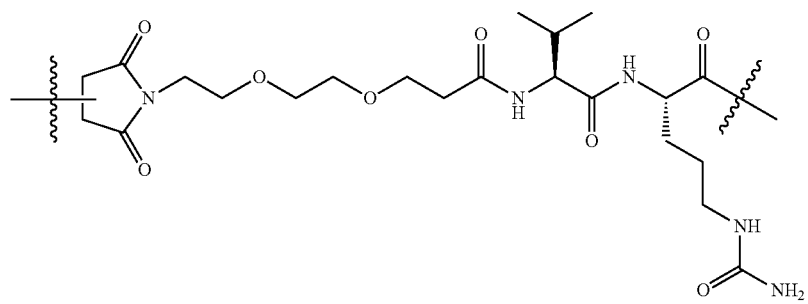
In certain instances, the "-A-L$^4$-L$^3$-L$^2$-X-L$^1$-D" portion in the compound of Formula (I), (Ia), (II) or (IIa) is:
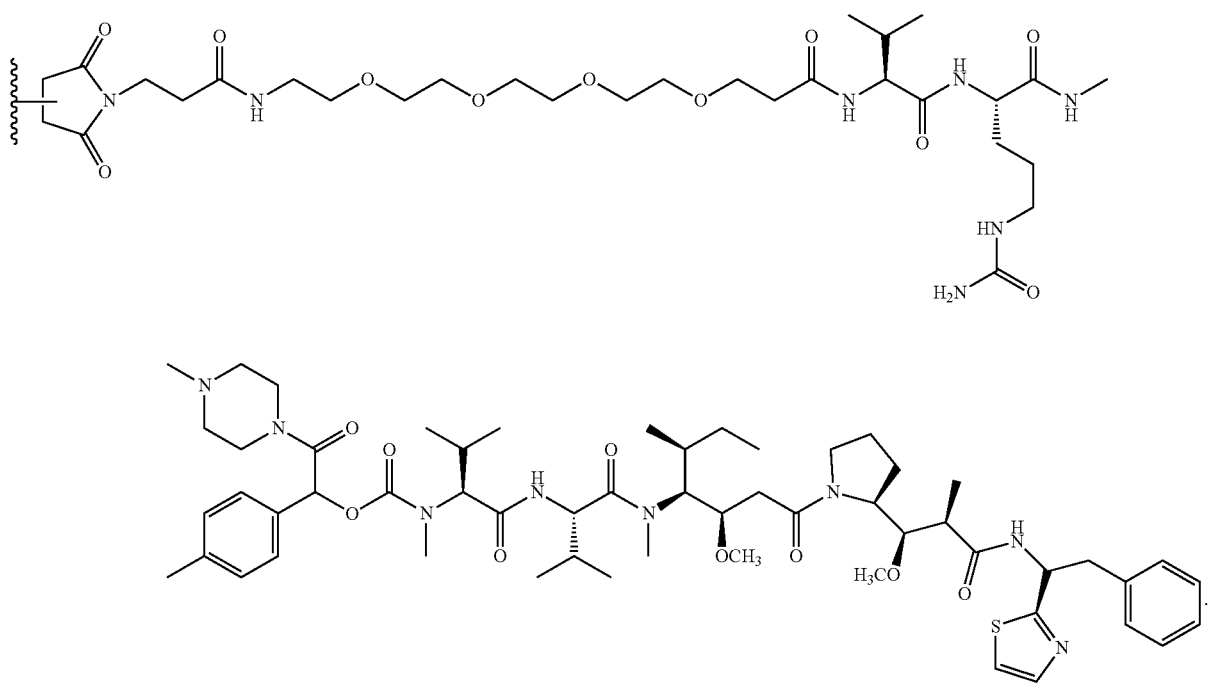
In such instance, the present disclosure provides a compound of Formula (III):
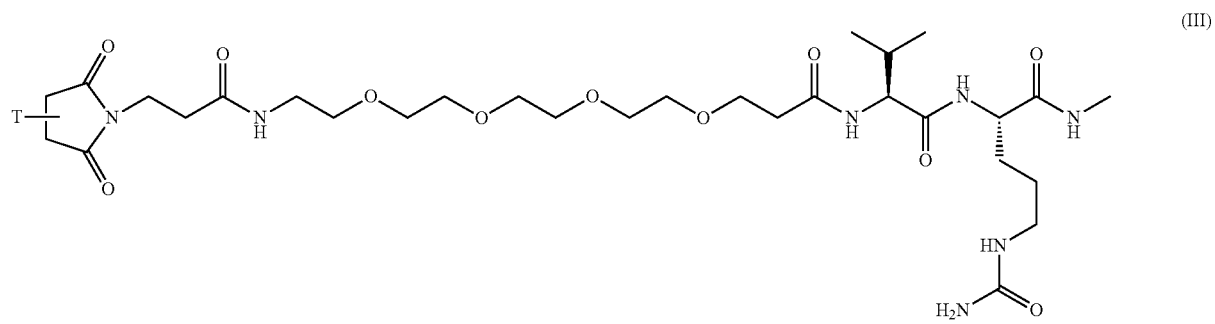
(III)

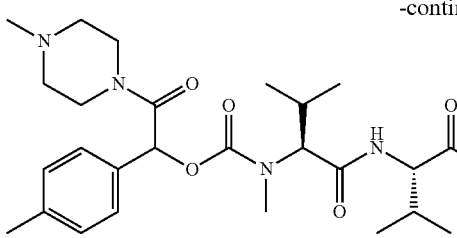

or a salt or solvate or stereoisomer thereof; wherein T is a targeting moiety. In certain instances, in Formula (III), T is an antibody. In some embodiments, T is an anti-FRA antibody. In some embodiments, T is antibody hLK26 or hMOV19. In some embodiments, T is a derivative of antibody 26B3 (e.g., such as a humanized or chimeric antibody).

In some embodiments, provided is a compound of Formula (Ma):

ments, p is 2. In some embodiments, p is 3. In some embodiments, p is 4. In certain instances, in Formula (Ma), T is an antibody, optionally where one or more amino acid residues of the heavy chain and/or the light chain of the antibody are replaced with cysteine residues. In certain embodiments, the antibody is an anti-FRA antibody. In some embodiments, the anti-FRA antibody is hLK26 or hMOV19 or a derivative thereof, or hLK26 where one or more amino

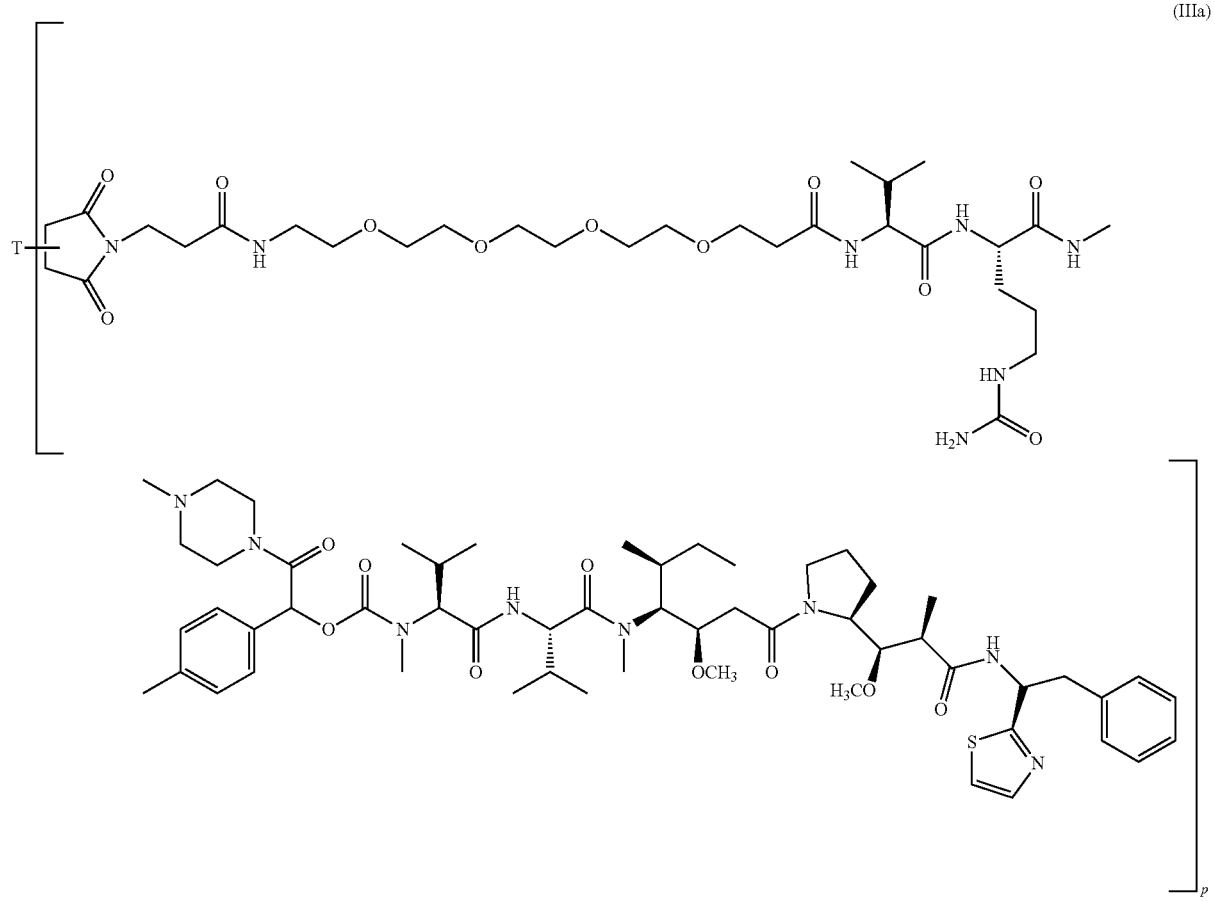

(IIIa)

or a salt or solvate or stereoisomer thereof; wherein T is a targeting moiety and p is 1 to 20. In some embodiments, p is 1 to 8. In some embodiments, p is 1 to 6. In some embodiments, p is 1 to 4. In some embodiments, p is 2 to 4. In some embodiments, p is 1, 2, 3 or 4. In some embodiacid residues of the heavy chain and/or the light chain of the antibody are replaced with cysteine residues, or hMOV19 where one or more amino acid residues of the heavy chain and/or the light chain of the antibody are replaced with cysteine residues. In some embodiments, the anti-FRA antibody is a derivative of 26B3 (e.g., such a humanized or chimeric antibody), or a derivative of 26B3 (e.g., such as a humanized or chimeric antibody) where one or more amino acid residues of the heavy chain and/or the light chain of the antibody are replaced with cysteine residues.

In certain embodiments, a compound of formula (I) or (Ia), such as a compound of formula (III) or (IIIa) can be prepared using synthetic intermediates such as a compound of formula (VI) or a salt or solvate thereof and/or a compound of formula (IX) or a salt or solvate thereof.

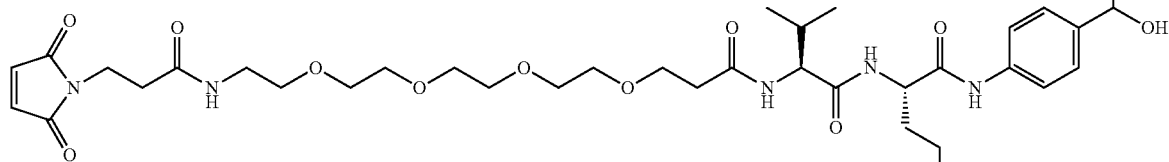

(VI)

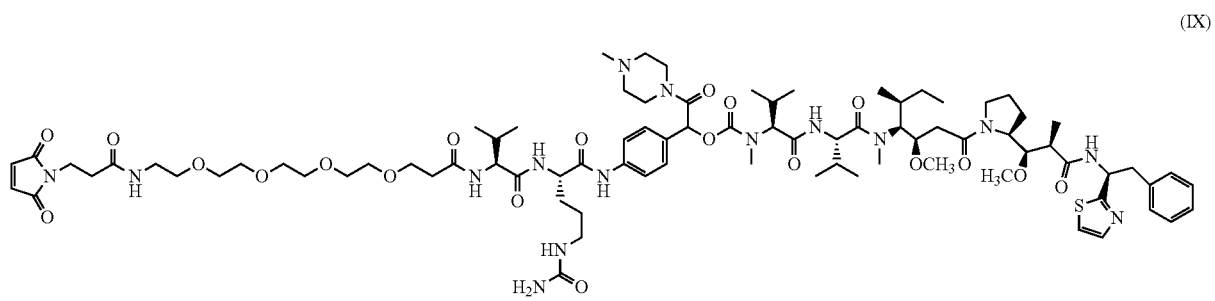

(IX)

In certain instances, the "-A-L$^4$-L$^3$-L$^2$-X-L$^1$-D" portion in the compound of Formula (I), (Ia), (II) or (IIa) is:

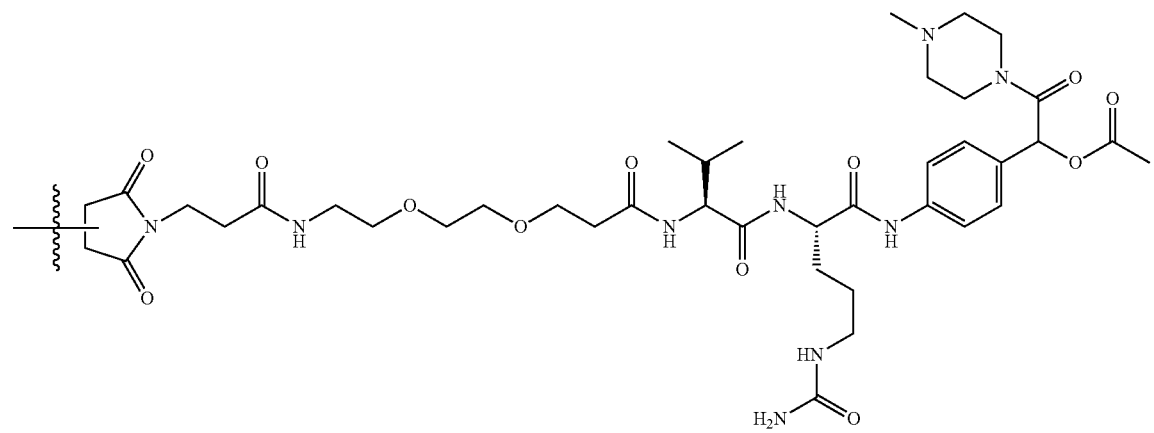

-continued

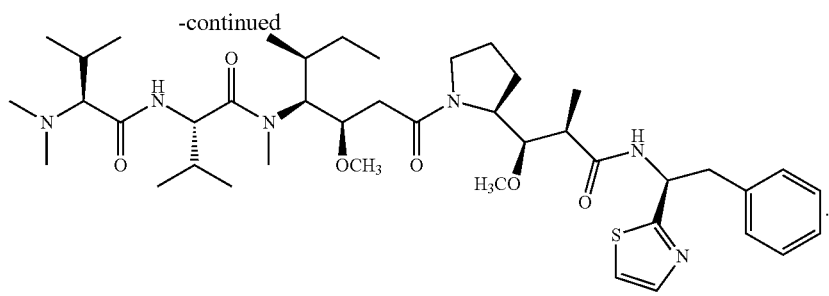

In such instance, the present disclosure provides a compound of Formula (IV):

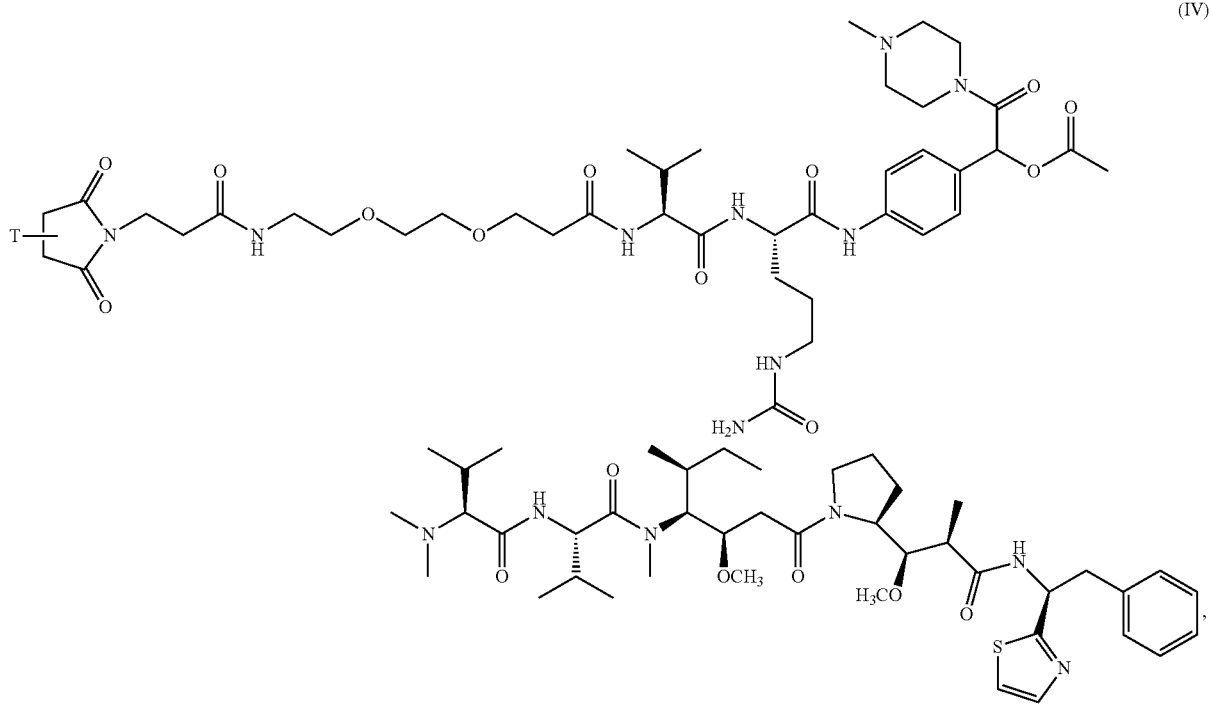

(IV)

or a salt or solvate or stereoisomer thereof; wherein T is a targeting moiety. In certain instances, in Formula (IV), T is an antibody. In some embodiments, T is an anti-FRA antibody. In some embodiments, the antibody is antibody hLK26 or hMOV19. In some embodiments, the antibody is a derivative of antibody 26B3 (e.g., such as a humanized or chimeric antibody).

In some embodiments, provided is a compound of Formula (IVa):

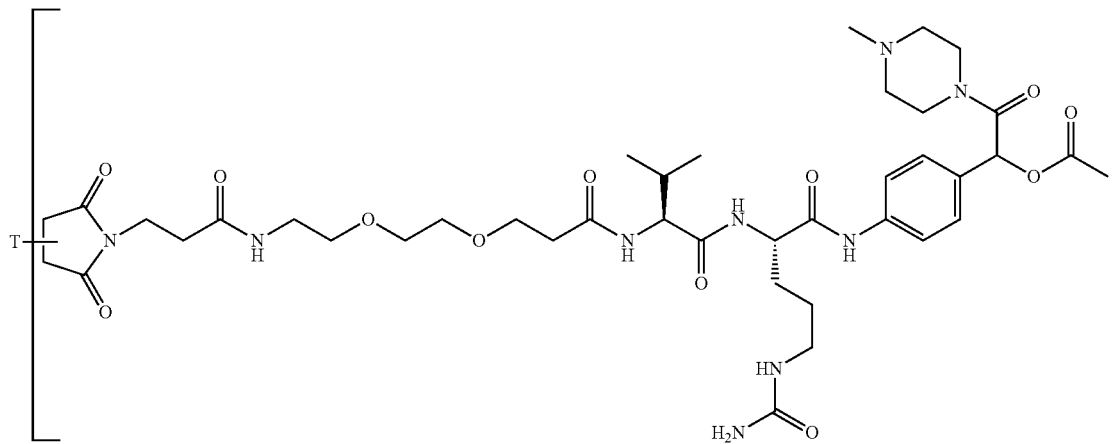

(IVa)

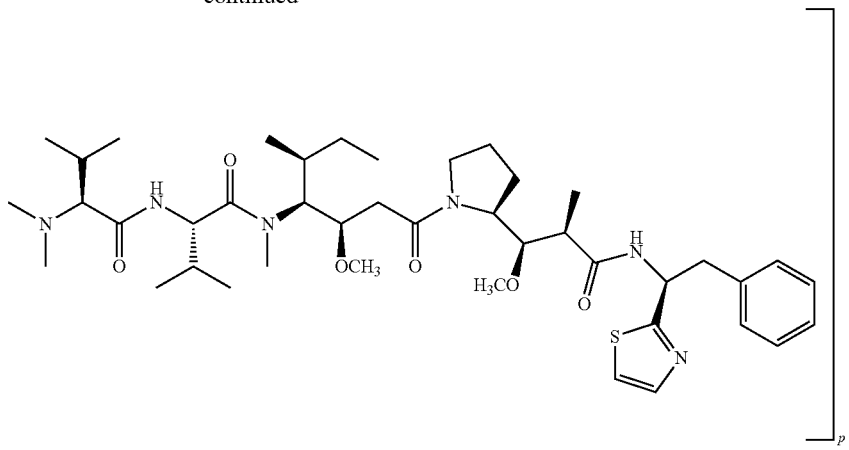

or a salt or solvate or stereoisomer thereof; wherein T is a targeting moiety and p is 1 to 20. In some embodiments, p is 1 to 8. In some embodiments, p is 1 to 6. In some embodiments, p is 1 to 4. In some embodiments, p is 2 to 4. In some embodiments, p is 1, 2, 3 or 4. In some embodiments, p is 2. In some embodiments, p is 3. In some embodiments, p is 4. In certain instances, in Formula (IVa), T is an antibody, optionally where one or more amino acid residues of the heavy chain and/or the light chain of the antibody are replaced with cysteine residues. In some embodiments, the antibody is an anti-FRA antibody. In some embodiments, the antibody is hLK26 or hMOV19 or a derivative thereof, or hLK26 where one or more amino acid residues of the heavy chain and/or the light chain of the antibody are replaced with cysteine residues, or hMOV19 where one or more amino acid residues of the heavy chain and/or the light chain of the antibody are replaced with cysteine residues. In some embodiments, the antibody is a derivative of 26B3 (e.g., such a humanized or chimeric antibody), or a derivative of 26B3 (e.g., such a humanized or chimeric antibody) where one or more amino acid residues of the heavy chain and/or the light chain of the antibody are replaced with cysteine residues.

In certain embodiments, a compound of formula (I) or (Ia), such as a compound of formula (IV) or (IVa) can be prepared using synthetic intermediates such as a compound of formula (VII) or a salt or solvate thereof and/or a compound of formula (X) or a salt or solvate thereof.

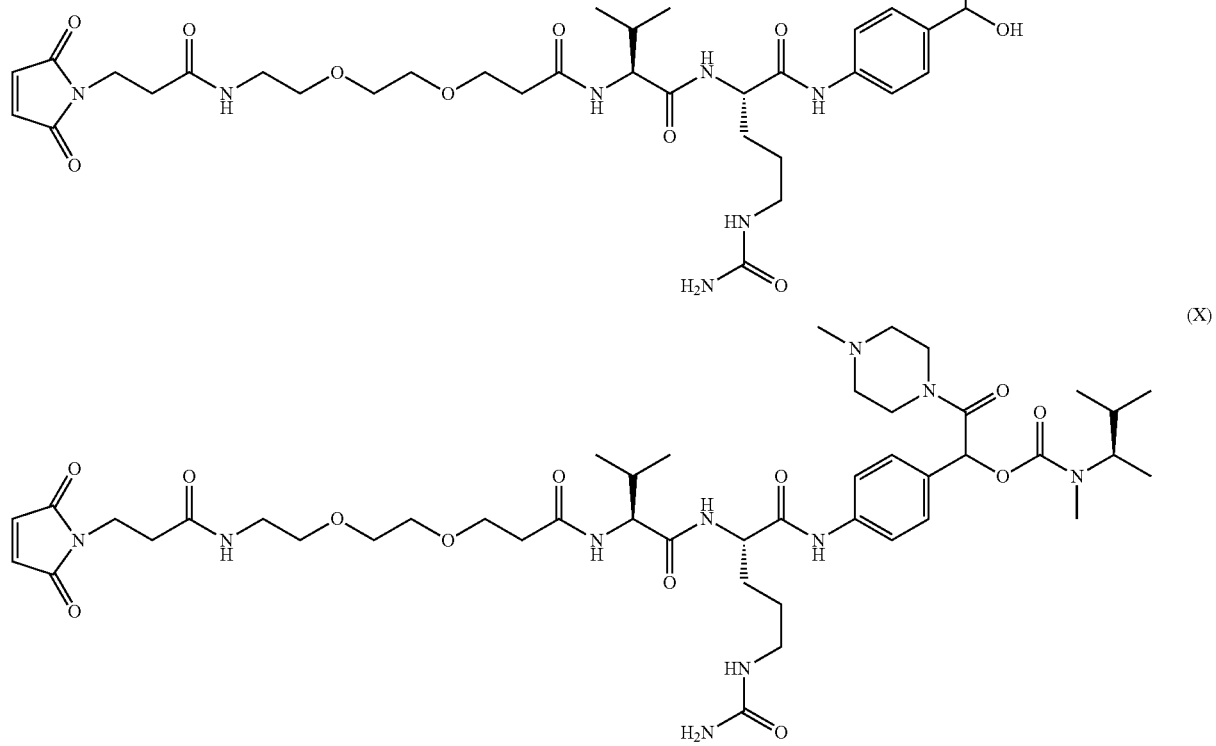

-continued

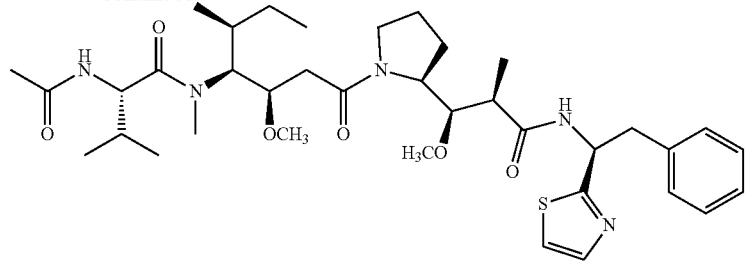

In certain instances, the "-A-L⁴-L³-L²-X-L¹-D" portion in the compound of Formula (I), (Ia), (II) or (IIa) is:

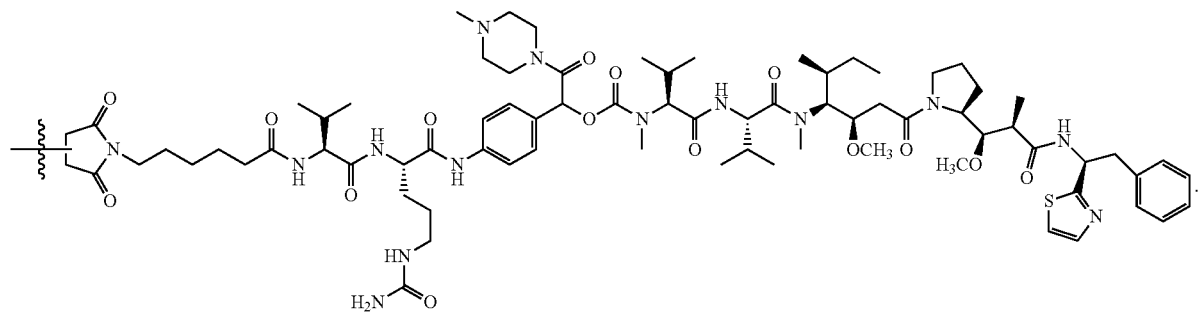

In such instance, the present disclosure provides a compound of Formula (V):

(V)

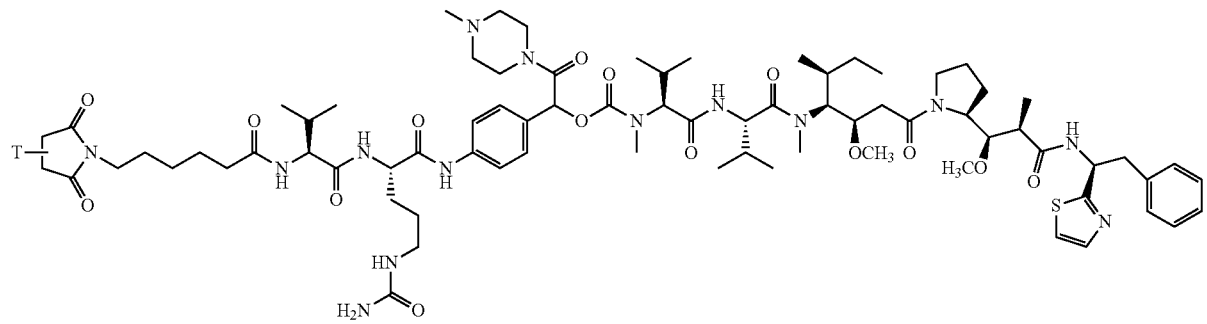

or a salt or solvate or stereoisomer thereof; wherein T is a targeting moiety. In certain instances, in Formula (V), T is an antibody. In some embodiments, the antibody is an anti-FRA antibody. In some embodiments, the antibody is antibody hLK26 or hMOV19. In some embodiments, the antibody is a derivative of antibody 26B3 (e.g., such as a humanized or chimeric antibody).

In some embodiments, provided is a compound of Formula (Va):

(Va)

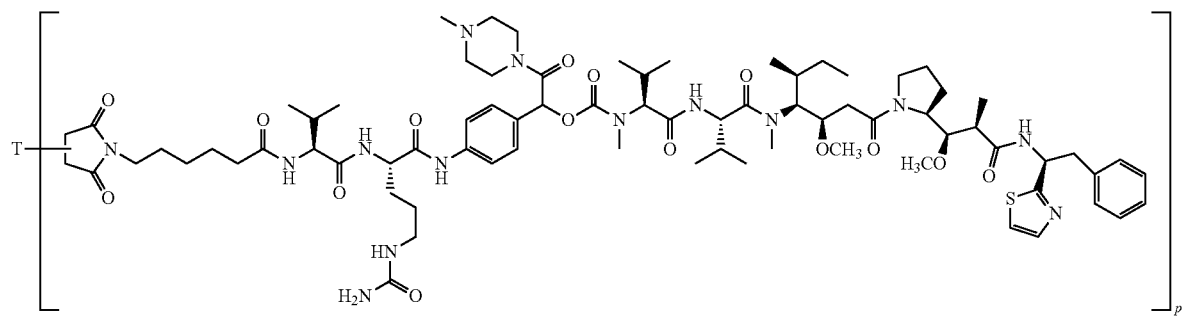

or a salt or solvate or stereoisomer thereof; wherein T is a targeting moiety and p is 1 to 20. In some embodiments, p is 1 to 8. In some embodiments, p is 1 to 6. In some embodiments, p is 1 to 4. In some embodiments, p is 2 to 4. In some embodiments, p is 1, 2, 3 or 4. In some embodiments, p is 2. In some embodiments, p is 3. In some embodiments, p is 4. In certain instances, in Formula (Va), T is an antibody, optionally where one or more amino acid residues of the heavy chain and/or the light chain of the antibody are replaced with cysteine residues. In some embodiments, the antibody is an anti-FRA antibody. In some embodiments, the antibody is hLK26 or hMOV19 or a derivative thereof, or hLK26 where one or more amino acid residues of the heavy chain and/or the light chain of the antibody are replaced with cysteine residues, or hMOV19 where one or more amino acid residues of the heavy chain and/or the light chain of the antibody are replaced with cysteine residues. In some embodiments, the antibody is a derivative of 26B3 (e.g., such a humanized or chimeric antibody), or a derivative of 26B3 (e.g., such as a humanized or chimeric antibody) where one or more amino acid residues of the heavy chain and/or the light chain of the antibody are replaced with cysteine residues.

In certain embodiments, a compound of formula (I) or (Ia), such as a compound of formula (V) or (Va) can be prepared using synthetic intermediates such as a compound of formula (VIII) or a salt or solvate thereof and/or a compound of formula (XI) or a salt or solvate thereof.

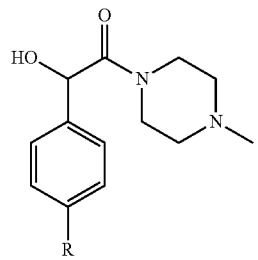

(XII)

or a salt or solvate or stereoisomer thereof; wherein R is $NO_2$ or $NH_2$.

The compounds of Formulae (I)-(V) or (Ia)-(Va) may be prepared and/or formulated as pharmaceutically acceptable salts. Pharmaceutically acceptable salts are non-toxic salts of a free base form of a compound that possesses the desired pharmacological activity of the free base. These salts may be derived from inorganic or organic acids. Non-limiting examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumar-

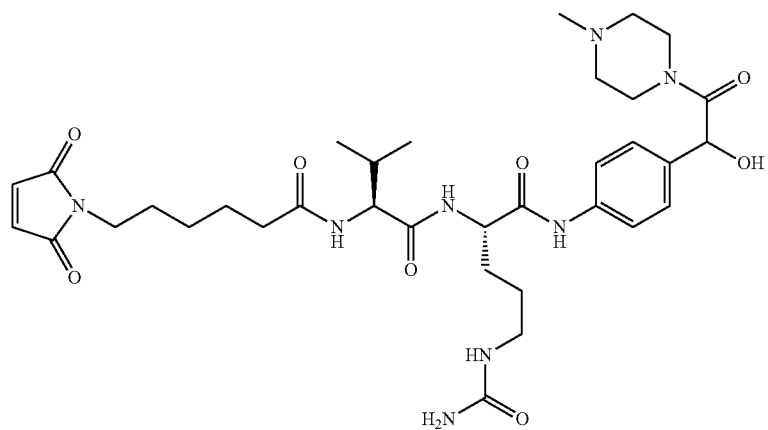

(VIII)

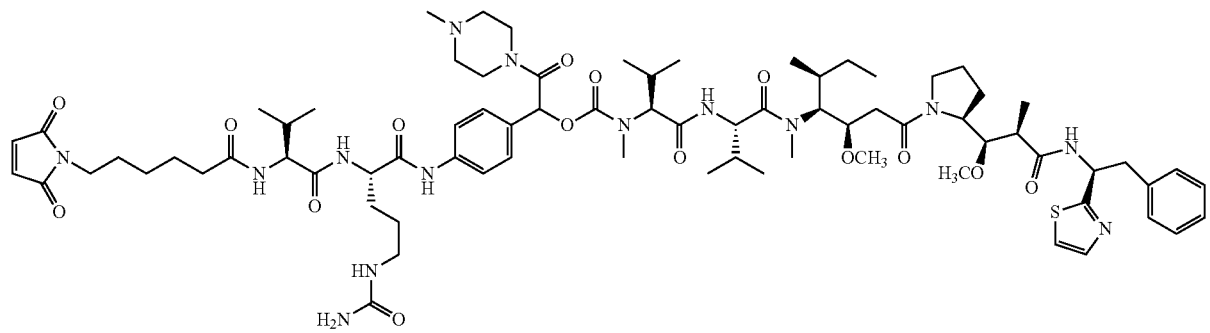

(XI)

In certain embodiments, a compound of formula (I) or (Ia), or any variations described herein, can be prepared using a compound of Formula (XII):

ates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, γ-hydroxybutyrates, glycolates, tartrates, and mandelates. Lists of other suitable pharmaceutically acceptable salts are found in Remington's Pharmaceutical Sciences, 17th Edition, Mack Publishing Company, Easton, Pa., 1985.

For a compound of any one of Formulae (I)-(V) or (Ia)-(Va) that contains a basic nitrogen, a pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, or ethanesulfonic acid, or any compatible mixture of acids such as those given as examples herein, and any other acid and mixture thereof that are regarded as equivalents or acceptable substitutes in light of the ordinary level of skill in this technology.

Also provided are compositions comprising one or more compounds of the formulae (I)-(V) or (Ia)-(Va), or a salt or solvate or stereoisomers thereof. In the compounds of the formulae (I)-(V) or (Ia)-(Va), or a salt or solvate or stereoisomers thereof, the targeting moiety can have one or more sites of attachment for linking to the drug moiety. Depending on the accessibility of the attachment sites in the targeting moiety and the relative concentration of the drug moiety in forming the conjugate, a portion of the attachment sites may not be bonded to a drug moiety in the conjugate formed. A mixture of compounds having various number of drug moieties at each targeting moiety may form. Thus a composition is also provided, comprising one or more compounds of the formulae (Ia)-(Va), or a salt or solvate or stereoisomers thereof. For example, for a targeting molecule having 4 sites of attachment, the composition may comprise one or more compounds selected from a compound of formula (Ia) where p is 1, a compound of formula (Ia) where p is 2, a compound of formula (Ia) where p is 3, and a compound of formula (Ia) where p is 4. The relative amounts of compounds in the composition may be adjusted to achieve a desirable ratio between the drug moiety and the targeting moiety. In some of embodiments, the composition comprises predominantly one or two of the compounds.

The "drug-antibody ratio" (DAR) in a compound or composition of the invention is defined as the molar ratio between the drug moieties in the compound or composition and the antibodies in the compound or composition. Where an antibody has more than one site of attachment, more than one drug moiety may be linked to each antibody. In some instances, a mixture is obtained comprising more than one antibody-drug conjugate (ADC) molecules. The drug-antibody ratios of the antibody-drug conjugates can be measured by analytical methods know in the art, for example, methods as described in Jeffrey, et al., *Bioconjug. Chem.* 24(7):1256-1263 (2013); and Sun et al., *Bioconjug. Chem.* 16(5):1282-1290 (2005). In some embodiments, the composition comprising one or more ADCs of detailed herein has an average DAR of about 0.5 to about 6, about 1 to about 5, about 1 to about 4, about 1.5 to about 3.5, or about 2 to about 4. In some embodiments, the composition has an average DAR of about 1.5 to about 3.5, or about 2 to about 3.5, or about 2.7 to about 3.5, or about 2 to about 3, or about 3 to about 3.3, or about 2, or about 3. In some other preferred embodiments, the composition has an average DAR of about 2.5±10% (for example, about 2.25 to about 2.75). In some embodiments, the targeting antibody contains cysteine engineered sites of attachment and the composition has an average DAR of about 1.6 to about 2.1, or about 2.0.

Pharmaceutical Compositions and Methods of Treatment

For treatment purposes, a pharmaceutical composition of the embodiments comprises at least one compound of Formulae (I)-(V) or (Ia)-(Va), or a pharmaceutically acceptable salt thereof. The pharmaceutical compositions may further comprise one or more pharmaceutically-acceptable excipients or pharmaceutically-acceptable carrier. A pharmaceutically-acceptable excipient is a substance that is non-toxic and otherwise biologically suitable for administration to a subject. Such excipients facilitate administration of the compounds described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the embodiments are sterile compositions. Pharmaceutical compositions may be prepared using compounding techniques known or that become available to those skilled in the art.

Sterile compositions are also contemplated by the embodiments, including compositions that are in accord with national and local regulations governing such compositions.

The pharmaceutical compositions and compounds described herein may be formulated as solutions, emulsions, suspensions, dispersions, or inclusion complexes such as cyclodextrins in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. Pharmaceutical compositions of the embodiments may be administered by a suitable route of delivery, such as oral, parenteral, rectal, nasal, topical, or ocular routes, or by inhalation. Preferably, the compositions are formulated for intravenous or oral administration.

For oral administration, the compounds the embodiments may be provided in a solid form, such as a tablet or capsule, or as a solution, emulsion, or suspension. To prepare the oral compositions, the compounds of the embodiments may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions of the embodiments may be formulated for rectal administration as a suppository. For parenteral use, including intravenous, intramuscular, intraperitoneal, intranasal, or subcutaneous routes, the agents of the embodiments may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the pharmaceutical compositions of the embodiments may be administered using, for example, a spray formulation also containing a suitable carrier.

For topical applications, the compounds of the embodiments are preferably formulated as creams or ointments or a similar vehicle suitable for topical administration. For topical administration, the inventive compounds may be mixed with a pharmaceutical carrier at a concentration of about 0.1% to about 10% of drug to vehicle. Another mode of administering the agents of the embodiments may utilize a patch formulation to effect transdermal delivery.

The present disclosure provides a method of killing a cell that expresses folate receptor alpha (FRA) comprising administering to the cell an effective amount of the compound of Formulae (I)-(V) or (Ia)-(Va) or a salt, a solvate, or a stereoisomer thereof. In some embodiments, there is provided a method of killing a cell that expresses a human folate receptor alpha (FRA), comprising administering to the cell an amount of a compound of Formulae (I)-(V) or (Ia)-(Va) or a salt, a solvate, or a stereoisomer thereof, sufficient to kill the cell. In certain embodiments, the cell is a cancer cell. In certain embodiments, the cancer cell is an ovarian cancer cell, a lung cancer cell, a uterine cancer cell, a testicular choriocarcinoma cell, an ependymoma cell, a mesothelioma cell, a breast cancer cell, a colon cancer cell, or a renal cell carcinoma cell. In certain embodiments, the cancer cell is a FRA-positive ovarian cancer cell, a FRA-positive lung cancer cell, a FRA-positive uterine cancer cell, a FRA-positive testicular choriocarcinoma cell, a FRA-positive ependymoma cell, a FRA-positive mesothelioma cell, a FRA-positive breast cancer cell, a FRA-positive colon cancer cell, or a FRA-positive renal cell carcinoma cell.

In another aspect, the present disclosure provides a method of treating cancer in an individual comprising administering to the individual an effective amount of a compound of Formulae (I)-(V) or (Ia)-(Va) or a salt, a solvate, or a stereoisomer thereof. Examples of cancers that may be treated with the method described herein include, but are not limited to, carcinoma, including adenocarcinoma, lymphoma, blastoma, melanoma, and sarcoma. More particular examples of such cancers include squamous cell cancer, small-cell lung cancer, non-small cell lung cancer, lung adenocarcinoma, lung squamous cell carcinoma, gastrointestinal cancer, Hodgkin's and non-Hodgkin's lymphoma, pancreatic cancer, glioblastoma, cervical cancer, glioma, ovarian cancer, liver cancer such as hepatic carcinoma and hepatoma, bladder cancer, breast cancer, colon cancer, colorectal cancer, endometrial or uterine carcinoma, salivary gland carcinoma, kidney cancer such as renal cell carcinoma and Wilms' tumors, basal cell carcinoma, melanoma, mesothelioma, prostate cancer, thyroid cancer, testicular cancer, esophageal cancer, gallbladder cancer, and various types of head and neck cancer.

In certain embodiments of the method for treating cancer, the cancer is selected from ovarian cancer, lung cancer, uterine cancer, testicular choriocarcinoma, ependymoma, mesothelioma, breast cancer, colon cancer, and renal cell carcinoma. In some embodiments, the cancer is FRA-positive cancer. In certain embodiments, the cancer is a FRA-positive ovarian cancer, a FRA-positive lung cancer, a FRA-positive uterine cancer, a FRA-positive testicular choriocarcinoma, a FRA-positive ependymoma, a FRA-positive mesothelioma, a FRA-positive breast cancer, a FRA-positive colon cancer, or a FRA-positive renal cell carcinoma. In certain embodiments, the individual has cancer or has been diagnosed with cancer. In certain embodiments, the individual has a FRA-positive malignancy or has been diagnosed with a FRA-positive malignancy (such as ovarian cancer, lung cancer, uterine cancer, testicular choriocarcinoma, ependymoma, mesothelioma, breast cancer, colon cancer, or renal cell carcinoma). In certain embodiments, the individual is a human. In some embodiments, the method further comprises a step of detecting the expression level of FRA on cancer cells before administering the compound. In some embodiments, the compound is administered intraperitoneally, intravenously, intramuscularly, subcutaneously, intrathecally, intraventricularly, orally, enterally, parenterally, intranasally, dermally, sublingually, or by inhalation.

Kits

The present disclosure provides a pharmaceutical pack or kit comprising one or more containers comprising a compound of Formulae (I)-(V) or (Ia)-(Va) or a salt, solvate or stereoisomer thereof useful for the treatment or prevention of cancer. The kit can further comprise instructions for use in the treatment of cancer.

The present disclosure also provides a pharmaceutical pack or kit comprising one or more containers comprising one or more of the ingredients of the pharmaceutical compositions of the present embodiments. Optionally associated with such container(s) can be a notice in the form prescribed by a governmental agency regulating the manufacture, use or sale of pharmaceuticals or biological products, which notice reflects approval by the agency of manufacture, use or sale for human administration.

Synthesis of Drug Conjugates

The embodiments are also directed to processes and intermediates useful for preparing subject compounds or a salt or solvate or stereoisomer thereof.

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001.)

Compounds as described herein can be purified by any of the means known in the art, including chromatographic means, such as high performance liquid chromatography (HPLC), preparative thin layer chromatography, flash column chromatography and ion exchange chromatography. Any suitable stationary phase can be used, including normal and reversed phases as well as ionic resins. Most typically the disclosed compounds are purified via silica gel and/or alumina chromatography. See, e.g., Introduction to Modern Liquid Chromatography, 2nd ed., ed. L. R. Snyder and J. J. Kirkland, John Wiley and Sons, 1979; and Thin Layer Chromatography, E. Stahl (ed.), Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as T. W. Greene and P. G. M. Wuts, "Protective Groups in Organic Synthesis," 4$^{th}$ ed., Wiley, New York 2006. The protecting groups may be removed at a convenient subsequent stage using methods known from the art.

Exemplary chemical entities useful in methods of the embodiments will now be described by reference to illustrative synthetic schemes for their general preparation herein and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Furthermore, one of skill in the art will recognize that the transformations shown in the schemes below may be performed in any order that is compatible with the functionality of the particular pendant groups. Each of the reactions depicted in the general schemes is preferably run at a temperature from about 0° C. to the reflux temperature of the organic solvent used. Unless otherwise specified, the variables are as defined above in reference to Formula (I).

The conjugates of the present embodiments may be constructed by attaching the drug moiety to the antibody through a linker comprising a hydrophilic self-immolative spacer.

Representative syntheses for the linker portion of compounds of Formula (I) are described in schemes below, and the particular examples that follow.

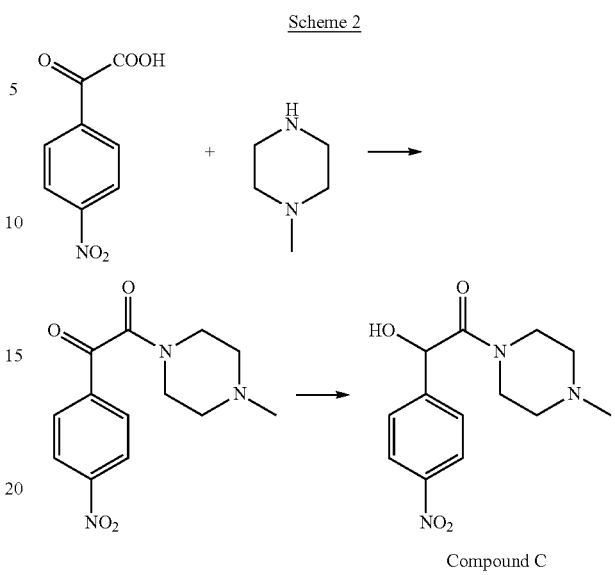

Scheme 2

Synthesis of Compound C from 4-nitrobenzaldehyde is shown in Scheme 2. 4-Nitrophenylglycolic acid is converted to the corresponding acid chloride using a chlorinating reagent, such as SOCl$_2$, PCl$_3$, or PCl$_5$. The acid chloride is then reacted with 1-methylpiperazine to give the ketoamide intermediate. Alternatively, the 4-nitrophenylglycolic acid can be coupled to the 1-methylpiperazine with use of coupling agent, such as EDCI. The ketoamide intermediate contains a keto group, which is then reduced with a reducing reagent, such as DIBAL-H, BH$_3$, LiAlH$_4$—AlCl$_3$, LiAlH$_4$—BF$_3$-Et$_2$O, or sodium borohydride, to produce Compound C.

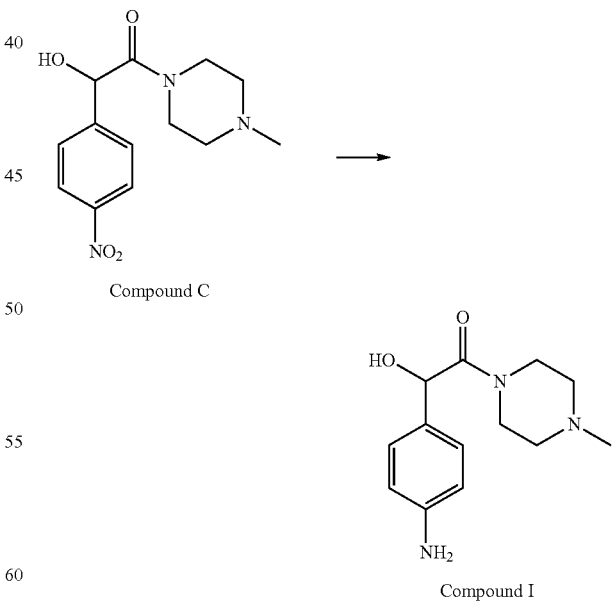

Scheme 3

Referring to Scheme 3, the nitro group of Compound C is reduced to yield an aniline group in Compound I by catalytic hydrogenation with catalysts, such as palladium, nickel, or platinum. Examples of suitable hydrogenation catalysts include Pd/C and Raney nickel.

Scheme 4

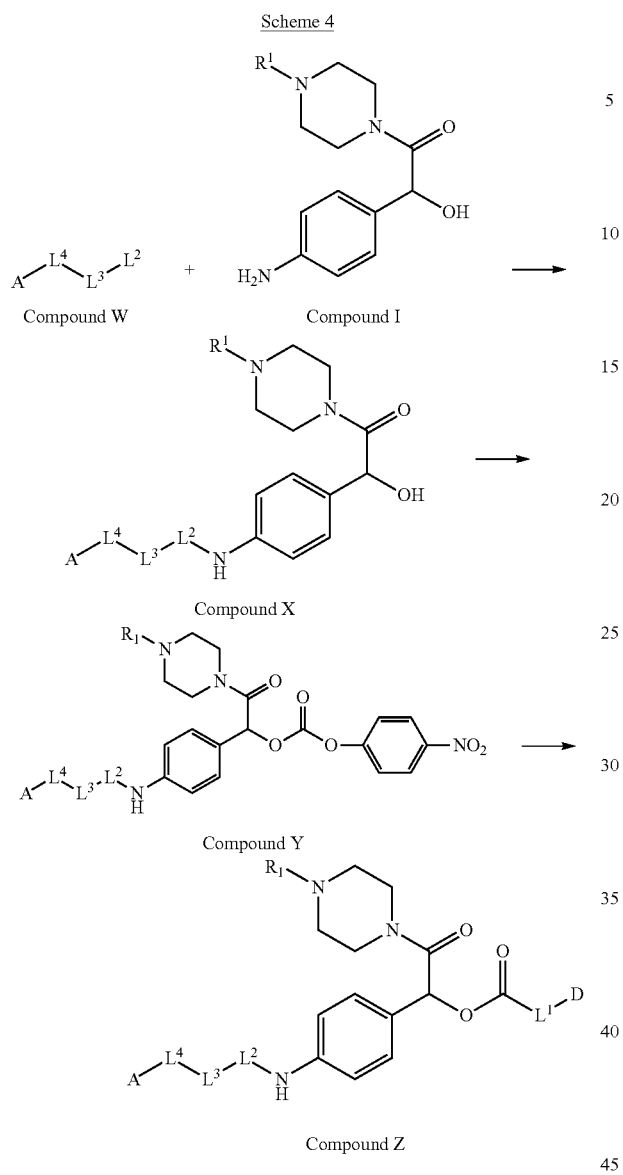

Referring to Scheme 4, Compound I provides the hydrophilic self-immolative linker portion in the compounds of the present embodiments. The amino group of Compound I can react with the Compound W through standard peptide coupling conditions to produce Compound X. Reagents such as EDCI/HOBt, HOBt, PyBOP, HATU or BEM (Carpino, L. A. J. Am. Chem. Soc. 1993, 115, 4397. Carpino, L. A.; El-Faham, A. J. Am. Chem. Soc. 1995, 117, 5401. Li, P.; Xu, J. C. J. Pept. Res. 2001, 58, 129) in the presence of a base such as DIEA or other bases familiar to one skilled in the art and in an appropriate solvent can be used.

With continued reference to Scheme 4, the hydroxyl group of Compound X is converted to an activated carbonate using 4-nitrophenyl chloroformate. With Compound Y, reaction with a drug with an amino group can produce Compound Z. If the drug does not contain an amino group, a second, intermediate self-immolative spacer or a cyclization self-elimination linker can be situated between the drug moiety and the aminobenzyloxycarbonyl group, as discussed above.

In certain embodiments, referring to Scheme 5 below, the -L³-L²-portion of the linker is attached to Compound I. Then the -A-L⁴-portion is attached.

Scheme 5

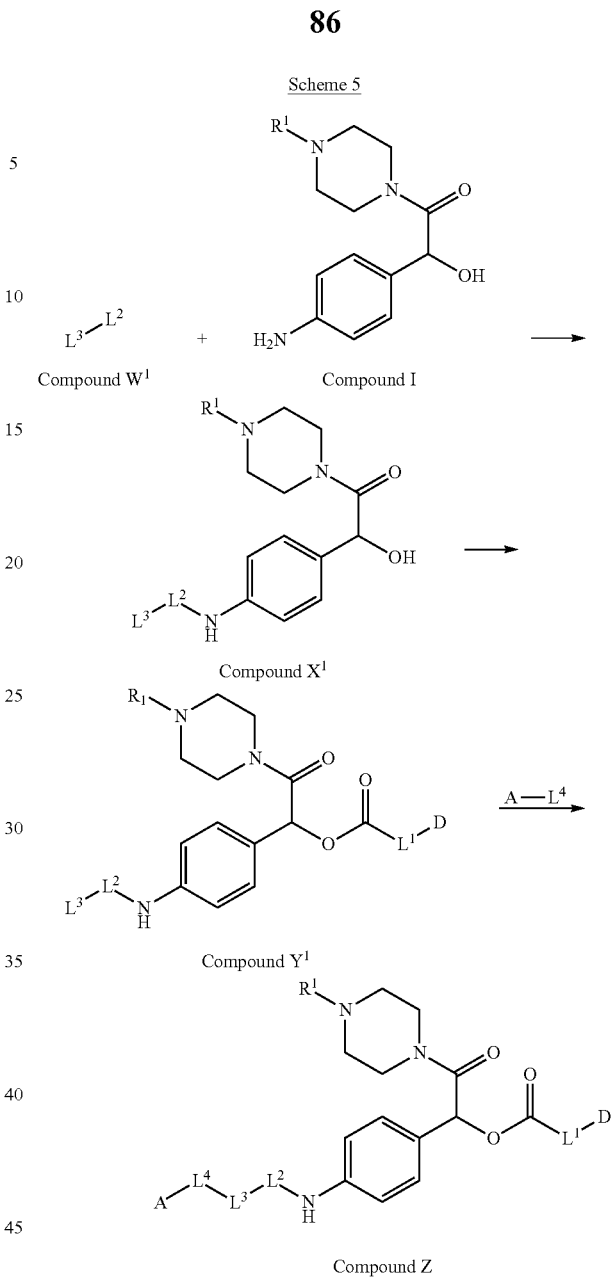

A process for preparing the compound of the present embodiments includes preparing a solution of the antibody in a buffer and treating with a solution of reducing agent, such as TCEP. The amount of free thiols is determined. When the amount of free thiols reaches a predetermined amount, the partially reduced antibody is alkylated with the linker-drug portion.

In some embodiments, provided is a process for making a compound of formula (I) or (Ia):

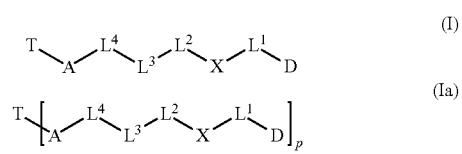

or a salt or solvate or stereoisomer thereof; wherein D, T, X, $L^1$, $L^2$, $L^3$, $L^4$, A and p, where applicable, are as defined for Formula (I) or (Ia), comprising reacting a compound comprising a targeting moiety T with a compound of formula: $A-L^4-L^3-L^2-X-L^1-D$. In some embodiments, T is an antibody that specifically binds to a folate receptor alpha (e.g. a human FRA). In some embodiments, provided is a compound produced by the process. Further provided is a composition comprising one or more compounds produced by the process.

In some embodiments, provided is a process for making a compound of formula (II) or (IIa):

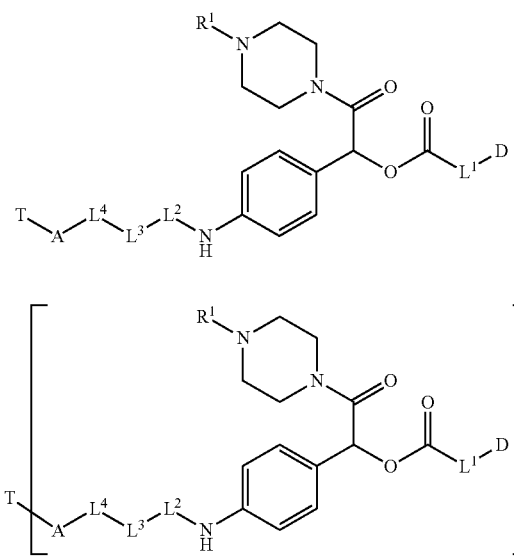

(II)

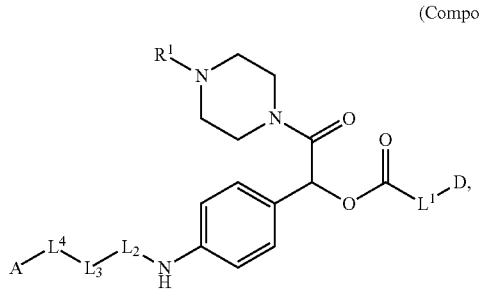

(IIa)

or a salt or solvate or stereoisomer thereof; wherein D, T, $L^1$, $L^2$, $L^3$, $L^4$, A and p, where applicable, are as defined for Formula (II) or (IIa), comprising reacting an antibody bearing one or more free thiols (or sulfhydryl groups) with Compound Z:

(Compound Z)

or a salt or solvate or stereoisomer thereof. In some embodiments, the antibody bearing one or more free thiols (or sulfhydryl groups) is an anti-FRA antibody. In some embodiments, the antibody bearing one or more free thiols (or sulfhydryl groups) is antibody hLK26 or hMOV19. In some embodiments, the antibody bearing one or more free thiols (or sulfhydryl groups) is a derivative of antibody 26B3 (e.g., such a humanized or chimeric antibody). In some embodiments, the antibody bearing one or more free thiols (or sulfhydryl groups) is hLK26 where one or more amino acid residues of the heavy chain and/or the light chain of the antibody are replaced with cysteine residues, or hMOV19 where one or more amino acid residues of the heavy chain and/or the light chain of the antibody are replaced with cysteine residues. In some embodiments, the antibody bearing one or more free thiols (or sulfhydryl groups) is a derivative of antibody 26B3 (e.g., such a humanized or chimeric antibody), or a derivative of 26B3 (e.g., such as a humanized or chimeric antibody) where one or more amino acid residues of the heavy chain and/or the light chain of the antibody are replaced with cysteine residues. In some embodiments, the process further comprises a method for preparing Compound Z as detailed herein. In some embodiments, the process further comprises a method for preparing one or more of the synthetic intermediates leading to Compound Z (e.g., Compound Y and Compound X) as detailed herein. In some embodiments, provided is a compound produced by any of the processes detailed herein. Further provided is a composition comprising one or more compounds produced by any of the processes detailed herein.

In some embodiments, a process is provided for making a compound of formula (II):

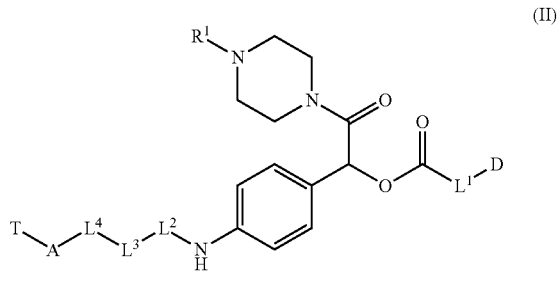

(II)

or a salt or solvate or stereoisomer thereof;
wherein:
D is a drug moiety;
T is an antibody;
$R^1$ is hydrogen, unsubstituted or substituted $C_{1-3}$ alkyl, or unsubstituted or substituted heterocyclyl;
$L^1$ is a bond, a second self-immolative linker, or a cyclization self-elimination linker;
$L^2$ is a bond or a second self-immolative linker;
wherein if $L^1$ is a second self-immolative linker or a cyclization self-elimination linker, then $L^2$ is a bond;
wherein if $L^2$ is a second self-immolative linker, then $L^1$ is a bond;
$L^3$ is a peptide linker;
$L^4$ is a bond or a spacer; and
A is an acyl unit;
comprising reacting an antibody with Compound Z:

(Compound Z)

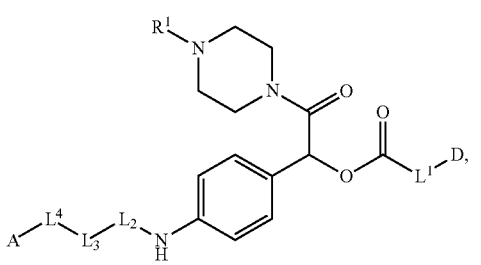

or a salt or solvate or stereoisomer thereof. In some embodiments, T is an antibody that specifically binds to a folate receptor alpha (e.g., a human FRA).

In some embodiments, a process is provided for making a compound of formula (IIa):

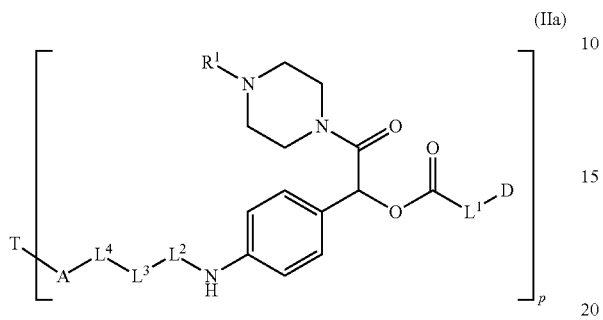

(IIa)

or a salt or solvate or stereoisomer thereof;
wherein:
p is 1 to 20;
D is a drug moiety;
T is an antibody;
$R^1$ is hydrogen, unsubstituted or substituted $C_{1-3}$ alkyl, or unsubstituted or substituted heterocyclyl;
$L^1$ is a bond, a second self-immolative linker, or a cyclization self-elimination linker;
$L^2$ is a bond or a second self-immolative linker;
  wherein if $L^1$ is a second self-immolative linker or a cyclization self-elimination linker, then $L^2$ is a bond;
  wherein if $L^2$ is a second self-immolative linker, then $L^1$ is a bond;
$L^3$ is a peptide linker;
$L^4$ is a bond or a spacer; and
A is an acyl unit;
comprising reacting an antibody with Compound Z:

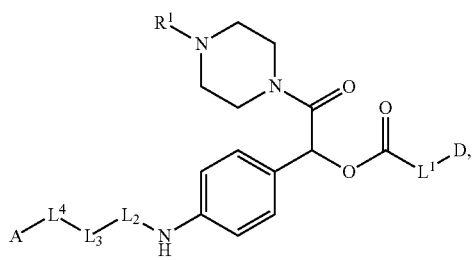

(Compound Z)

or a salt or solvate or stereoisomer thereof. In some embodiments, T is an antibody that specifically binds to a folate receptor alpha (e.g., a human FRA).

Further provided is a compound produced by any of the processes of making compounds and/or methods of preparing compounds as detailed herein. Also provided is a composition (e.g., a pharmaceutical composition) comprising one or more of the compounds produced by any of the processes of making compounds and/or methods of preparing compounds as detailed herein.

The present disclosure provides for the process for the preparation of the compounds and intermediates in Schemes 4 and 5. The compounds represented in Schemes 4 and 5 are meant to have full valences or properly capped with optional protecting groups or leaving groups when appropriate. For example, as shown in the scheme "Synthesis of Compound TAP-18H," $L^3$-$L^2$ can be

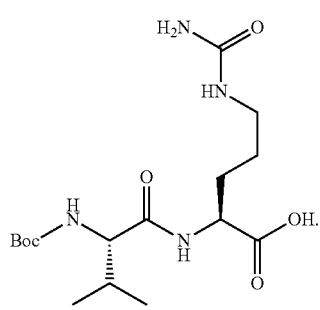 [SMILES: CC(C)[C@H](NC(=O)OC(C)(C)C)C(=O)N[C@@H](CCCNC(N)=O)C(=O)O]

The present disclosure provides for a method of preparing Compound X:

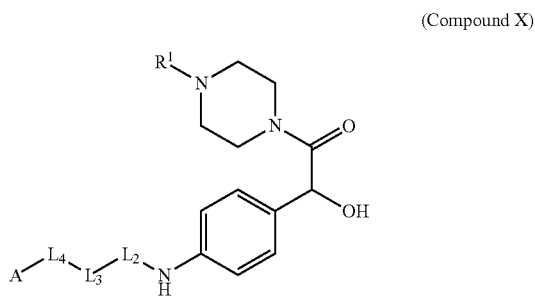

(Compound X)

or a salt or solvate or stereoisomer thereof;
wherein:
$R^1$ is hydrogen, unsubstituted or substituted $C_{1-3}$ alkyl, or unsubstituted or substituted heterocyclyl;
$L^2$ is a bond or a second self-immolative linker;
$L^3$ is a peptide linker;
$L^4$ is a bond or a spacer; and
A is an acyl unit;
comprising: reacting Compound W: A-$L^4$-$L^3$-$L^2$, and Compound I:

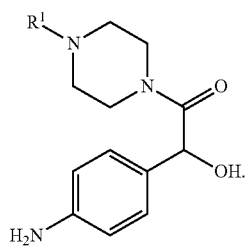

The present disclosure provides for a method of preparing Compound Z:

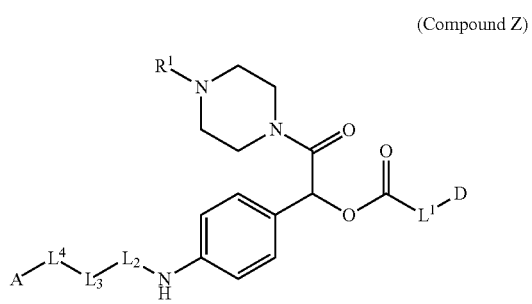

(Compound Z)

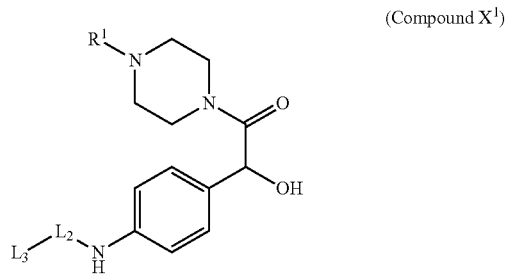

(Compound X¹)

or a salt or solvate or stereoisomer thereof;
wherein:
D is a drug moiety;
$R^1$ is hydrogen, unsubstituted or substituted $C_{1-3}$ alkyl, or unsubstituted or substituted heterocyclyl;
$L^1$ is a bond, a second self-immolative linker, or a cyclization self-elimination linker;
$L^2$ is a bond or a second self-immolative linker;
wherein if $L^1$ is a second self-immolative linker or a cyclization self-elimination linker, then $L^2$ is a bond;
wherein if $L^2$ is a second self-immolative linker, then $L^1$ is a bond;
$L^3$ is a peptide linker;
$L^4$ is a bond or a spacer; and
A is an acyl unit;
comprising: reacting Compound X:

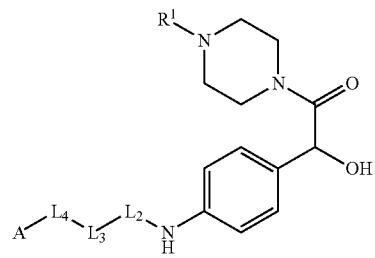

and p-nitrophenyl chloroformate to form Compound Y:

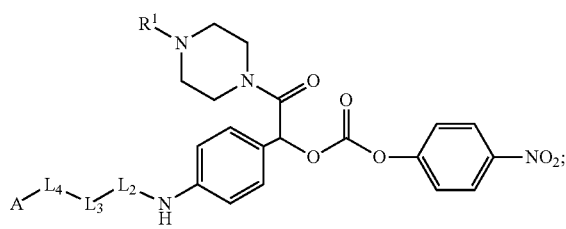

and reacting Compound Y with a compound comprising $L^1$-D.

The present disclosure provides for a method of preparing Compound $X^1$:

or a salt or solvate or stereoisomer thereof;
wherein:
$R^1$ is hydrogen, unsubstituted or substituted $C_{1-3}$ alkyl, or unsubstituted or substituted heterocyclyl;
$L^2$ is a bond or a second self-immolative linker; and
$L^3$ is a peptide linker;
comprising: reacting Compound $W^1$: $L^3$-$L^2$, and Compound I:

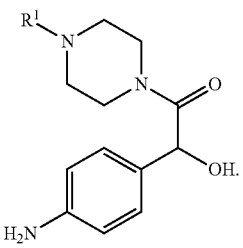

The present disclosure provides for a method of preparing Compound $Y^1$:

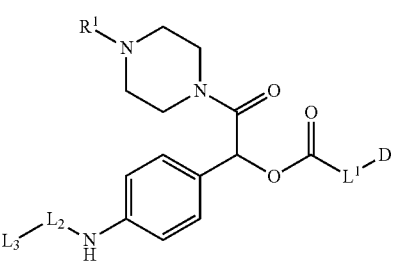

(Compound Y¹)

or a salt or solvate or stereoisomer thereof;
wherein:
$R^1$ is hydrogen, unsubstituted or substituted $C_{1-3}$ alkyl, or unsubstituted or substituted heterocyclyl;
D is a drug moiety;
$L^1$ is a bond, a second self-immolative linker, or a cyclization self-elimination linker;
$L^2$ is a bond or a second self-immolative linker;
wherein if $L^1$ is a second self-immolative linker or a cyclization self-elimination linker, then $L^2$ is a bond;

wherein if L² is a second self-immolative linker, then L¹ is a bond; and
L³ is a peptide linker;
comprising: reacting Compound X¹:

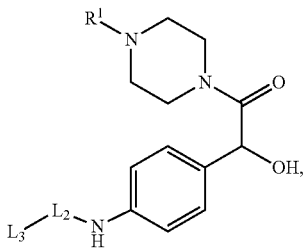

and a compound comprising L¹-D.

The present disclosure provides for a method of preparing Compound Z:

(Compound Z)

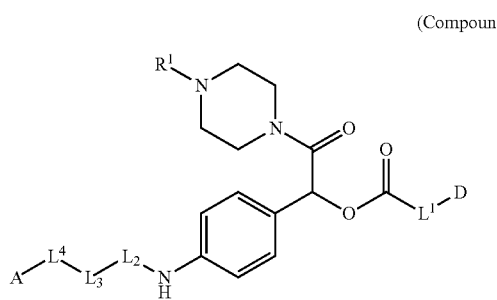

or a salt or solvate or stereoisomer thereof;
wherein:
D is a drug moiety;
R¹ is hydrogen, unsubstituted or substituted $C_{1-3}$ alkyl, or unsubstituted or substituted heterocyclyl;
L¹ is a bond, a second self-immolative linker, or a cyclization self-elimination linker;
L² is a bond or a second self-immolative linker;
  wherein if L¹ is a second self-immolative linker or a cyclization self-elimination linker, then L² is a bond;
  wherein if L² is a second self-immolative linker, then L¹ is a bond;
L³ is a peptide linker;
L⁴ is a bond or a spacer; and
A is an acyl unit;
comprising: reacting Compound Y¹:

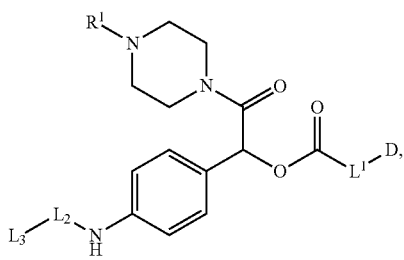

and a compound comprising A-L⁴.

The present disclosure provides for a compound of formula:

(Compound X)

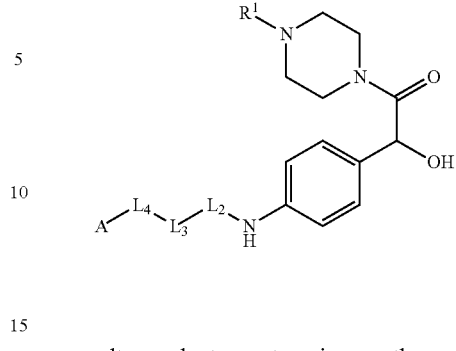

or a salt or solvate or stereoisomer thereof;
wherein:
R¹ is hydrogen, unsubstituted or substituted $C_{1-3}$ alkyl, or unsubstituted or substituted heterocyclyl;
L² is a bond or a second self-immolative linker;
L³ is a peptide linker;
L⁴ is a bond or a spacer; and
A is an acyl unit.

The present disclosure provides for a compound of formula:

(Compound Z)

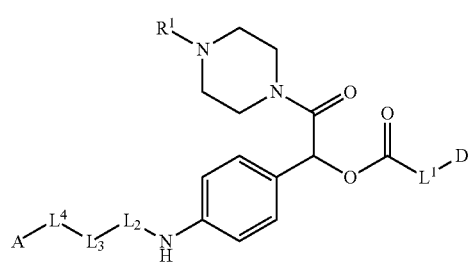

or a salt or solvate or stereoisomer thereof;
wherein:
R¹ is hydrogen, unsubstituted or substituted $C_{1-3}$ alkyl, or unsubstituted or substituted heterocyclyl;
D is a drug moiety;
L¹ is a bond, a second self-immolative linker, or a cyclization self-elimination linker;
L² is a bond or a second self-immolative linker;
  wherein if L¹ is a second self-immolative linker or a cyclization self-elimination linker, then L² is a bond;
  wherein if L² is a second self-immolative linker, then L¹ is a bond;
L³ is a peptide linker;
L⁴ is a bond or a spacer; and
A is an acyl unit.

The present disclosure provides for a compound of formula:

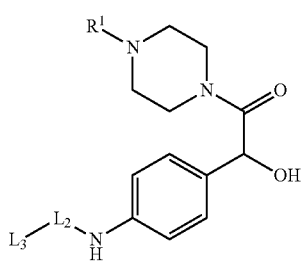

(Compound X¹)

or a salt or solvate or stereoisomer thereof;
wherein:
R¹ is hydrogen, unsubstituted or substituted $C_{1-3}$ alkyl, or unsubstituted or substituted heterocyclyl;
$L^2$ is a bond or a second self-immolative linker; and
$L^3$ is a peptide linker.

The present disclosure provides for a compound of formula:

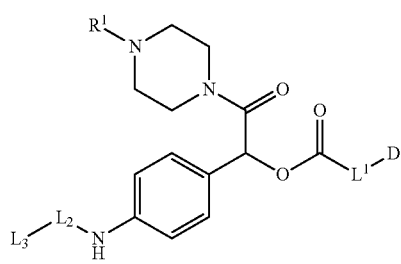

(Compound Y¹)

or a salt or solvate or stereoisomer thereof;
wherein:
R¹ is hydrogen, unsubstituted or substituted $C_{1-3}$ alkyl, or unsubstituted or substituted heterocyclyl;
D is a drug moiety;
$L^1$ is a bond, a second self-immolative linker, or a cyclization self-elimination linker;
$L^2$ is a bond or a second self-immolative linker;
 wherein if $L^1$ is a second self-immolative linker or a cyclization self-elimination linker, then $L^2$ is a bond;
 wherein if $L^2$ is a second self-immolative linker, then $L^1$ is a bond; and
$L^3$ is a peptide linker.

The specification is considered to be sufficient to enable one skilled in the art to practice the invention. Various modifications of the invention in addition to those shown and described herein will become apparent to those skilled in the art from the foregoing description and fall within the scope of the appended claims. All publications, patents, and patent applications cited herein are hereby incorporated by reference in their entirety for all purposes.

EXAMPLES

The invention can be further understood by reference to the following examples, which are provided by way of illustration and are not meant to be limiting.

Example 1: Materials and Methods for Examples 2-6

Synthesis of Linker-Drug
Synthesis of Compound Tap-18H is shown below in the scheme. Synthesis of intermediate Compounds M and O are also shown in the schemes below.
Synthesis of Compound M

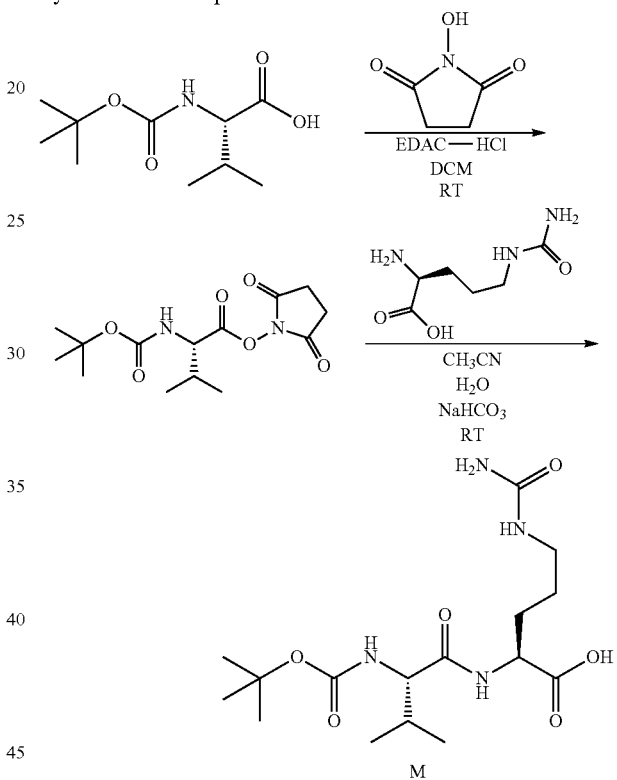

Synthesis of Compound O

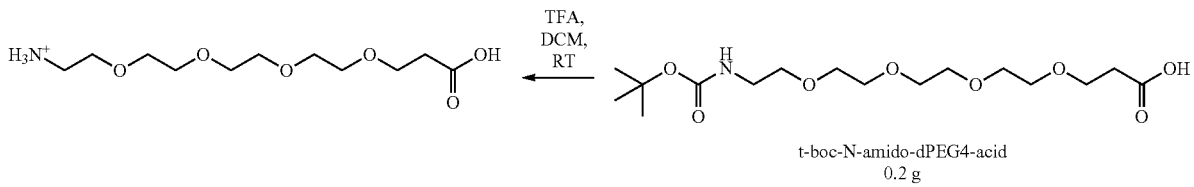

t-boc-N-amido-dPEG4-acid
0.2 g

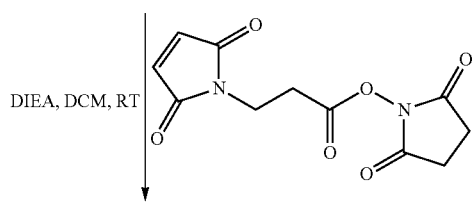

DIEA, DCM, RT

-continued
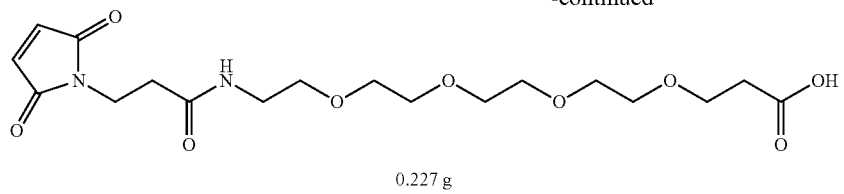
0.227 g
↓ EDCl, N-hydroxysuccinimide
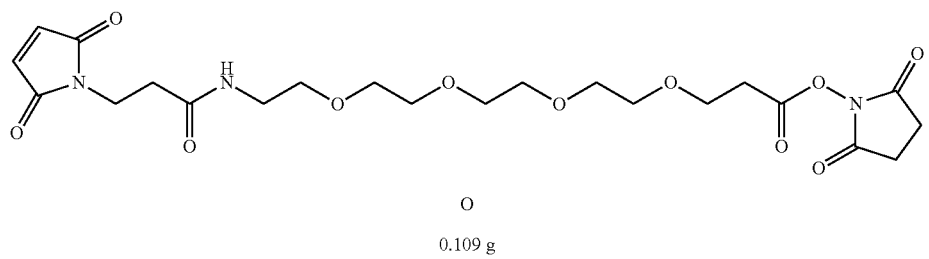
0.109 g
Synthesis of Compound TAP-18H
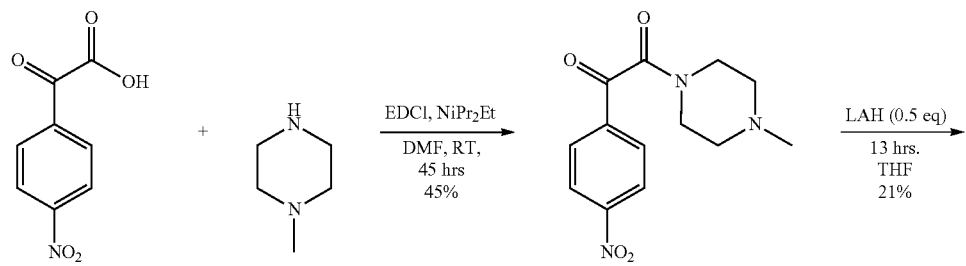
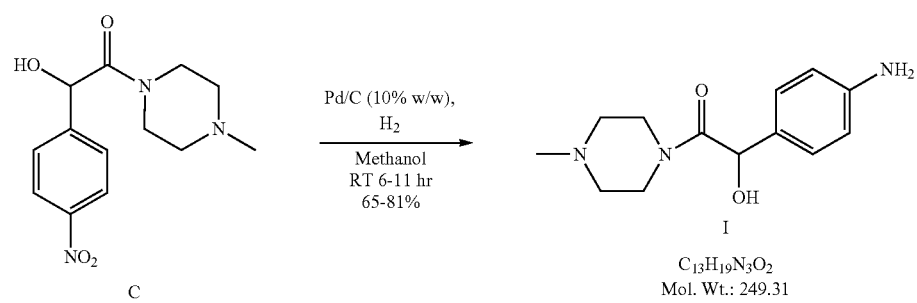
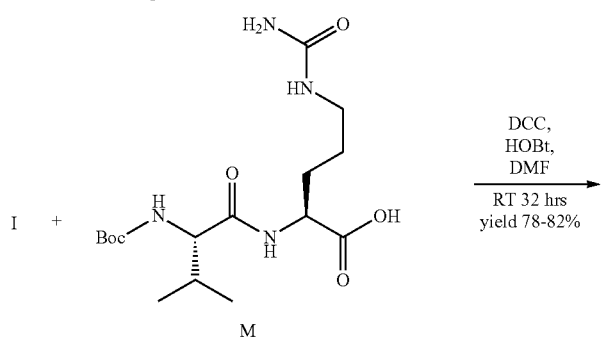

-continued
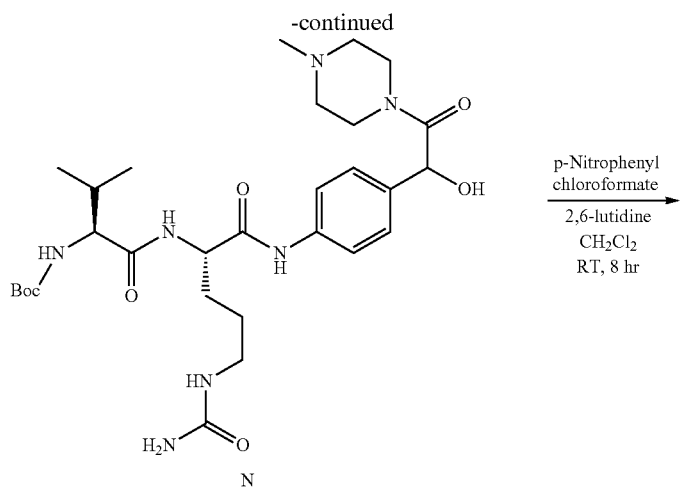
p-Nitrophenyl chloroformate
2,6-lutidine
CH$_2$Cl$_2$
RT, 8 hr
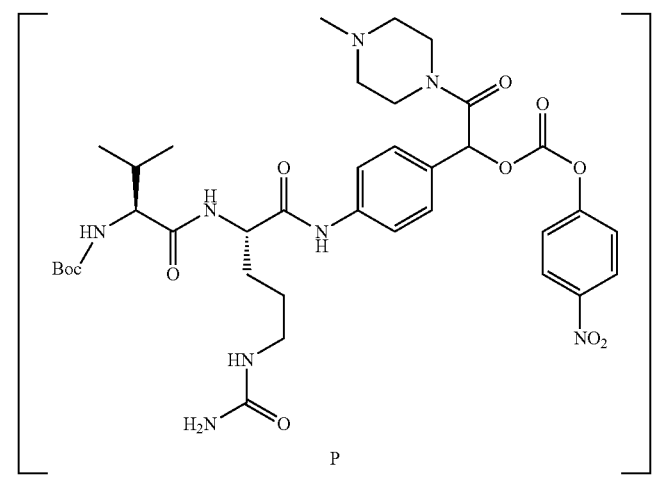
P
Used in situ, evaporated solvent and used in next step without any purification
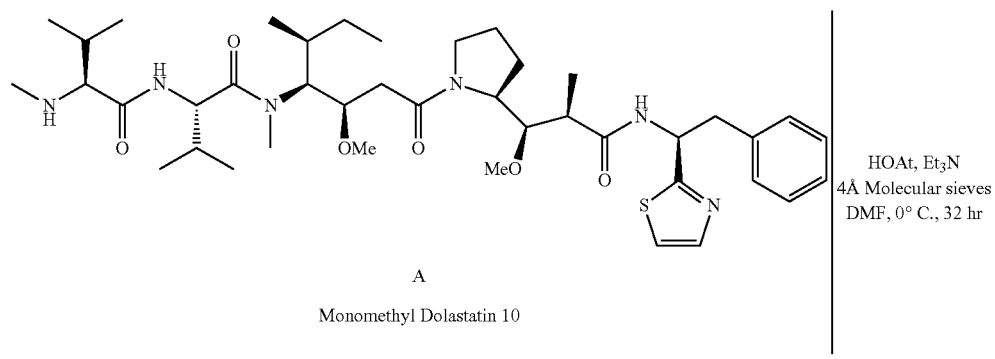
A
Monomethyl Dolastatin 10
HOAt, Et$_3$N
4Å Molecular sieves
DMF, 0° C., 32 hr

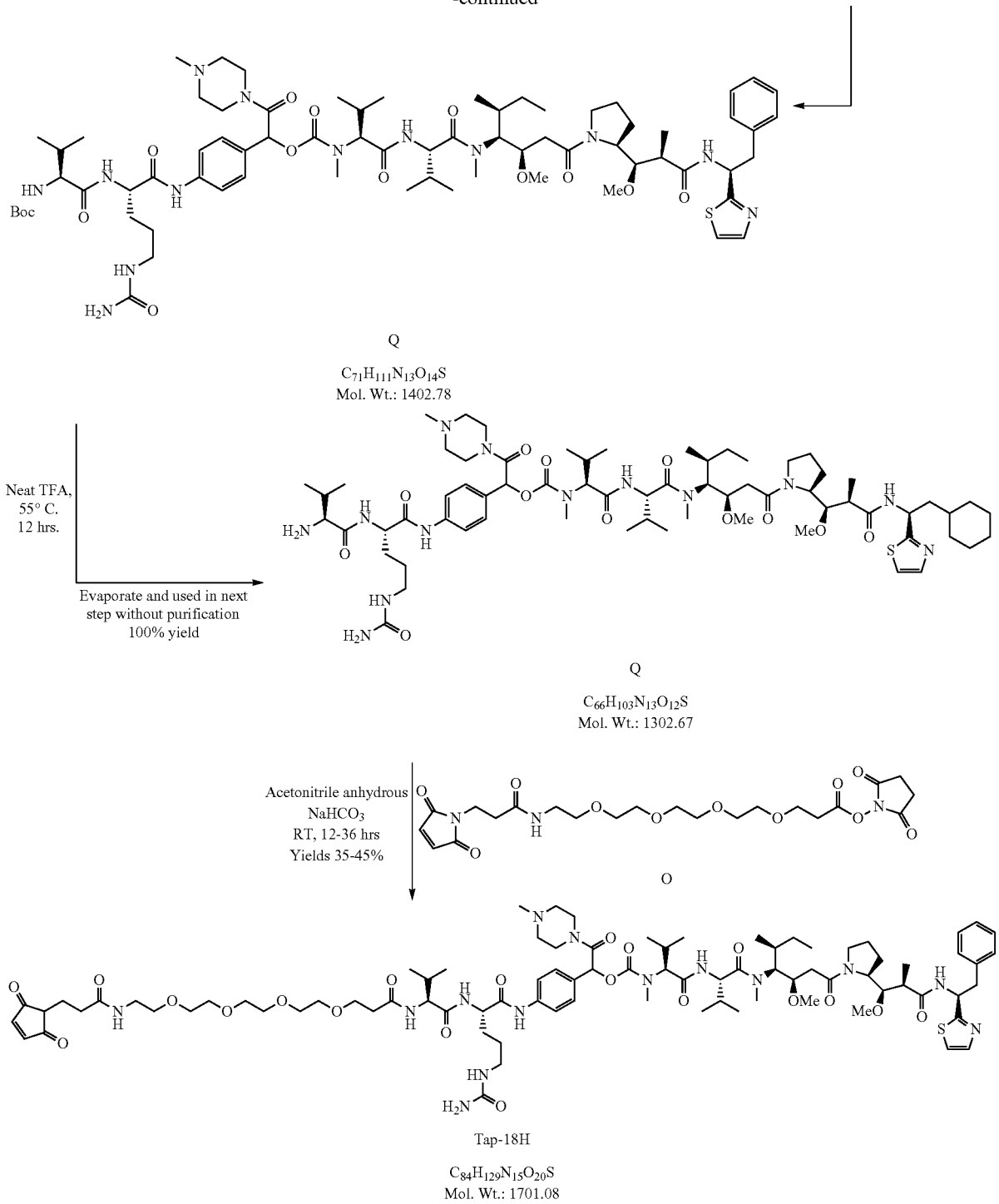

Referring to the scheme of synthesis of Compound Tap-18H, commercially available 4-nitrophenylglyoxylic acid was condensed with N-methylpiperazine using either $PCl_5$, or EDCI and $NiPr_2Et$ in DMF, or 2-chloro-4,6-dimethoxy-1,3,5-triazine in $CH_2Cl_2$ and N-methylmorpholine as coupling agent to produce the desired ketoamide. In a typical procedure, a solution of 2-chloro-4,6-dimethoxy-1,3,5-triazine (5 mmol) in $CH_2Cl_2$ (20 ml), N-methylmorpholine (15 mmol) was added at 0-5° C. under continuous stirring. A white suspension was formed after 30-40 minutes and to this mixture 4-nitrophenylglyoxylic acid in $CH_2Cl_2$ (10 ml) was added, resulting in the formation of a clear solution. After stirring the mixture for 1 hour, N-methylpiperazine (5 mmol) was added at room temperature. After completion of the reaction (TLC, 10 minutes), the mixture was washed with 10% aqueous $NaHCO_3$ solution (2×10 ml) followed by $H_2O$ (3×10 ml). The organic layer was dried over anhydrous sodium sulfate and removal of the solvent under reduced pressure furnished a crude product which was further purified by recrystallization or column chromatography (pet. ether:ethyl acetate=8:2).

The ketoamide compound was further reduced by 0.5 equivalent amounts of LiAlH$_4$ in the presence of THF or DIBAL-H or sodium borohydride to produce the nitro Compound C. [B. P. Bandgar and S. S. Pandit, Tetrahedron Letters 44 (2003) 3855-3858]

Nitro Compound C was reduced to aniline Compound I by either treatment with SnCl$_2$ or catalytic hydrogenation with Pd/C (10% w/w) as catalyst in methanol at room temperature for about 6-11 hours with yield from 65-81%. It could be obtained through the following procedures using MultiMaxIR system with an RB04-50 Reactor B. The reactor was filled initially with 35 ml of methanol, 0.03 mg of 10% Pd/C and 0.0252 mol of nitro Compound C and the hydrogen was add in the reactor up to pressure at 6.3 bar (H$_2$, const.).

Referring to the scheme of synthesis of Compound M, Boc-protected L-valine was treated with N-hydroxysuccinimide and EDAC-HCl in DCM or N-hydroxysuccinimide and EDC in DCM to give the succinimide ester. This activated ester was reacted with L-Citrulline and CH$_3$CN, H$_2$O, NaHCO$_3$ to furnish Boc-protected Compound M.

Referring to the scheme of synthesis of Compound Tap-18H, aniline Compound I was coupled with Boc-protected Compound M by means of either DCC/HOBt in DMF at room temperature for 32 hours to give Compound N (yield 78-82%), or with PS-carbodiimide, in which reaction the synthesis of Compound N was carried out starting from 100 mg of Compound M with 1.5 equivalents of aniline Compound I in the presence of two equivalents of PS-carbodiimide and 1.7 equivalents of HOBt in DCM for 24 hours. Analysis by LC/MS showed the peak with the desired mass and approximately 50-60% conversion.

The coupled product Compound N was then reacted with 4-nitrophenyl chloroformate in the presence of 2,6-lutidine in DCM at RT for 8 hours to yield carbonate Compound P, LC/MS showed the peak with the desired mass.

Treatment of carbonate Compound P with monomethyl Dolastatin 10 in the presence of HOAt and Et$_3$N in DMF resulted in the formation of Compound Q.

Referring to the scheme of synthesis of Compound O,β-alanine was treated with maleic anhydride in DMF and the acid so obtained was reacted with N-hydroxysuccinimide (NHS) under DCC coupling to give NHS-ester. The BOC protective group in commercially available t-boc-N-amido-dPEG4-acid was removed by treatment with TFA to give the TFA salt of the amine, which was reacted with previously synthesized NHS ester. The carboxylic acid so obtained was isolated and was coupled with N-hydroxysuccinimide using EDCI to furnish NHS ester Compound O.

Referring to the scheme of synthesis of Compound Tap-18H, the Boc-group in Compound Q was removed with TFA and the free amine was coupled with NHS ester Compound O in anhydrous acetonitrile and NaHCO$_3$ at room temperature for 12-36 hours to produce the final product Tap-18H with yield of 35-45%.

FIG. 1 shows an NMR spectrum of Tap-18H.

Synthesis of Compound TAP-18Hr1

Figure 2:
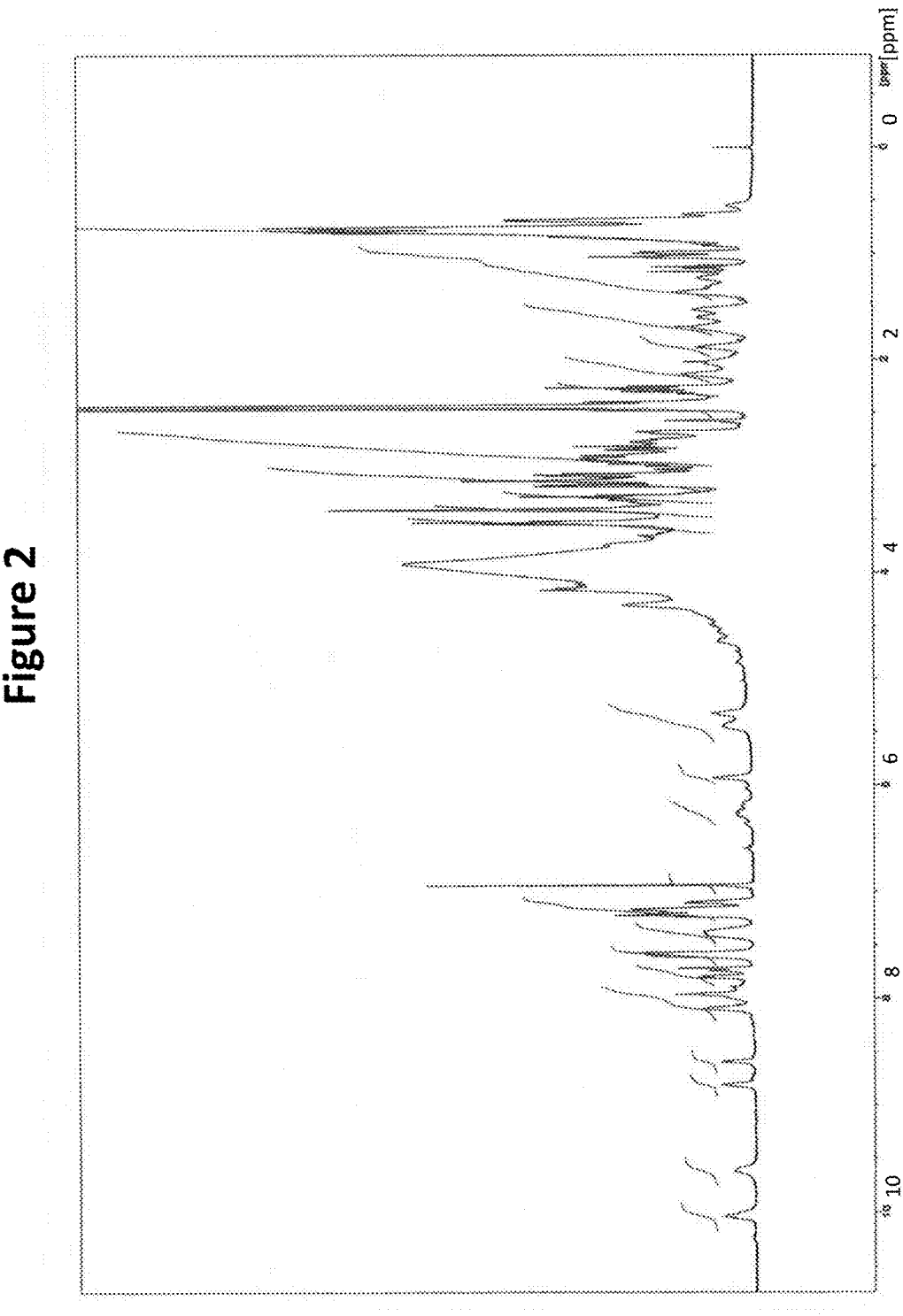
FIG. 2 shows an NMR spectrum of Tap-18Hr1.

Tap-18Hr1 was synthesized with the formula shown below. FIG. 2 shows NMR spectrum of Tap-18Hr1.

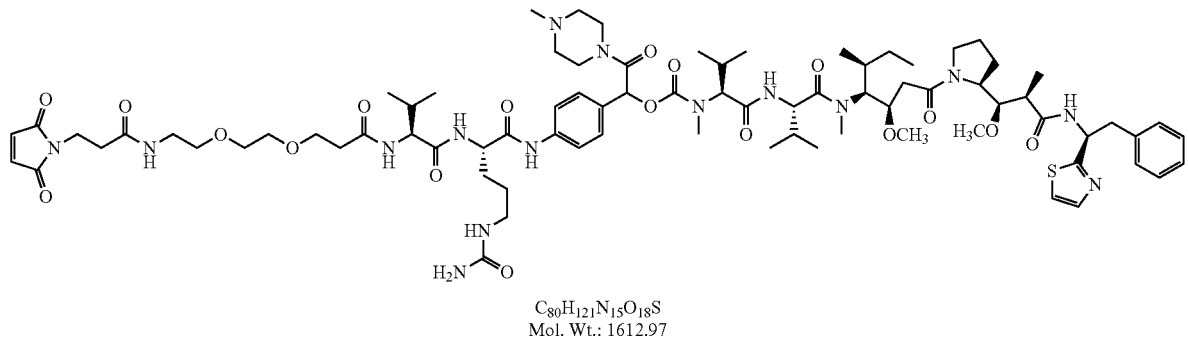

(Tap-18Hr1)

C$_{80}$H$_{121}$N$_{15}$O$_{18}$S
Mol. Wt.: 1612.97

Synthesis of Compound TAP-18Hr2

Figure 3:
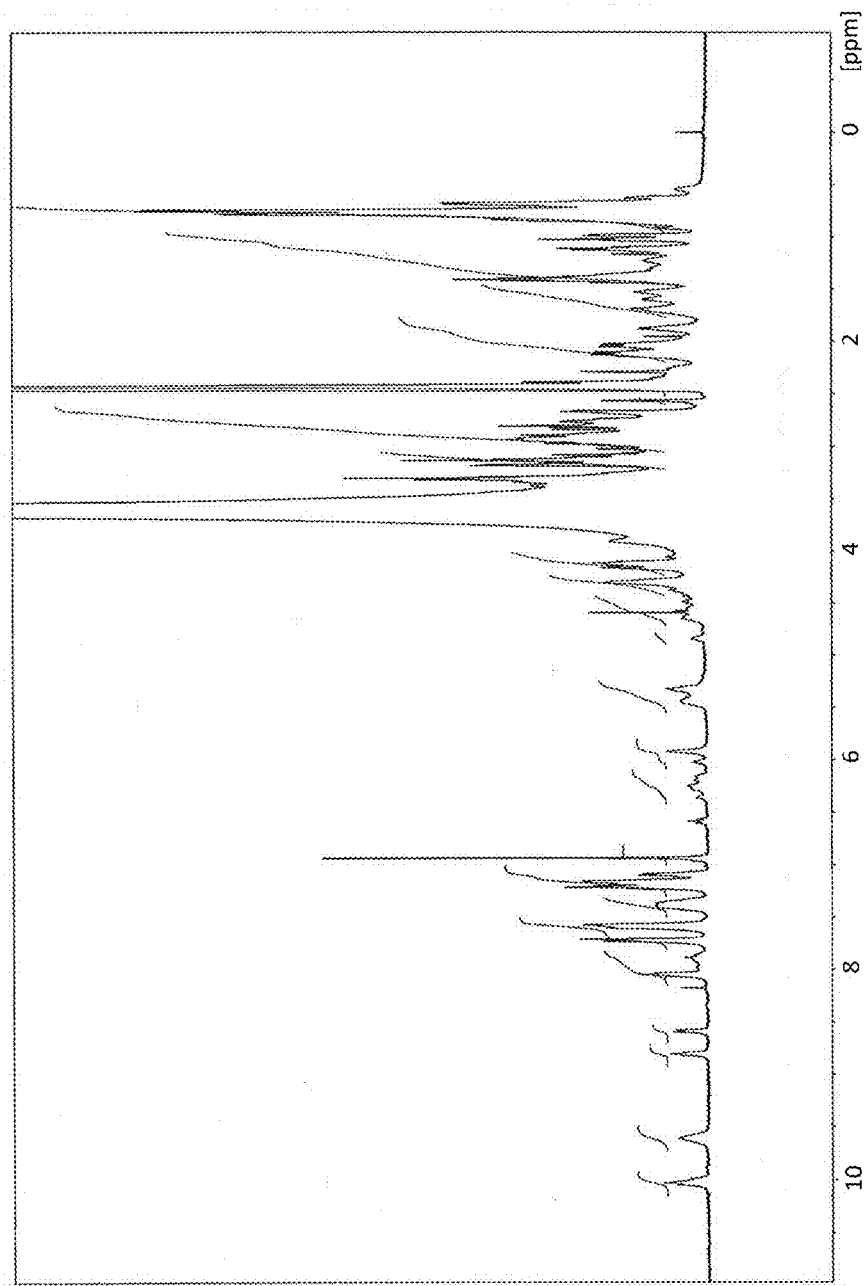
FIG. 3 shows an NMR spectrum of Tap-18Hr2.

Tap-18Hr2 was synthesized with the formula shown below. FIG. 3 shows NMR spectrum of Tap-18Hr2.

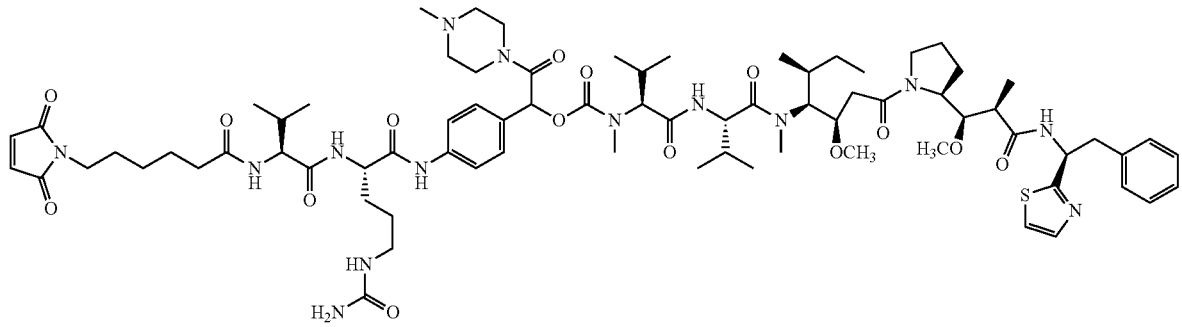

(Tap-18Hr2)

Cell Lines

The ovarian cancer cells SK-OV-3 (ATCC®, Cat. No. HTB-77™) were cultured in McCoy's 5A Medium (GIBCO®, Cat. No. 16600) supplemented with 10% FBS (HYCLONE®, Cat. No. SH30071.03) and 100 U/mL penicillin/100 µg/mL streptomycin (GIBCO®, Cat. No. 15140). The ovarian cancer cells OVCAR-3 (Bioresource Collection and Research Center®, Cat. No. 60551) were cultured in RPMI Medium 1640 (GIBCO®, Cat. No. 22400) supplemented with 20% FBS, 1 mM sodium pyruvate (GIBCO®, Cat. No. 11360), 0.01 mg/mL bovine insulin (SIGMA®, Cat. No. I6634) and 100 U/mL penicillin/100 µg/mL streptomycin. The ovarian cancer cells OVCAR-3B were adapted from OVCAR-3 and cultured in RPMI Medium 1640 (GIBCO®, Cat. No. 22400) supplemented with 10% FBS, 1 mM sodium pyruvate (GIBCO®, Cat. No. 11360), and 100 U/mL penicillin/100 µg/mL streptomycin. The pancreatic cancer cells Panc 02.03B were adapted from Panc 02.03 (ATCC®, Cat. No. CRL-2553™), and cultured without insulin in RPMI Medium 1640 supplemented with 15% FBS, 1 mM sodium pyruvate, and 100 U/mL penicillin/100 µg/mL streptomycin. The lung cancer cells NCI-H2110 (ATCC®, Cat. No. CRL-5924™) were cultured in RPMI Medium 1640 supplemented with 10% FBS, 1 mM sodium pyruvate, 2.5 g/liter D-glucose (SIGMA®, Cat. No. G8270) and 100 U/mL penicillin/100 µg/mL streptomycin. The lung cancer cells NCI-H292 (BIORESOURCE COLLECTION AND RESEARCH CENTER®, Cat. No. 60372) were cultured in RPMI Medium 1640 supplemented with 10% FBS, 1 mM sodium pyruvate and 100 U/mL penicillin/100 µg/mL streptomycin.

Reagents

DTT and DTPA were obtained from SIGMA-ALDRICH® (St. Louis, Mo.). TCEP was obtained from Acros (Morris Plains, N.J.). DTNB was obtained from Thermo Scientific (Rockford, Ill.). Sodium phosphate, sodium borate, and sodium chloride were obtained from J.T. BAKER™ (Center Valley, Pa.). Cysteine was obtained from ALFA AESAR® (Ward Hill, Mass.).

TABLE 5

Amino Acid Sequences of anti-FRA antibody hLK26

| SEQ ID NO. | DESCRIPTION |
| --- | --- |
| 1 | hLK26-IgG1 heavy chain |
| 2 | hLK26-IgG4p heavy chain |
| 3 | hLK26-kappa light chain |

(hLK26-IgG1 heavy chain)
SEQ ID NO: 1
EVQLVESGGGVVQPGRSLRLSCSASGFTFSGYGLSWVRQAPGKGLEWVA

MISSGGSYTYYADSVKGRFAISRDNAKNTLFLQMDSLRPEDTGVYFCAR

HGDDPAWFAYWGQGTPVTVSSASTKGPSVFPLAPSSKSTSGGTAALGCL

VKDYFPEPVTVSWNSGALTSGVHTFPAVLQSSGLYSLSSVVTVPSSSLG

TQTYICNVNHKPSNTKVDKKVEPKSCDKTHTCPPCPAPELLGGPSVFLF

PPKPKDTLMISRTPEVTCVVVDVSHEDPEVKFNWYVDGVEVHNAKTKPR

EEQYNSTYRVVSVLTVLHQDWLNGKEYKCKVSNKALPAPIEKTISKAKG

QPREPQVYTLPPSRDELTKNQVSLTCLVKGFYPSDIAVEWESNGQPENN

YKTTPPVLDSDGSFFLYSKLTVDKSRWQQGNVFSCSVMHEALHNHYTQK

SLSLSPGK (hLK26-IgG4p heavy chain)
SEQ ID NO: 2
EVQLVESGGGVVQPGRSLRLSCSASGFTFSGYGLSWVRQAPGKGLEWVA

MISSGGSYTYYADSVKGRFAISRDNAKNTLFLQMDSLRPEDTGVYFCAR

HGDDPAWFAYWGQGTPVTVSSASTKGPSVFPLAPCSRSTSESTAALGCL

VKDYFPEPVTVSWNSGALTSGVHTFPAVLQSSGLYSLSSVVTVPSSSLG

TKTYTCNVDHKPSNTKVDKRVESKYGPPCPPCPAPEFLGGPSVFLFPPK

PKDTLMISRTPEVTCVVVDVSQEDPEVQFNWYVDGVEVHNAKTKPREEQ

PFNSTYRVVSVLTVLHQDWLNGKEYKCKVSNKGLPSSIEKTISKAKGQR

EPQVYTLPPSQEEMTKNQVSLTCLVKGFYPSDIAVEWESNGQPENNYKT

TPPVLDSDGSFFLYSRLTVDKSRWQEGNVFSCSVMHEALHNHYTQKSLS

LSLGK (hLK26-kappa light chain)
SEQ ID NO: 3
DIQLTQSPSSLSASVGDRVTITCSVSSSISSNNLHWYQQKPGKAPKPWI

YGTSNLASGVPSRFSGSGSGTDYTFTISSLQPEDIATYYCQQWSSYPYM

YTFGQGTKVEIKRTVAAPSVFIFPPSDEQLKSGTASYYCLLNNEYPREA

KVQWKYDNALQSGNSQESVTEQDSKDSTYSLSSTLTLSKADYEKHKVYA

CEVTHQGLSSPVTKSFNRGEC

Generation of hLK26-Cysteine Variants

Cysteine residue was introduced into the constant region of heavy chain (CH) or Kappa light chain (CL) of hLK26 antibody with site-directed mutagenesis method. Briefly, mutagenesis was performed by overlapping PCR. Specific alternation in the desired base can be introduced by incorporating nucleotide changed primers. As the primers were extended, the mutation was created in the resulting amplicon. The mutation position (EU numbering) and flanking sequences of amino acids are listed in Table 6 below.

TABLE 6

Mutation Position (EU Numbering) and Flanking Sequences of Amino Acids

| Chain used for mutation | EU numbering | Flanking Sequence | SEQ ID NO: |
| --- | --- | --- | --- |
| Heavy chain | T155C | GCLVKDYFPEPVCVSWNSGALTSGV | 36 |
| | T199C | VVTVPSSSLGTKTYCCNVDHKPSNT | 47 |
| | S442C | EALHNHYTQKSLCLSPGK | 48 |
| Kappa Light chain | L201C | EVTHQGCSSPVTKSFNRGEC | 51 |
| | T206C | EVTHQGLSSPVCKSFNRGEC | 52 |

Production of Stable Cell Lines Expressing hLK26-Cys Variants hLK26-Cysteine (hLK26-Cys) variants were stably expressed and produced in Flp-In CHO cells (INVITROGEN™, Cat. No: R758-07). The DNA sequences of cysteine substituted antibody variants were inserted to pcDNA5/FRT vector (INVITROGEN™, Cat. No: V6010-20) and co-transfected with pOG44 (INVITROGEN™, Cat. No V6005-

20) following the standard procedure provided by vendor. The culture supernatants of the established cell lines were collected and purified with protein A sepharose beads (GE HEALTHCARE™, Cat. No: 17-5280-04). The purified proteins were analyzed with both SDS-PAGE and size exclusion chromatography to ensure the quality of antibodies.

Conventional Conjugation of hLK26-IgG1 Antibody

Conventional drug conjugates are achieved by conjugating the linker payload to the antibody through reduction of four inter-chain disulfide bonds, and the conjugation is thus limited to the eight exposed sulfhydryl groups of free cysteines. Linker-drugs per antibody can range from 0-8. hLK26-IgG1 antibody was partly reduced with 1.85 equivalents of TCEP in 0.025 M sodium borate pH 8, 0.025 M NaCl, 1 mM DTPA for 2 hours at 37° C. The protein concentration was quantified using an absorbance value of 1.616 at 280 nm for a 1.0 mg/mL solution, and the molar concentration determined using a molecular weight of 145, 055 g/mol. The concentration of mAb-cysteine thiols produced was determined by titrating with DTNB. Typically 3.22 thiols/mAb was obtained. Partially reduced antibody was alkylated with 1.2 molar of maleimidocaproyl-drugs (Tap18Hr1, Tap-18Hr1)/mAb-cysteine thiol or maleimido-drugs/mAb-cysteine thiol. The alkylation reaction was performed at 4° C. for 12~16 hours. Cysteine (1 mM final) was used to quench any unreacted, excess maleimidocaproyl-drugs or maleimido-drugs. The conjugation mixture was first diluted 5 fold with binding buffer, 10 mM sodium phosphate, 10 mM NaCl, 5% DMSO, pH 7.0, and applied to a hydroxyapatite column (Macroprep ceramic type I 40 µm, BIORAD®, Hercules, Calif.) for hLK26-IgG1-Tap18Hr1 purification at loading capacity of 1 mL hydroxyapatite per 20 mg of conjugated antibody. The column was previously equilibrated with 5 column volumes of binding buffer. Following sample application, the column was washed with 3 column volumes of binding buffer and then equilibrated with 5 column volumes of 10 mM sodium phosphate, 10 mM NaCl, pH 7.0. The binding ADC was then eluted with 200 mM sodium phosphate, 10 mM NaCl, pH 7.0. Following elution, the buffer was changed to Dulbecco's phosphate buffered saline using HIPREP™ 26/10 Desalting column (optional).

Site-Specific Conjugation of hLK26-Cys Variants

Site-specific drug conjugates are achieved by conjugating the linker payload (i.e. the molecule comprising the linker connected to the drug moiety) to the constant domains of antibody (CH or CL) through reduction of two engineered cysteine residues, and the conjugation is thus limited to the two exposed sulfhydryl groups of free cysteines. To specifically conjugate linker payload on the introduced cysteine, a reducing/oxidation procedure was used. To remove cysteine or glutathione on the introduced cysteine site which could have occurred during culture condition, hLK26-Cys variants-Tap18Hr1 and the heavy chain mutants of hLK26-T155C and hLK26-S442C were first treated with 10~15 fold molar excess of TCEP (ACROS ORGANICS®, Cat. No: 363830100) at 37° C. for 2~5 hours in PBS (GIBCO®, Cat. No: 21600-069) containing 1 mM DTPA (SIGMA-ALDRICH®, Cat. No: D6518). After removing the excess TCEP, the antibody was then re-oxidized with dehydroascorbic acid (DHA) (SIGMA-ALDRICH®, Cat. No: 261556) with 20~30 fold molar excess over protein at room temperature for 3~5 hours to ensure the re-formation of inter-chain disulfide bonds. The samples were buffer exchanged into PBS. The maleimide-linked drug payload, Tap18Hr1, was then added to react with free-thiols on the processed antibody. The excess payload was quenched with N-acetyl-L-cysteine (SIGMA-ALDRICH®, Cat. No: A7250) and CHT ceramic hydroxyapatite beads (BIO-RAD®, Cat. No: 157-0040) were used to purify the site-specific conjugated hLK26-Cys variants-Tap18Hr1, hLK26-T155C-Tap18Hr1, and hLK26-S442C-Tap18Hr1.

A reducing/oxidation procedure was also used with some modifications to specifically conjugate linker payload on the introduced cysteine at T199 of the heavy chain and at L201 and T206 of the kappa light chain. The hLK26 heavy chain mutant of T199C and light chain mutant of L201C and T206C were first treated with 15~50 fold molar excess of TCEP (ACROS ORGANICS®, Cat. No: 363830100) at 37° C. for 2~5 hours in PBS (GIBCO®, Cat. No: 21600-069) containing 1-50 mM DTPA (SIGMA-ALDRICH®, Cat. No: D6518 or E5134). After removing the excess TCEP, the antibody was then re-oxidized with dehydroascorbic acid (DHA) (SIGMA-ALDRICH®, Cat. No: 261556) with 50~70 fold molar excess over protein at 4° C. for 2~5 hours to ensure the re-formation of inter-chain disulfide bonds. The samples were buffer exchanged into PBS. The maleimide-linked drug payload, Tap18Hr1, was then added to react with free-thiols on the processed antibody. The excess payload was quenched with N-acetyl-L-cysteine (SIGMA-ALDRICH®, Cat. No: A7250) and CHT ceramic hydroxyapatite beads (BIO-RAD®, Cat. No: 157-0040) were used to purify these site-specific ADCs.

Drug Antibody Ratio (DAR) Determination by Reverse Phase HPLC Analysis

A method consisting of reducing and denaturing reversed-phase HPLC (RP-HPLC) was developed to separate and quantify various light and heavy chain species to determine the DAR of conjugated ADC. Prior to HPLC analysis, conjugate sample was treated with 6M guanidine hydrochloride and 20 mM DTT under 50° C. heating for 15 mins. 100 µg of the treated conjugate sample was applied to PLRP-S column (2.1×150 mm, 8 µm, 1000 Å, Aligent). The flow rate was set at 0.8 mL/min and the column temperature was set at 80° C. constantly throughout the analysis. Solvent A was 0.05% trifluoroacetic acid in Milli Q water and solvent B was 0.04% trifluoroacetic acid in acetonitrile. The gradient program consisted of the following: Isocratic 25% B for 3 ml, a 25 ml linear gradient to 50% B, a 2 ml linear gradient to 95% B, a 1 ml linear gradient to 25% B, and isocratic 25% B for 2 ml. In this method, pretreatment of the ADC with an excess of DTT breaks the inter- and intra-chain disulfides and allows separation of light chain with 0 or 1 drug (L0 and L1) from heavy chain with 0, 1, 2, or 3 drugs (H0, H1, H2, and H3). Peaks of each separated species were assigned by their elution time and UV spectra (the A248/280 ratio increases with drug loading). The calculated DAR based on the area of individual peak in the RP-HPLC profile for the tested ADCs is listed in Table 7A and Table 7B.

TABLE 7

| Drug Antibody Ratio | |
|---|---|
| hLK26-ADC | DAR range |
| (A) Measurement 1 | |
| hLK26-IgG1-Tap18Hr1 (conventional ADC) | 2.6~3.0 |
| hLK26-Cys-variants-Tap18Hr1 (site-specific ADCs) | 1.80~1.94 |

TABLE 7-continued

Drug Antibody Ratio

| hLK26-ADC | DAR range |
|---|---|
| (B) Measurement 2 | |
| hLK26-IgG1-Tap18Hr1 (conventional ADC) | 2.49~3.00 |
| hLK26- T155C-Tap18Hr1 hLK26- T199C-Tap18Hr1 hLK26- S442C-Tap18Hr1 (site-specific ADCs with heavy chain mutants) | 1.77~1.97 |
| hLK26-T206C-Tap18Hr1 hLK26-L201C-Tap18Hr1 (site-specific ADCs with kappa light chain mutants) | 1.74~1.87 |

Binding of hLK26-Cys-Variants and the Tap18Hr1 Conjugates to Cancer Cells $1 \times 10^5$ cells were seeded per well in a v-bottomed 96-well plate and incubated with 50 µl of the unconjugated Abs or the ADCs at titrated concentrations or isotype control antibody human IgG at 10 µg/mL. After 60 minutes of incubation at 4° C., cells were washed once with 200 µl FACS buffer (1×PBS containing 1% FBS), stained with 50 µl of 1 µg/ml goat F(ab')2-anti-human IgG (H+L)-RPE or goat anti-human IgG-RPE (SOUTHERN BIOTECH®, Cat. No. 2043-09 or 2040-09) in FACS buffer and then incubated at 4° C. for 30 min Cells were washed once with FACS buffer and analyzed by flow cytometer (BD LSR, BD Life Sciences).

In Vitro WST-8 Cytotoxicity Assay

SK-OV-3, OVCAR-3, OVCAR-3B and Panc 02.03B cells were seeded $1 \times 10^3 \sim 1 \times 10^4$ cells per well, respectively, on 96-well microtiter plates. Tap18Hr1 conjugated ADCs or unconjugated antibodies were added in triplicates or quintuplicate at the final indicated concentrations in a final volume 200 µL/well range from 600 nM to 0.03 nM (90 µg/ml to 0.005 µg/ml) with 2.5-fold or 3-fold serial dilution for SK-OV-3 and Panc02.03B and 200 nM to 0.01 nM (30 µg/ml to 0.005 µg/ml) with 3-fold serial dilution for OVCAR-3 and OVCAR-3B. Cells were then incubated at 37° C. and 5% $CO_2$ After incubation of 3 days for OVCAR-3 and 3-6 days for SK-OV-3, Panc02.03B and OVCAR-3B, cell viability was measured by the Cell Counting Kit-8 (Dojindo, Cat. No. CK04) followed manufacturer's instructions. In brief, at the end of incubation 100 µL/well of medium was removed and 10 µL/well of reagent dye (WST-8) was added into each well. After optimal colour development (when $OD_{450}$ of untreated control ≥1), absorbance at 450 nm ($OD_{450}$ value) was measured by spectrophotometer (MOLECULAR DEVICES®, VERSAMAX™ microplate reader). The mean of the replicates was obtained and background (medium control) was subtracted. The resultant $OD_{450}$ values were then used to calculate % growth inhibition according to the following formula: [$OD_{450}$ untreated–$OD_{450}$ sample]/[$OD_{450}$ untreated]*100.

ADC Treatment in Cancer Xenograft Model

Ovarian Tumor SK-OV-3 Treated with hLK26-IgG1-Tap18Hr1

To establish a subcutaneous xenograft model, $1 \times 10^7$ SK-OV-3 cells in 120 µL of PBS containing 25% BD MATRIGEL™ basement membrane matrix high Concentration (BD Biosciences, Cat. No. 354248) were implanted into the right flank of 6-week-old female C.B-17 SCID mice (Lasco, Taipei, Taiwan). hLK26-IgG1-Tap18Hr1 was injected intravenously at 3 mg/kg in 100 µL approximately 1 hour after tumor cell inoculation (marked as Day 1). Tumor volume was measured once weekly with a caliper in two perpendicular dimensions, and calculated according to the formula (0.52*length*width*width). To determine the potential drug toxicity in the treated mice, the body weights were recorded weekly.

Ovarian Tumor SK-OV-3 Treated with hLK26-Cys Variants Conjugated with Tap18Hr1

To establish a subcutaneous xenograft model, $1 \times 10^7$ SK-OV-3 cells in 100 µL of PBS containing 50% BD MATRIGEL™ basement membrane matrix (BD Biosciences, Cat. No. 354234) were implanted into the right flank of 6-week-old female C.B-17 SCID mice (Lasco, Taipei, Taiwan). Site-specific ADCs hLK26-Cys variants-Tap18Hr1 were each injected intravenously at 5 mg/kg in 150 µL approximately 2 hour after tumor cell inoculation (marked as Day 1). Tumor volume was measured once weekly with a caliper in two perpendicular dimensions, and calculated according to the formula (0.52*length*width*width). To determine the potential drug toxicity in the treated mice, the body weights were recorded weekly.

Lung Tumor NCI-H2110 Treated with Conventional hLK26-IgG1-Tap18Hr1 and Site-Specific Conjugated hLK26-Cys Variants-Tap18Hr1

To establish a subcutaneous xenograft lung tumor model, $5 \times 10^6$ NCI-H2110 cells in 100 µL of PBS were implanted into the right flank of 6-week-old female C.B-17 SCID mice (Lasco, Taipei, Taiwan). Conventional conjugated hLK26-IgG1-Tap18Hr1 and site-specific hLK26-Cys variants-Tap18Hr1 were each injected intravenously at 5 mg/kg in 150 µL approximately 6 hour after tumor cell inoculation (marked as Day 1). Tumor volume was measured once weekly with a caliper in two perpendicular dimensions, and calculated according to the formula (0.52*length*width*width). To determine the potential drug toxicity in the treated mice, the body weights were recorded weekly.

Example 2: Binding Activity of hLK26 Based Antibody Drug Conjugates (ADCs) in Ovarian and Lung Cancer Cells hLK26-IgG1-Tap18Hr1 Binding Activity The binding activity of hLK26-IgG1 naked Ab and hLK26-IgG1-Tap18Hr1 was evaluated by flow cytometric analysis in FRA-expressing SK-OV-3, OVCAR-3, NCI-H2110 and NCI-H292 cells. Results (Table 8) are shown as the mean fluorescence intensity (MFI) at which the most optimal binding was achieved with a series of Ab/ADC concentrations. hLK26-IgG1-Tap18Hr1 binds positively to all FRA expression cell lines tested, and displays equivalent binding ability with the naked Ab hLK26-IgG1. These data demonstrate that conventional ADC hLK26-IgG1-Tap18Hr1 retains antigen reactivity of hLK26-IgG1 and binds to FRA-expressing cancer cells effectively.

TABLE 8

Binding of hLK26-IgG1-Tap18Hr1 and unconjugated hLK26-IgG1 to cancer cells

| | | hLK26-IgG1 - Tap18Hr1 (1.1 µg/mL) | hLK26-IgG1 (1.1 µg/mL) | Isotype control (10 µg/mL) |
|---|---|---|---|---|
| Ovarian cancer cell | OVCAR-3 | 1114 | 1154 | 7 |
| | SK-OV-3 | 2973 | 3174 | 6 |
| Lung cancer cell | NCI-H2110 | 666 | 644 | 5 |
| | NCI-H292 | 1420 | 1398 | 6 |

The binding activities of site-specific conjugates of hLK26-Cys variants-Tap18Hr1 were evaluated by flow cytometric analysis in ovarian cancer SK-OV-3 and OVCAR-3B (Table 9-10) and lung cancer NCI-H2110 and NCI-H292 (Table 11-12) cells. The Mean fluorescence intensity (MFI) values in the tables represent binding activity of ADCs at tested concentration. Among IgG1 variants, hLK26-T155C-IgG1-Tap18Hr1 and hLK26-T206C-IgG1-Tap18Hr1 bound comparably with the wild type, naked hLK26-IgG1, but hLK26-S442C-IgG1-Tap18Hr1 showed slightly decrease in binding reactivity. The IgG4p variants-Tap18Hr1 conjugates also bind to all the FRA positive cancer cells tested here, but the fluorescent intensities were generally lower than those observed with IgG1 variants. This decrease in binding activity is likely attributed to IgG4 isotype rather than cysteine mutation. Overall, the site-specific conjugated hLK26-Cys variants retain antigen reactivity to the ovarian and lung cancer cells tested.

TABLE 9

Binding of unconjugated hLK26-IgG1 and hLK26-Cys variants-Tap18Hr1 to SK-OV-3 cells

| Antibody (1.1 µg/mL) | MFI |
|---|---|
| (1) The site-specific ADC of T155C and S442C mutants | |
| hLK26-T155C-IgG4p-Tap18Hr1 | 1888 |
| hLK26- S442C-IgG4p-Tap18Hr1 | 1885 |
| hLK26-T155C-IgG1-Tap18Hr1 | 2474 |
| hLK26- S442C-IgG1-Tap18Hr1 | 2077 |
| hLK26-IgG1 | 2446 |
| 2$^{nd}$ Ab only | 6 |
| (2) The site-specific ADC of T199C, L201C and T206C mutants | |
| hLK26-T199C-IgG4p-Tap18Hr1 | 966 |
| hLK26-L201C-IgG4p-Tap18Hr1 | 1004 |
| hLK26-T206C-IgG1-Tap18Hr1 | 1274 |
| hLK26-IgG1 | 1403 |
| 2$^{nd}$ Ab only | 5 |

TABLE 10

Binding of unconjugated hLK26-IgG1 and hLK26-Cys variants-Tap18Hr1 to OVCAR-3B cells

| Antibody (1.1 µg/mL) | MFI |
|---|---|
| hLK26-T155C-IgG4p-Tap18Hr1 | 806 |
| hLK26- S442C-IgG4p-Tap18Hr1 | 769 |
| hLK26-T155C-IgG1-Tap18Hr1 | 1062 |
| hLK26- S442C-IgG1-Tap18Hr1 | 967 |
| hLK26-IgG1 | 1154 |
| 2$^{nd}$ Ab only | 5 |

TABLE 11

Binding of unconjugated hLK26-IgG1 and hLK26-Cys variants-Tap18Hr1 to NCI-H2110 cells

| Antibody (3.3 µg/mL) | MFI |
|---|---|
| (1) The site-specific ADC of T155C and S442C mutants | |
| hLK26-T155C-IgG4p-Tap18Hr1 | 494 |
| hLK26- S442C-IgG4p-Tap18Hr1 | 479 |
| hLK26-T155C-IgG1-Tap18Hr1 | 649 |
| hLK26- S442C-IgG1-Tap18Hr1 | 605 |
| hLK26-IgG1 | 679 |
| 2$^{nd}$ Ab only | 5 |
| (2) The site-specific ADC of T199C, L201C and T206C mutants | |
| hLK26-T199C-IgG4p-Tap18Hr1 | 898 |
| hLK26-L201C-IgG4p-Tap18Hr1 | 890 |
| hLK26-T206C-IgG1-Tap18Hr1 | 1180 |
| hLK26-IgG1 | 1186 |
| 2$^{nd}$ Ab only | 5 |

TABLE 12

Binding of unconjugated hLK26-IgG1 and hLK26-Cys variants-Tap18Hr1 to NCI-H292 cells

| Antibody (3.3 µg/mL) | MFI |
|---|---|
| hLK26-T155C-IgG4p-Tap18Hr1 | 1179 |
| hLK26- S442C-IgG4p-Tap18Hr1 | 1087 |
| hLK26-T155C-IgG1-Tap18Hr1 | 1447 |
| hLK26- S442C-IgG1-Tap18Hr1 | 1281 |
| hLK26-IgG1 | 1455 |
| 2$^{nd}$ Ab only | 6 |

Example 3: In Vitro Cytotoxicity of hLK26-IgG1-Tap18Hr1 ADC and hLK26-IgG1 in FRA-Expressing Cell Lines The in vitro cytotoxic activity of hLK26-IgG1-Tap18Hr1 was evaluated in the FRA positive cancer cell lines (SK-OV-3 and OVCAR-3) and FRA negative cell line (Panc 02.03B). Cytotoxicity by the naked hLK26-IgG1 antibody was also tested in parallel. ADC hLK26-IgG1-Tap18Hr1 induced specific and a dose-dependent growth inhibition for FRA positive cancer cells (SK-OV-3 and OVCAR-3), while it had much less growth inhibition effect on the FRA-negative cell Panc 02.03B, demonstrating the antigen specificity of this cytotoxicity (Table 13). Compared to ADCs, naked Ab hLK26-IgG1 had negligible impact on the viability of treated cells.

TABLE 13

In vitro cytotoxic activity of hLK26-IgG1-Tap18Hr1 and hLK26-IgG1

| | | % growth inhibition | |
|---|---|---|---|
| Concentration of Ab/ADC tested | | 3 µg/mL | 1 µg/mL |
| SK-OV-3 | hLK26 -IgG1-Tap18Hr1 | 87.2 | 79.6 |
| | hLK26-IgG1 | 3.1 | 1.0 |
| OVCAR-3 | hLK26 -IgG1-Tap18Hr1 | 99.2 | 98.3 |
| | hLK26-IgG1 | 18.0 | 8.2 |
| Panc 02.03B | hLK26 -IgG1-Tap18Hr1 | 15.9 | 6.5 |
| | hLK26 -IgG1 | 5.1 | 1.3 |

The in vitro cytotoxic activity of the site-specific conjugated hLK26 Cys variants-Tap18Hr1 was also evaluated in SK-OV-3 and OVCAR-3B cells. Table 14 shows the result of IgG1 variants and Table 15 shows IgG4p variants. Like conventional conjugated ADC (Table 13), hLK26 Cys variants-Tap18Hr1 induced specific and a dose-dependent growth inhibition for FRA positive cancer cells (SK-OV-3 and OVCAR-3). They had much less impact on the viability of FRA-negative cell Panc 02.03B, demonstrating the antigen specificity of this cytotoxicity (Table 14 and 15). These results demonstrate that both conventional and site-specific conjugated hLK26-Tap18Hr1 ADCs can deliver cytotoxic drug to the target cancer cells with antigen specificity.

TABLE 14

In vitro cytotoxic activity of the
conjugated hLK26 IgG1 Cys variants

| | | % growth inhibition | |
|---|---|---|---|
| Concentration of ADC tested | | 10 μg/mL | 3 μg/mL |
| SK-OV-3 | hLK26-S442C-IgG1-Tap18Hr1 | 79.1 | 34.9 |
| | hLK26-T155C-IgG1-Tap18Hr1 | 85.9 | 53.1 |
| OVCAR-3B | hLK26-S442C-IgG1-Tap18Hr1 | 108.0 | 74.4 |
| | hLK26-T155C-IgG1-Tap18Hr1 | 99.9 | 85.3 |
| Panc 02.303B | hLK26-S442C-IgG1-Tap18Hr1 | 17.5 | 5.5 |
| | hLK26-T155C-IgG1-Tap18Hr1 | 26.1 | 10.7 |

TABLE 15

In vitro cytotoxic activity of the
conjugated hLK26 IgG4p Cys variants

| | | % growth inhibition | |
|---|---|---|---|
| Concentration of ADC tested | | 10 μg/mL | 3 μg/mL |
| SK-OV-3 | hLK26 -T155C-IgG4P-Tap18Hr1 | 78.6 | 41.6 |
| | hLK26 -S442C-IgG4P-Tap18Hr1 | 58.7 | 27.0 |
| OVCAR-3B | hLK26 -T155C-IgG4P-Tap18Hr1 | 99.5 | 52.4 |
| | hLK26 -S442C-IgG4P-Tap18Hr1 | 89.5 | 21.6 |
| Panc 02.03B | hLK26 -T155C-IgG4P-Tap18Hr1 | 25.2 | 7.2 |
| | hLK26 -S442C-IgG4P-Tap18Hr1 | 6.7 | 6.5 |

Figure 4:
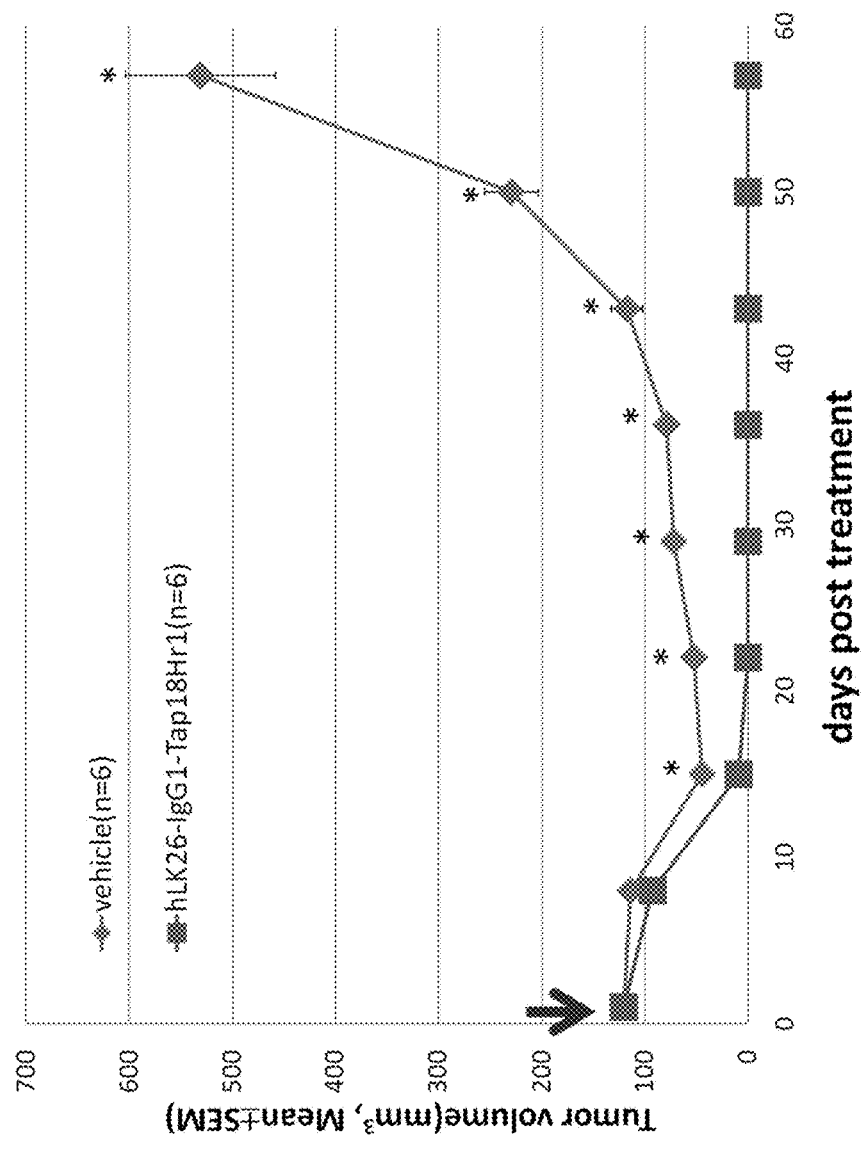
FIG. 4 shows in vivo anti-tumor activity of hLK26-IgG1-Tap18Hr1 against xenograft derived from ovarian cancer cell line SK-OV-3.

Example 4: In Vivo Efficacy of Conventional ADC hLK26-IgG1-Tap18Hr1 in Ovarian Cancer Potency of hLK26-IgG1-Tap18Hr1 was evaluated in vivo in xenograft models derived from the ovarian cancer cells SK-OV-3. Mice were treated intravenously with vehicle (PBS) or a single dose of ADC at 3 mg/kg, approximately one hour after tumor cell implantation (marked as Day 1, see arrow in FIG. 4). The tumor size on Day 1 was thus recorded as 120 mm$^3$ due to the inoculation volume of cell-Matrigel mixture. The injected Matrigel appeared to be absorbed by day 15, during which tumor was established and grew steadily as observed in the vehicle control group. By Day 57, the mean tumor size of vehicle control had reached over 500 mm$^3$ (FIG. 4), while no tumor growth was detected in the group of mice (6 out of 6) treated with hLK26-IgG1-Tap18Hr1 by the end of study. No toxicity was observed as body weight change of both groups remained no difference (data not shown). Therefore, the study demonstrated that hLK26-IgG1-Tap18Hr1 ADC alone is a potent anti-tumor agent for ovarian cancer.

Figure 5:
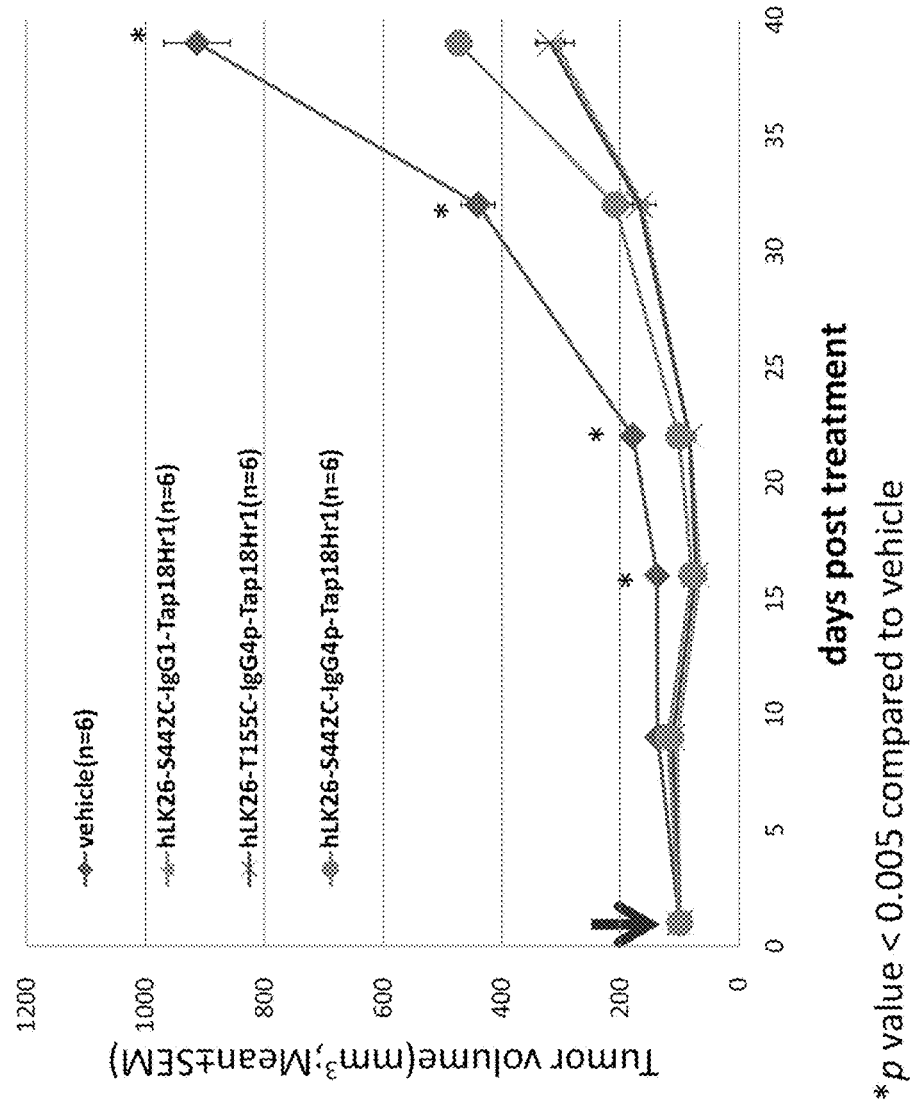
FIG. 5 shows in vivo anti-tumor activity of the site-specific conjugated hLK26-Tap18Hr1 ADCs hLK26-S442C-IgG1-Tap18Hr1, hLK26-T155C-IgG4p-Tap18Hr1, and hLK26-S442C-IgG4p-Tap18Hr1 against xenograft derived from ovarian cancer cell line SK-OV-3.

Example 5: In Vivo Efficacy of Site Specific ADC hLK26 Cys Variants-Tap18Hr1 in Ovarian Cancer The SK-OV-3 xenograft model in SCID mice was also used to evaluate the anti-tumor effect of the site-specific conjugated hLK26 Cys variants-Tap18Hr1 in vivo. The cancer cells were grafted into SCID mice subcutaneously and a single dose of 5 mg/kg ADCs or vehicle control was given approximately two hours after tumor cells implantation (marked as Day 1). Four treatment groups were compared: hLK26-S442C-IgG1-Tap18Hr1, hLK26-T155C-IgG4P-Tap18Hr1, hLK26-S442C-IgG4P-Tap18Hr1 and vehicle control, with 6 mice in each treatment group. The sizes of the tumors were measured once weekly. The results are shown in FIG. 5. The tumor size on Day 1 was recorded as 100 mm$^3$ due to the volume of inoculated cell-Matrigel mixture. As compared to vehicle control, a single dose of 5 mg/kg hLK26 Cys variants-Tap18Hr1 significantly delayed the tumor growth in all ADC treated groups (p value <0.005 since day 16 after treatment). The arrow in FIG. 5 indicates the time of treatment given. There is also no obvious toxicity observed in the group of mice treated with ADCs as body weight gain of all groups remained no difference (data not shown). The study demonstrated that the site-specific conjugated hLK26 Cys variants-Tap18Hr1 are effective anti-tumor agents for ovarian cancer, even some decrease in cell binding activity was seen with some variants.

Figure 6:
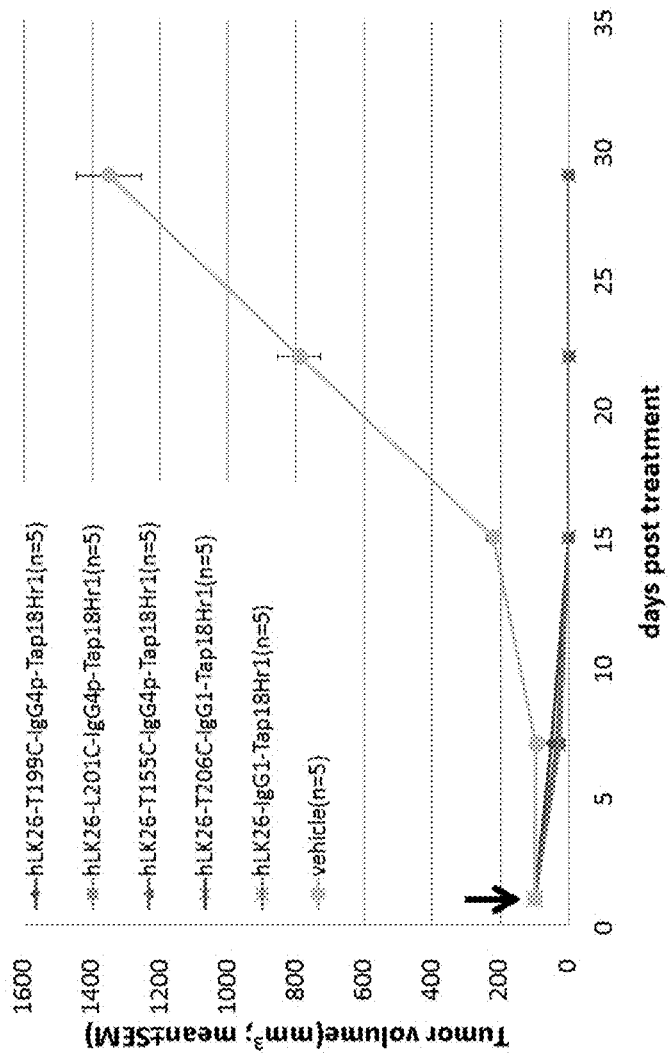
FIG. 6 shows in vivo anti-tumor activity of the conventional hLK26-IgG1-Tap18Hr1, and site-specific conjugated hLK26-Tap18Hr1 ADCs hLK26-T206C-IgG1-Tap18Hr1, hLK26-T155C-IgG4p-Tap18Hr1, hLK26-T199C-IgG4p-Tap18Hr1 and hLK26-L201C-IgG4p-Tap18Hr1 against xenograft derived from lung cancer cell line NCI-H2110.

Example 6: In Vivo Anti-Tumor Activity of Anti-FRA Based Tap18Hr1 Conjugates Against Lung Cancer The efficacy of conventional and site-specific Anti-FRA-Tap18Hr1 conjugates was evaluated in vivo in xenograft models derived from lung cancer cells NCI-H2110. The cancer cells were grafted into SCID mice subcutaneously and a single dose of 5 mg/kg ADCs including hLK26-IgG1-Tap18Hr1, hLK26-T206C-IgG1-Tap18Hr1, LK26-T155C-IgG4p-Tap18hr1, hLK26-T199C-IgG4p-Tap18Hr1, and hLK26-L201C-IgG4p-Tap18Hr1 or vehicle control, were given approximately 6 hours after tumor cells implantation (marked as Day 1, see arrow in FIG. 6) The tumor size on Day 1 recorded as 100 mm$^3$ due to the volume of inoculated cell mixture. Each treatment group with 5 animals was measured the sizes of the tumor once weekly. A single dose of 5 mg/kg either conventional hLK26-IgG1-Tap18Hr1 or site-specific hLK26 Cys variants-Tap18Hr1 conjugates completely inhibited tumor growth in the treated mice. No tumor growth was detected up to day 29 in all ADC treated groups. By contrast, the tumor of vehicle group grew rapidly and reached over 1000 mm$^3$ at day 29 (p value <0.05 since day 7 after treatment). There is no obvious toxicity observed in the group of mice treated with ADCs as body weight gain of all groups remained no difference (data not shown). The study demonstrated that either conventional or site-specific Anti-FRA based Tap18Hr1 conjugates, they alone are a potent anti-tumor agent for lung cancer.

REFERENCES

1. Carter, P J and Senter, P D. Antibody-drug conjugates for cancer therapy. Cancer J. 2008; 14: 154-169)
2. Teicher, B A. Antibody-drug conjugate targets. Current cancer Drug Targets 2009, 9: 982-1004.
3. Ducry, L and Stump, B. Antibody-drug conjugates: linking cytotoxic payloads to monoclonal antibodies. Bioconjugate chem., 2010, 21: 5-13.
4. Koblinski, J E., Ahram, M and Sloane, B F. Unraveling the role of proteases in cancer. Clin. Chem. Acta 2000; 291:113-135.

All patents, patent applications, documents, and articles cited herein are herein incorporated by reference in their entireties.

What is claimed is:

1. A compound of the formula (II):

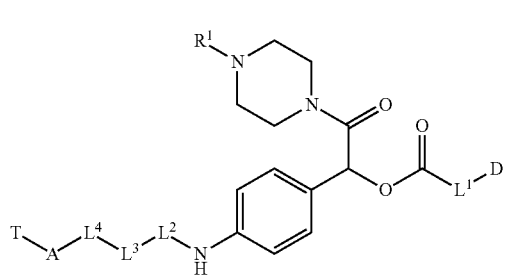

(II)

or a salt or solvate or stereoisomer thereof; wherein:
D is a drug moiety;
T is a targeting moiety which is an antibody that specifically binds to a human folate receptor alpha (FRA);
$R^1$ is hydrogen, unsubstituted or substituted $C_{1-3}$ alkyl, or unsubstituted or substituted heterocyclyl;
$L^1$ is a bond, a second self-immolative linker, or a cyclization self-elimination linker;
$L^2$ is a bond or a second self-immolative linker;
wherein if $L^1$ is a second self-immolative linker or a cyclization self-elimination linker, then $L^2$ is a bond;
wherein if $L^2$ is a second self-immolative linker, then $L^1$ is a bond;
$L^3$ is a peptide linker;
$L^4$ is a bond or a spacer; and
A is an acyl unit;

wherein:
(i) the antibody comprises a heavy chain comprising the amino acid sequence of SEQ ID NO: 1, and a light chain comprising the amino acid sequence of SEQ ID NO: 3, wherein an amino acid residue at position 201 in the light chain constant region is replaced with a cysteine residue; or
(ii) the antibody comprises a heavy chain comprising the amino acid sequence of SEQ ID NO: 2, and a light chain comprising the amino acid sequence of SEQ ID NO: 3, wherein an amino acid residue at position 199 in the heavy chain constant region is replaced with a cysteine residue, and/or wherein an amino acid residue at position 201 in the light chain constant region is replaced with a cysteine residue;
wherein the numbering is according to the EU index of Kabat; and
wherein D is linked to T via a cysteine residue connected through the linker moiety

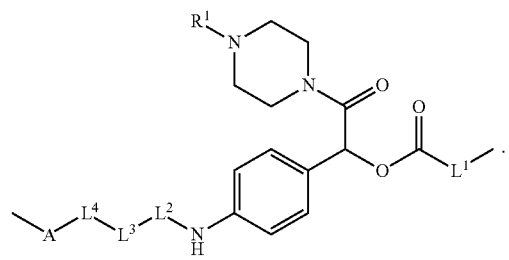

2. A compound of the formula (IIa):

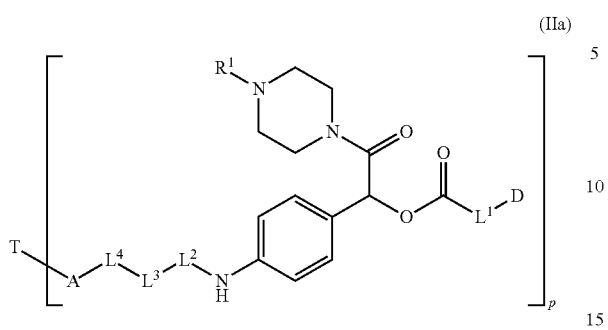

or a salt or solvate or stereoisomer thereof; wherein:
p is 1 to 20;
D is a drug moiety;
T is a targeting moiety which is an antibody that specifically binds to a human folate receptor alpha (FRA);
$R^1$ is hydrogen, unsubstituted or substituted $C_{1-3}$ alkyl, or unsubstituted or substituted heterocyclyl;
$L^1$ is a bond, a second self-immolative linker, or a cyclization self-elimination linker;
$L^2$ is a bond or a second self-immolative linker;
  wherein if $L^1$ is a second self-immolative linker or a cyclization self-elimination linker, then $L^2$ is a bond;
  wherein if $L^2$ is a second self-immolative linker, then $L^1$ is a bond;
$L^3$ is a peptide linker;
$L^4$ is a bond or a spacer; and
A is an acyl unit;
wherein:
(i) the antibody comprises a heavy chain comprising the amino acid sequence of SEQ ID NO: 1, and a light chain comprising the amino acid sequence of SEQ ID NO: 3, wherein an amino acid residue at position 201 in the light chain constant region is replaced with a cysteine residue; or
(ii) the antibody comprises a heavy chain comprising the amino acid sequence of SEQ ID NO: 2, and a light chain comprising the amino acid sequence of SEQ ID NO: 3, wherein an amino acid residue at position 199 in the heavy chain constant region is replaced with a cysteine residue, and/or wherein an amino acid residue at position 201 in the light chain constant region is replaced with a cysteine residue;
wherein the numbering is according to the EU index of Kabat; and
wherein D is linked to T via a cysteine residue connected through the linker moiety

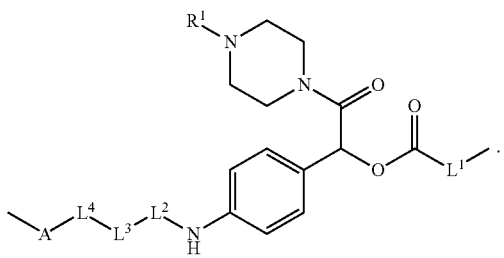

3. The compound of claim 2, wherein p is 1 to 4.
4. The compound of claim 2, wherein $L^1$ is a bond.

5. The compound of claim 2, wherein $L^1$ is a second self-immolative linker or a cyclization self-elimination linker.
6. The compound of claim 5, wherein $L^1$ is an aminobenzyloxycarbonyl linker.
7. The compound of claim 5, wherein $L^1$ is selected from the group consisting of

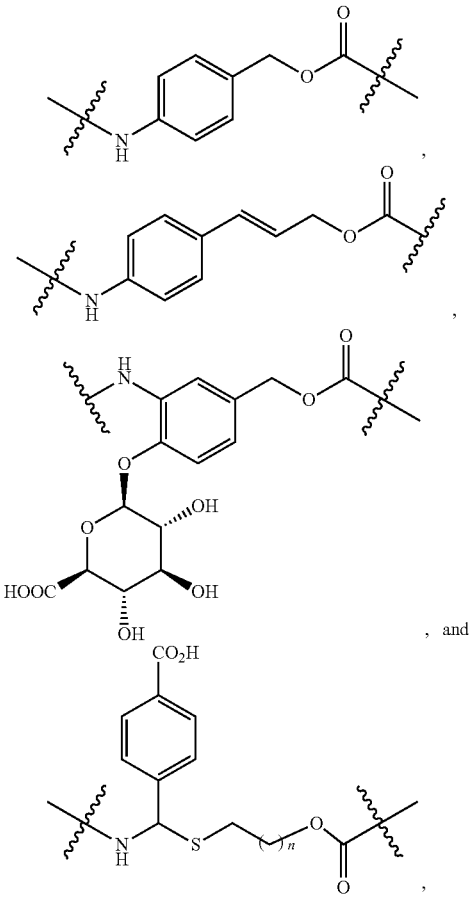

wherein n is 1 or 2.
8. The compound of claim 5, wherein $L^1$ is selected from the group consisting of

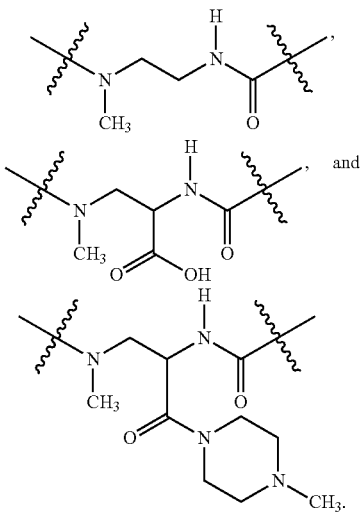

9. The compound of claim 2, wherein $L^2$ is a bond.

10. The compound of claim 4, wherein $L^2$ is a second self-immolative linker.

11. The compound of claim 10, wherein $L^2$ is an aminobenzyloxycarbonyl linker.

12. The compound of claim 10, wherein $L^2$ is selected from

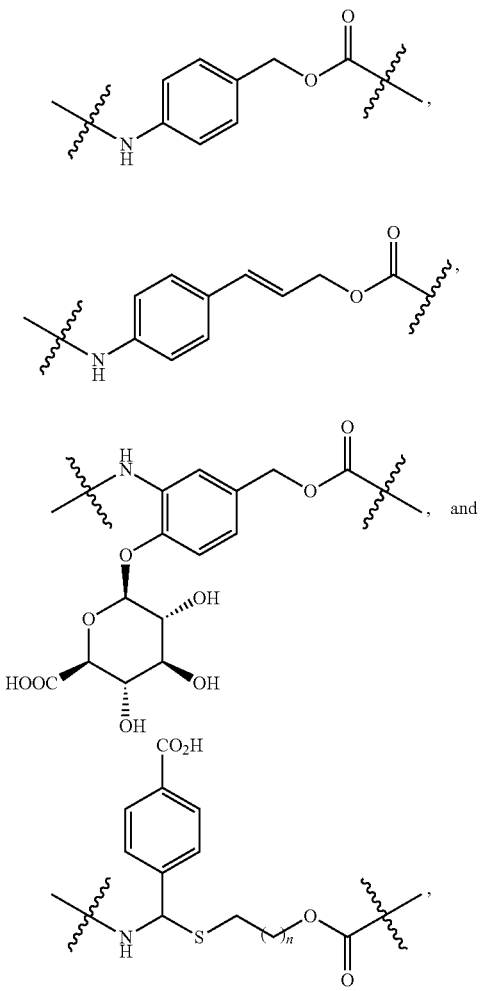

wherein n is 1 or 2.

13. The compound of claim 2, wherein $L^3$ is a peptide linker of 1 to 10 amino acid residues.

14. The compound of claim 13, wherein $L^3$ is a peptide linker of 2 to 4 amino acid residues.

15. The compound of claim 2, wherein $L^3$ is a peptide linker comprising at least one lysine or arginine residue.

16. The compound of claim 2, wherein $L^3$ is a peptide linker comprising an amino acid residue selected from lysine, D-lysine, citrulline, arginine, proline, histidine, ornithine and glutamine.

17. The compound of claim 2, wherein $L^3$ is a peptide linker comprising an amino acid residue selected from valine, isoleucine, phenylalanine, methionine, asparagine, proline, alanine, leucine, tryptophan, and tyrosine.

18. The compound of claim 13, wherein $L^3$ is a dipeptide unit selected from valine-citrulline, proline-lysine, methionine-D-lysine, asparagine-D-lysine, isoleucine-proline, phenylalanine-lysine, and valine-lysine.

19. The compound of claim 18, wherein $L^3$ is valine-citrulline.

20. The compound of claim 2, wherein $L^4$ is a bond.

21. The compound of claim 2, wherein $L^4$ is a spacer.

22. The compound of claim 21, wherein the spacer is polyalkylene glycol, alkylene, alkenylene, alkynylene, or polyamine.

23. The compound of claim 21, wherein $L^4$ is $L^{4a}$-C(O), $L^{4a}$-C(O)—NH, $L^{4a}$-S(O)$_2$, or $L^{4a}$-S(O)$_2$—NH, wherein each $L^{4a}$ is independently polyalkylene glycol, alkylene, alkenylene, alkynylene, or polyamine.

24. The compound of claim 21, wherein $L^4$ is $L^{4a}$-C(O), wherein $L^{4a}$ is polyalkylene glycol, alkylene, alkenylene, alkynylene, or polyamine.

25. The compound of claim 21, wherein $L^4$ is $L^{4a}$-C(O), wherein $L^{4a}$ is a polyalkylene glycol.

26. The compound of claim 21, wherein $L^4$ is $L^{4a}$-C(O), wherein $L^{4a}$ is a polyethylene glycol.

27. The compound of claim 21, wherein the spacer is of the formula —CH$_2$—(CH$_2$—O—CH$_2$)$_m$—CH$_2$—C(O)—, wherein m is an integer from 0 to 30.

28. The compound of claim 21, wherein $L^4$ is $L^{4a}$-C(O), wherein $L^{4a}$ is alkylene.

29. The compound of claim 2, wherein A is selected from the group consisting of

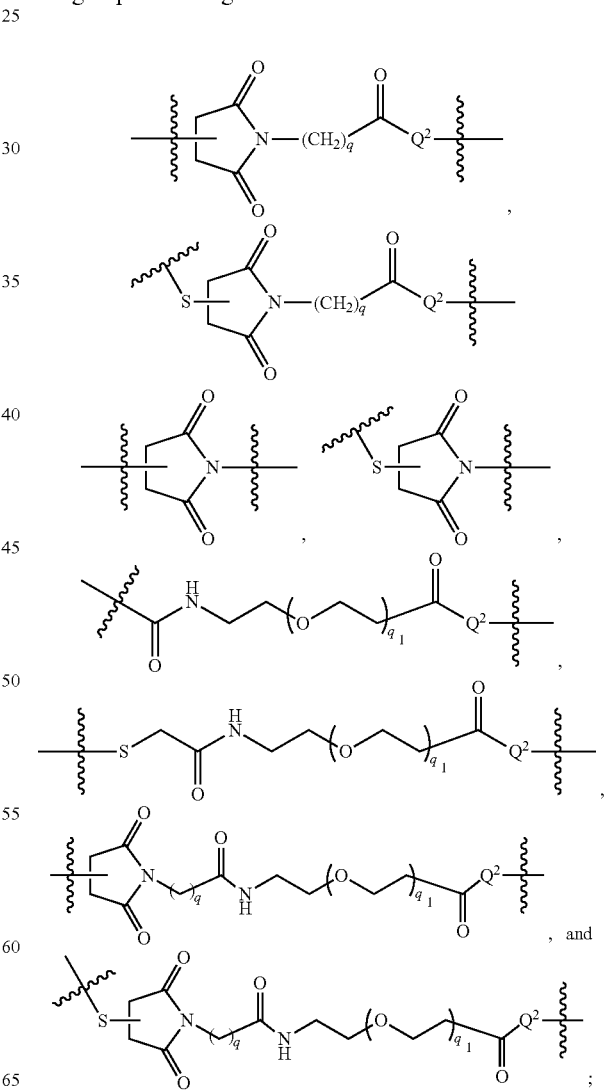

wherein each $Q^2$ is NH or O, each q is independently an integer from 1 to 10, and each $q_1$ is independently an integer from 1 to 10.

30. The compound of claim 29, wherein A is selected from the group consisting of

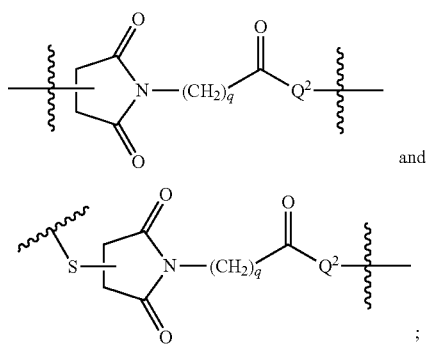

wherein each $Q^2$ is independently NH or O and each q is independently an integer from 1 to 10.

31. The compound of claim 30, wherein q is 2, 3, 4, or 5.

32. The compound of claim 2, wherein A is selected from the group consisting of

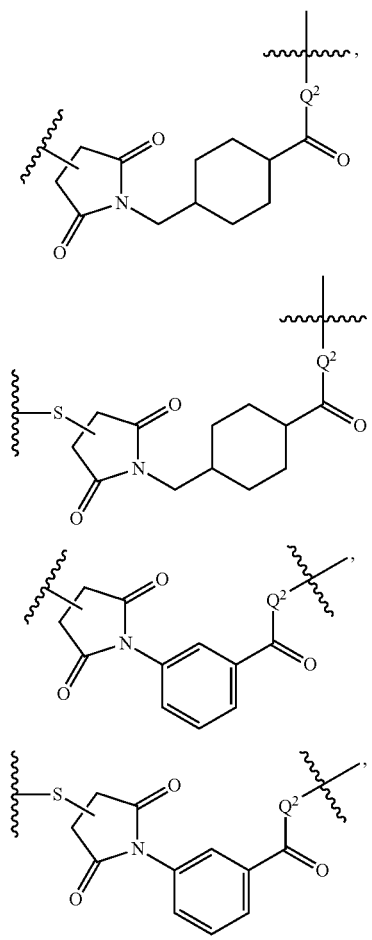

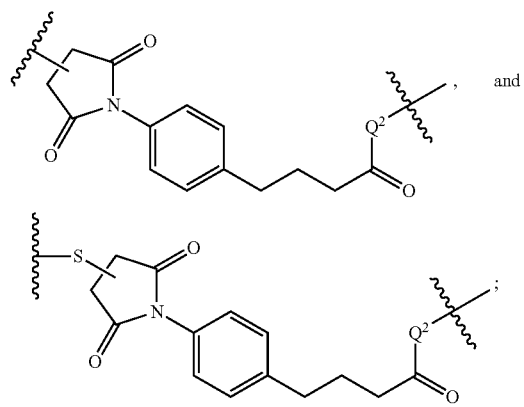

wherein each $Q^2$ is independently NH or O.

33. The compound of claim 2, wherein D is an amino-containing drug moiety, wherein the drug is connected to $L^1$ or X through the amino group.

34. The compound of claim 33, wherein D is duocarmycin, dolastatin, tubulysin, doxorubicin (DOX), paclitaxel, or mitomycin C (MMC), or an amino derivative thereof.

35. The compound of claim 33, wherein D is selected from the group consisting of

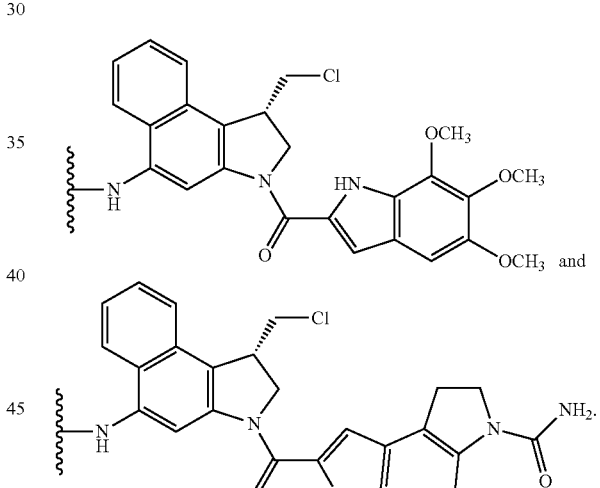

36. The compound of claim 33, wherein D is:

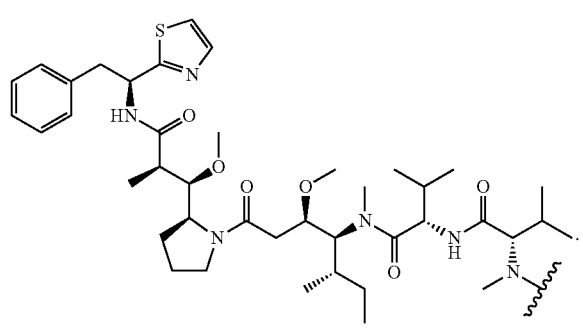 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)c1nccs1)OC)C(C)C)C(C)C]

37. The compound of claim 2, wherein A L⁴ L³ L² is
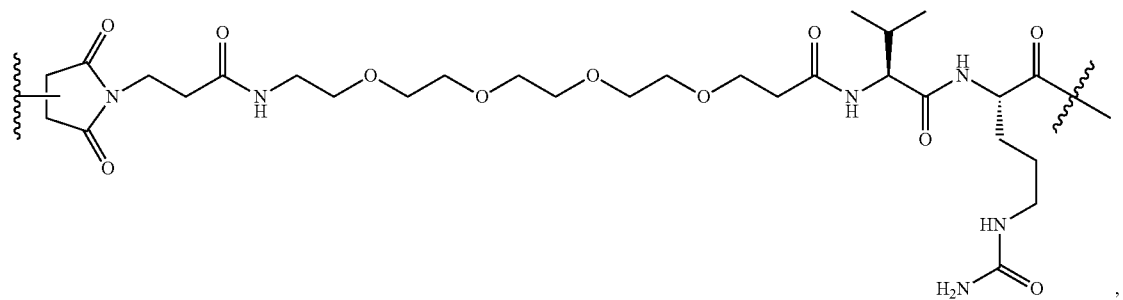
,
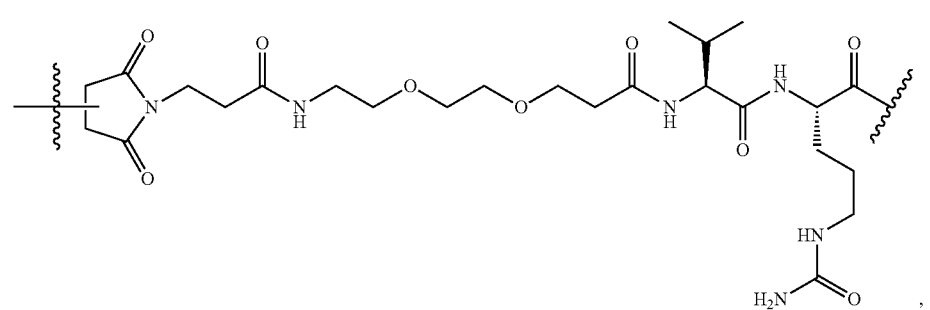
,
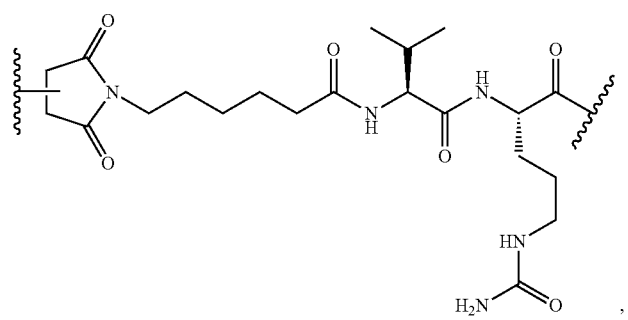
,
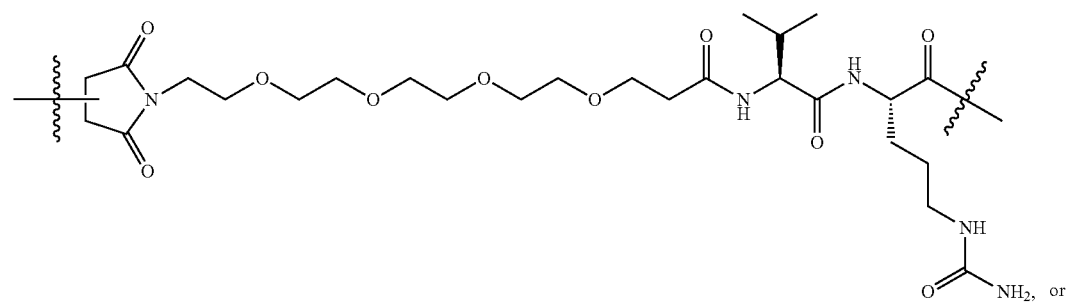
, or
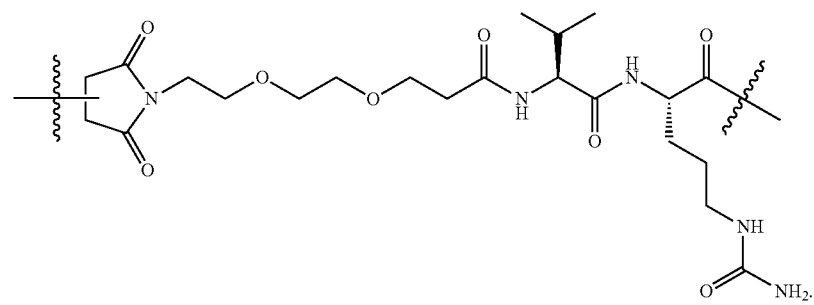
.

38. The compound of claim 2, wherein the
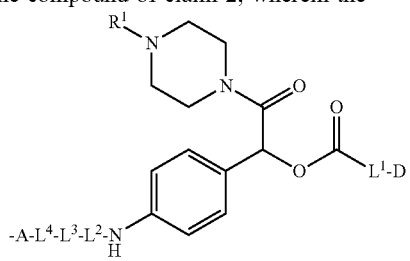
moiety is:
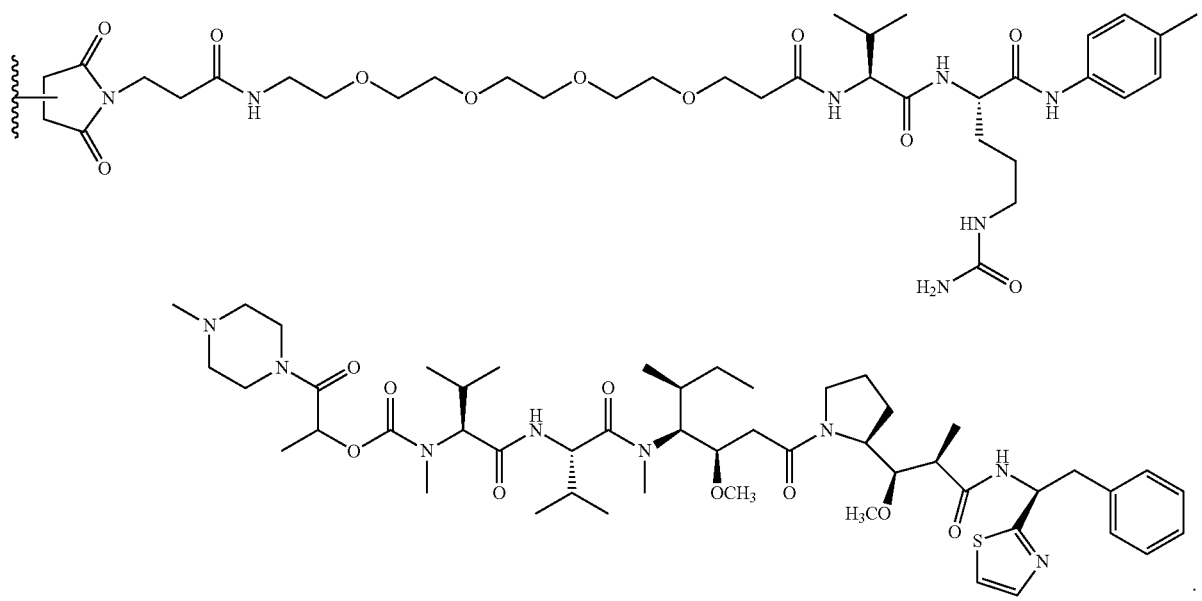
39. The compound of claim 2, wherein the
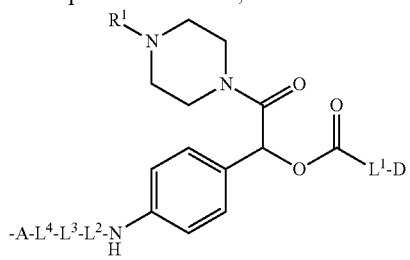
moiety is:
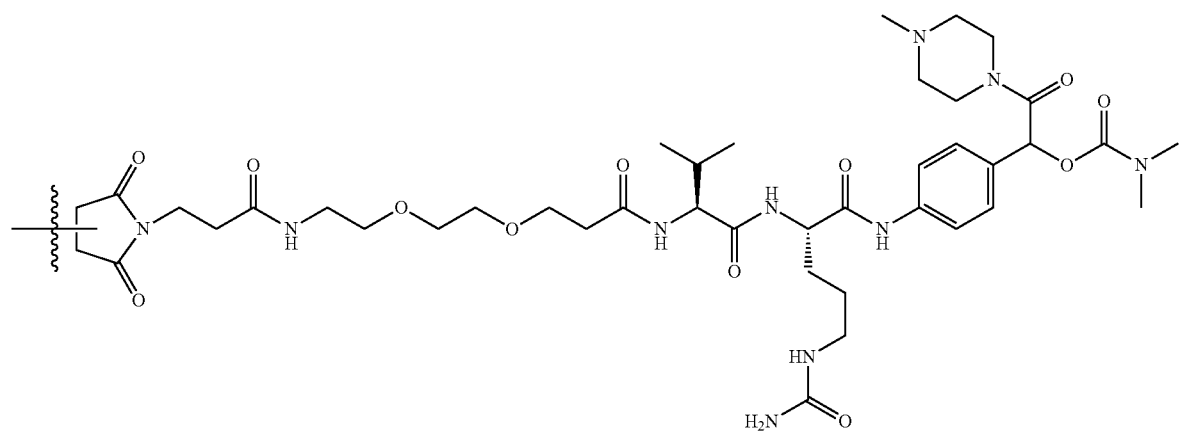

-continued

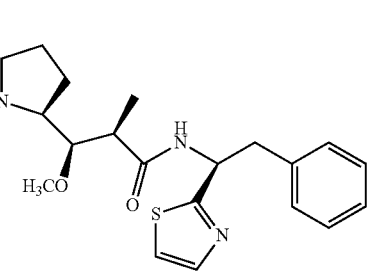

40. The compound of claim 2, wherein the

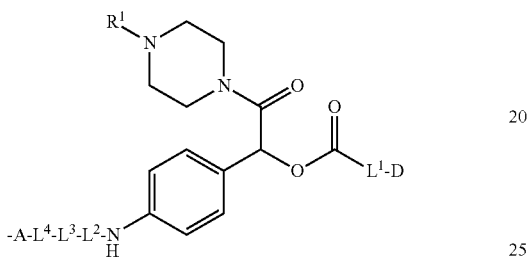

moiety is:

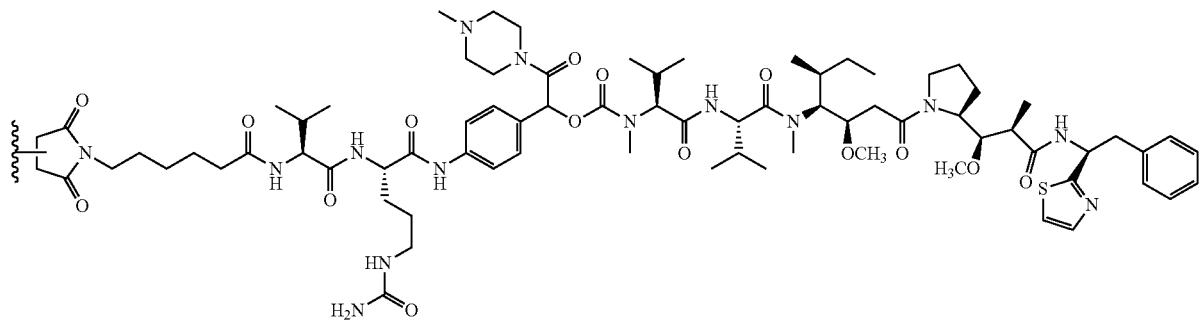

41. The compound of claim 2, wherein the anti-folate receptor alpha (FRA) antibody is a humanized antibody, a chimeric antibody or a human antibody.

42. A pharmaceutical composition comprising a compound of claim 2, or a salt or solvate or stereoisomer thereof; and a pharmaceutically acceptable carrier.

43. A kit comprising a compound of claim 2, or a salt or solvate or stereoisomer thereof.

44. The compound of claim 1, wherein the antibody comprises a heavy chain comprising the amino acid sequence of SEQ ID NO: 2, and a light chain comprising the amino acid sequence of SEQ ID NO: 3, and wherein an amino acid residue at position 199 in the heavy chain constant region is replaced with a cysteine residue.

45. The compound of claim 1, wherein the antibody comprises a heavy chain comprising the amino acid sequence of SEQ ID NO: 2, and a light chain comprising the amino acid sequence of SEQ ID NO: 3, and wherein an amino acid residue at position 201 in the light chain constant region is replaced with a cysteine residue.

46. The compound of claim 1, wherein the antibody comprises a heavy chain comprising the amino acid sequence of SEQ ID NO: 2, and a light chain comprising the amino acid sequence of SEQ ID NO: 3, wherein an amino acid residue at position 199 in the heavy chain constant region is replaced with a cysteine residue, and wherein an amino acid residue at position 201 in the light chain constant region is replaced with a cysteine residue.

47. The compound of claim 2, wherein the antibody comprises a heavy chain comprising the amino acid sequence of SEQ ID NO: 2, and a light chain comprising the amino acid sequence of SEQ ID NO: 3, and wherein an amino acid residue at position 199 in the heavy chain constant region is replaced with a cysteine residue.

48. The compound of claim 2, wherein the antibody comprises a heavy chain comprising the amino acid sequence of SEQ ID NO: 2, and a light chain comprising the amino acid sequence of SEQ ID NO: 3, and wherein an amino acid residue at position 201 in the light chain constant region is replaced with a cysteine residue.

49. The compound of claim 2, wherein the antibody comprises a heavy chain comprising the amino acid sequence of SEQ ID NO: 2, and a light chain comprising the amino acid sequence of SEQ ID NO: 3, wherein an amino acid residue at position 199 in the heavy chain constant region is replaced with a cysteine residue, and wherein an amino acid residue at position 201 in the light chain constant region is replaced with a cysteine residue.

* * * * *

UNITED STATES PATENT AND TRADEMARK OFFICE
CERTIFICATE OF CORRECTION

PATENT NO. : 9,950,077 B2  
APPLICATION NO. : 14/745336  
DATED : April 24, 2018  
INVENTOR(S) : Rong-Hwa Lin et al.

Page 1 of 2

It is certified that error appears in the above-identified patent and that said Letters Patent is hereby corrected as shown below:

In the Claims

At Column 156, Claim number 29, Line number 35, please replace

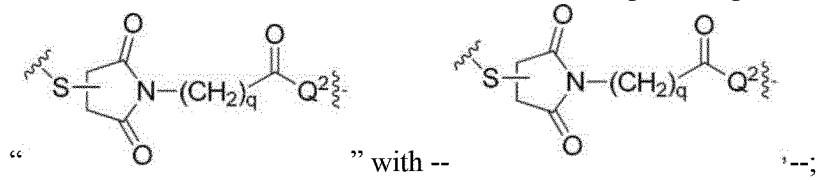

" with --  '--;

At Column 157, Claim number 32, Line number 45, please replace

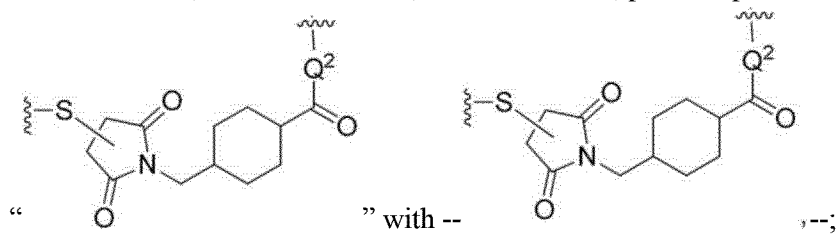

" with --  ,--;

At Column 159, Claim number 37, Line number 1, please replace "The compound of claim 2, wherein A L$^4$ L$^3$ L$^2$ is" with --The compound of claim 2, wherein –A–L$^4$–L$^3$–L$^2$– is--;

Signed and Sealed this  
Fourth Day of December, 2018

Andrei Iancu  
*Director of the United States Patent and Trademark Office*

CERTIFICATE OF CORRECTION (continued)
U.S. Pat. No. 9,950,077 B2

At Columns 161 and 162, Claim number 38, starting on Line number 15, please replace "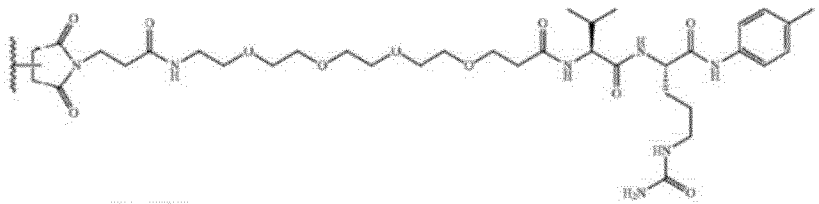

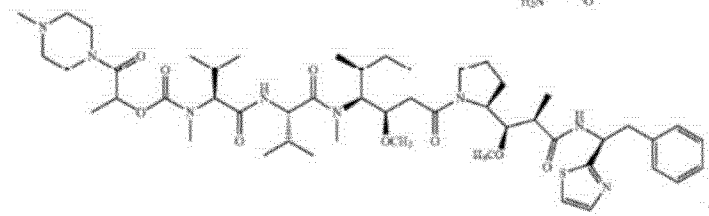" with

"--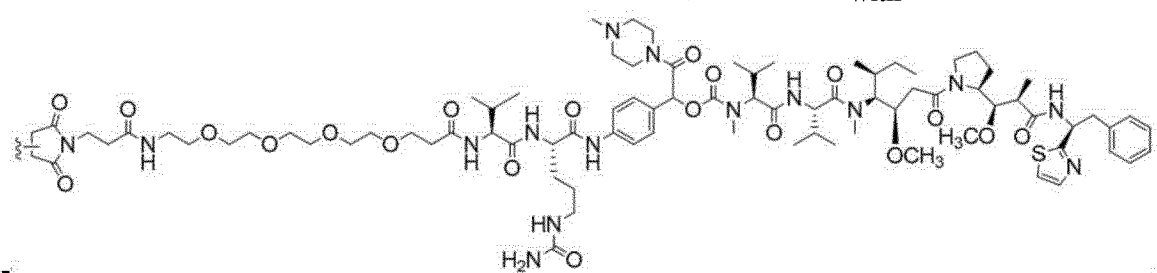--;

and

At Columns 161, 162, 163 and 164, Claim number 39, starting on Line number 50 of Columns 161 and 162, please replace "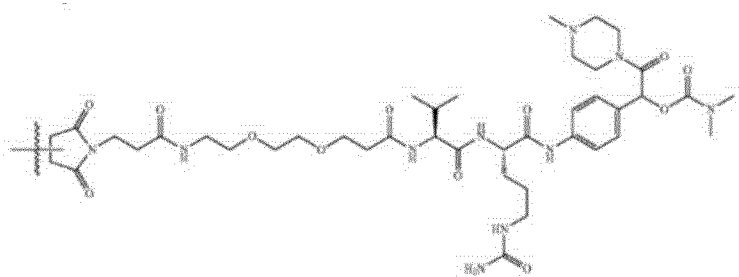

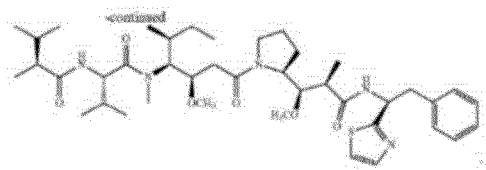" with

"--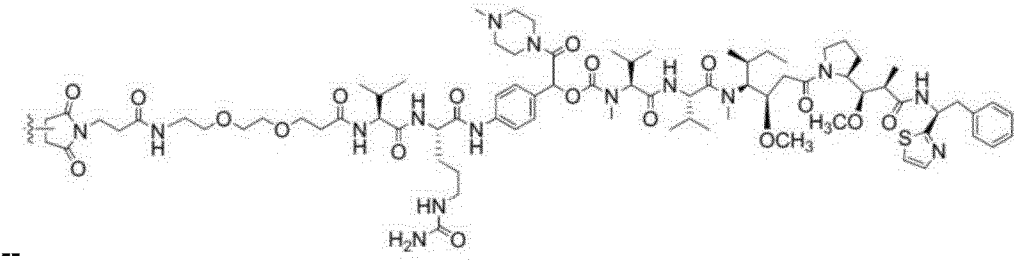--.